US007803395B2

(12) United States Patent
Datta et al.

(10) Patent No.: US 7,803,395 B2
(45) Date of Patent: *Sep. 28, 2010

(54) RETICULATED ELASTOMERIC MATRICES, THEIR MANUFACTURE AND USE IN IMPLANTABLE DEVICES

(75) Inventors: Arindam Datta, Hillsborough, NJ (US); Craig Friedman, Westport, CT (US); Daniel Klempner, West Bloomfield, MI (US); Aisa Sendijarevic, Troy, MI (US)

(73) Assignee: Biomerix Corporation, New York, NY (US)

( * ) Notice: Subject to any disclaimer, the term of this patent is extended or adjusted under 35 U.S.C. 154(b) by 913 days.

This patent is subject to a terminal disclaimer.

(21) Appl. No.: 10/848,624

(22) Filed: May 17, 2004

(65) Prior Publication Data
US 2005/0043816 A1 Feb. 24, 2005

Related U.S. Application Data

(60) Provisional application No. 60/471,518, filed on May 15, 2003.

(51) Int. Cl.
*A61K 9/22* (2006.01)
(52) U.S. Cl. .................... 424/426; 428/160; 428/423.1; 604/890.1
(58) Field of Classification Search ................. 424/426; 428/114, 116, 118, 160, 423.1
See application file for complete search history.

(56) References Cited

U.S. PATENT DOCUMENTS

| | | | |
|---|---|---|---|
| 1,896,071 A | 2/1933 | Clark | |
| 2,546,754 A | 3/1951 | Jones | |
| 2,616,422 A | 11/1952 | Jones | |
| 3,175,025 A | 3/1965 | Geen et al. | 264/80 |
| 3,279,996 A | 10/1966 | Long | |
| 3,334,629 A | 8/1967 | Cohn | |
| 3,789,841 A | 2/1974 | Antoshkiw | |
| 3,896,819 A | 7/1975 | Zaffaroni | |
| 3,946,106 A | 3/1976 | Chien | |
| 4,282,199 A | 8/1981 | Lamond et al. | |
| 4,315,844 A | 2/1982 | Aboytes | |
| 4,459,252 A | 7/1984 | MacGregor | 264/46.9 |
| 4,503,569 A | 3/1985 | Dotter | |
| 4,512,338 A | 4/1985 | Balko et al. | |
| 4,531,916 A | 7/1985 | Scantlebury et al. | |
| 4,545,390 A | 10/1985 | Leary | |
| 4,619,274 A | 10/1986 | Morrison | |
| 4,643,184 A | 2/1987 | Mobin-Uddin | |
| 4,689,386 A | 8/1987 | Chapman et al. | 528/71 |
| 4,737,152 A | 4/1988 | Alchas | |
| 4,739,768 A | 4/1988 | Engelson | |
| 4,776,337 A | 10/1988 | Palmaz | |
| 4,781,177 A | 11/1988 | Lebigot | |
| 4,813,934 A | 3/1989 | Engelson et al. | |
| 4,832,047 A | 5/1989 | Sepetka et al. | |
| 4,832,055 A | 5/1989 | Palestrant | |
| 4,871,542 A | 10/1989 | Vilhardt | |
| 4,884,579 A | 12/1989 | Engelson | |
| 4,890,612 A | 1/1990 | Kensey | |
| 4,913,141 A | 4/1990 | Hillstead | |
| 4,923,464 A | 5/1990 | DiPisa, Jr. | |
| 4,955,862 A | 9/1990 | Sepetka | |
| 4,957,501 A | 9/1990 | Lahille et al. | |
| 4,985,467 A | 1/1991 | Kelly et al. | |
| 4,994,069 A | 2/1991 | Ritchart et al. | |
| 5,002,556 A | 3/1991 | Ishida et al. | |
| 5,013,316 A | 5/1991 | Goble et al. | |
| 5,019,090 A | 5/1991 | Pinchuk | 606/194 |
| 5,035,891 A | 7/1991 | Runkel et al. | |
| 5,037,427 A | 8/1991 | Harada et al. | |
| 5,061,274 A | 10/1991 | Kensey | |
| 5,061,914 A | 10/1991 | Busch et al. | |
| 5,062,829 A | 11/1991 | Pryor et al. | |
| 5,064,434 A | 11/1991 | Haber | |
| 5,070,172 A | 12/1991 | Hirai et al. | |
| 5,092,877 A | 3/1992 | Pinchuk | 631/1 |
| 5,098,374 A | 3/1992 | Othel-Jacobsen et al. | |
| 5,098,440 A | 3/1992 | Hillstead | |
| 5,108,407 A | 4/1992 | Geremia | |
| 5,108,438 A | 4/1992 | Stone | |

(Continued)

FOREIGN PATENT DOCUMENTS

CA 2385613 12/2005

(Continued)

OTHER PUBLICATIONS

Berghaus et al., "Poröse Kunststoffe für die Ohrmuschelplastik" (w/ English Abstract), Laryng. Rhinol. Otol. 62:320-327 (1983).
Campbell et al., "Microtopography and Soft Tissue Response," J. Investigative Surgery 2:51-74 (1989).
"Reticulated Foams," Encyclopedia of Polymer Science and Technology 12:102-104 (1970).
Metcalfe et al., "Cold Hibernated Elastic Memory Foams for Endovascular Interventions," Biomaterials 24:491-497 (2003).
Mohanty et al., "Evaluation of Soft Tissue Response to a Poly(urethane urea)," Biomaterials 13(10):651-656 (1992).
Morehead et al., "Soft-Tissue Response to Synthetic Biomaterials," Otolaryngologic Clinics of North America 27(1):195-201 (1994).
Murphy et al., "Salt Fusion: An Approach to Improve Pore Interconnectivity within Tissue Engineering Scaffolds," Tissue Engineering 8(1):43-52 (2002).

(Continued)

*Primary Examiner*—Sharon E. Kennedy
(74) *Attorney, Agent, or Firm*—Scott T. Weingaertner; Wan Chieh Lee; King & Spalding LLP

(57) ABSTRACT

This invention relates to biodurable, reticulated elastomeric matrices that are resiliently-compressible, their manufacture and uses including uses for implantable devices into or for topical treatment of patients, such as humans and other animals, for therapeutic, nutritional, or other useful purposes.

26 Claims, 3 Drawing Sheets

U.S. PATENT DOCUMENTS

| | | |
|---|---|---|
| 5,109,867 A | 5/1992 | Twyford |
| 5,120,816 A | 6/1992 | Gould et al. |
| 5,122,136 A | 6/1992 | Guglielmi et al. |
| 5,132,415 A | 7/1992 | Diamantoglou et al. |
| 5,133,731 A | 7/1992 | Butler |
| 5,133,742 A | 7/1992 | Pinchuk ........................ 632/1 |
| 5,133,755 A | 7/1992 | Brekke ........................ 623/16 |
| 5,167,624 A | 12/1992 | Butler |
| 5,174,276 A | 12/1992 | Crockard |
| 5,217,484 A | 6/1993 | Marks |
| 5,228,453 A | 7/1993 | Sepetka |
| 5,229,431 A | 7/1993 | Pinchuk ...................... 521/159 |
| 5,234,437 A | 8/1993 | Sepetka |
| 5,250,071 A | 10/1993 | Palermo |
| 5,254,295 A | 10/1993 | Guglielmi et al. |
| 5,256,146 A | 10/1993 | Ensminger et al. |
| 5,258,000 A | 11/1993 | Gianturco |
| 5,261,916 A | 11/1993 | Engelson |
| 5,263,964 A | 11/1993 | Purdy |
| 5,290,295 A | 3/1994 | Querals et al. |
| 5,296,518 A | 3/1994 | Grasel et al. |
| 5,304,195 A | 4/1994 | Twyford |
| 5,308,342 A | 5/1994 | Sepetka et al. |
| 5,312,356 A | 5/1994 | Engelson et al. |
| 5,312,415 A | 5/1994 | Palermo |
| 5,318,527 A | 6/1994 | Hyde et al. |
| 5,334,210 A | 8/1994 | Gianturco |
| 5,350,397 A | 9/1994 | Palermo et al. |
| 5,354,295 A | 10/1994 | Guglielmi et al. |
| 5,356,388 A | 10/1994 | Sepetka et al. |
| 5,380,334 A | 1/1995 | Torrie et al. |
| 5,382,259 A | 1/1995 | Phelps et al. |
| 5,417,708 A | 5/1995 | Hall et al. |
| 5,423,829 A | 6/1995 | Pham et al. |
| 5,423,849 A | 6/1995 | Engelson et al. |
| 5,429,605 A | 7/1995 | Bernd et al. |
| 5,487,385 A | 1/1996 | Avitall |
| 5,496,305 A | 3/1996 | Kittrell et al. |
| 5,514,085 A | 5/1996 | Yoon |
| 5,514,378 A | 5/1996 | Mikos et al. ................. 424/425 |
| 5,520,700 A | 5/1996 | Beyar et al. |
| 5,522,819 A | 6/1996 | Graves et al. |
| 5,522,836 A | 6/1996 | Palermo |
| 5,522,895 A | 6/1996 | Mikos ......................... 623/16 |
| 5,525,348 A | 6/1996 | Whitbourne et al. |
| 5,540,680 A | 7/1996 | Guglielmi et al. |
| 5,551,443 A | 9/1996 | Sepetka et al. |
| 5,556,429 A | 9/1996 | Felt |
| 5,562,698 A | 10/1996 | Parker |
| 5,578,074 A | 11/1996 | Mirigian |
| 5,582,619 A | 12/1996 | Ken |
| 5,601,600 A | 2/1997 | Ton |
| 5,607,474 A | 3/1997 | Athanasiou et al. ........... 623/11 |
| 5,618,314 A | 4/1997 | Harwin et al. .............. 606/232 |
| 5,624,449 A | 4/1997 | Pham |
| 5,629,008 A | 5/1997 | Lee |
| 5,634,926 A | 6/1997 | Jobe |
| 5,658,308 A | 8/1997 | Snyder |
| 5,667,513 A | 9/1997 | Torrie et al. |
| 5,677,355 A | 10/1997 | Shalaby et al. ................ 521/61 |
| 5,686,091 A | 11/1997 | Leong et al. ................ 424/426 |
| 5,690,666 A | 11/1997 | Berenstein et al. |
| 5,690,671 A | 11/1997 | McGurk et al. |
| 5,692,008 A | 11/1997 | Van Nee |
| 5,709,934 A | 1/1998 | Bell et al. |
| 5,711,960 A | 1/1998 | Shikinami |
| 5,716,413 A | 2/1998 | Walter et al. .................. 623/16 |
| 5,718,711 A | 2/1998 | Berenstein et al. |
| 5,722,989 A | 3/1998 | Fitch |
| 5,725,534 A | 3/1998 | Rasmussen |
| 5,725,546 A | 3/1998 | Samson |
| 5,725,568 A | 3/1998 | Hastings |
| 5,726,161 A | 3/1998 | Whistler ....................... 514/54 |
| 5,730,757 A | 3/1998 | Benetti et al. |
| 5,741,331 A | 4/1998 | Pinchuk ....................... 623/11 |
| 5,746,769 A | 5/1998 | Ton |
| 5,749,894 A | 5/1998 | Engelson |
| 5,750,585 A | 5/1998 | Park et al. .................... 521/143 |
| 5,755,774 A | 5/1998 | Pinchuk |
| 5,755,777 A | 5/1998 | Chuter |
| 5,759,161 A | 6/1998 | Ogawa |
| 5,766,160 A | 6/1998 | Samson et al. |
| 5,766,631 A | 6/1998 | Arnold |
| 5,769,870 A | 6/1998 | Salahieh et al. |
| 5,769,899 A | 6/1998 | Schwartz et al. .............. 623/18 |
| 5,770,193 A | 6/1998 | Vacanti et al. .............. 424/93.7 |
| 5,776,154 A | 7/1998 | Taylor et al. |
| 5,776,184 A | 7/1998 | Tuch |
| 5,789,018 A | 8/1998 | Engelson et al. |
| 5,800,453 A | 9/1998 | Gia |
| 5,800,455 A | 9/1998 | Palermo |
| 5,814,062 A | 9/1998 | Sepetka |
| 5,820,917 A | 10/1998 | Tuch ........................... 427/2.1 |
| 5,823,198 A | 10/1998 | Jones et al. |
| 5,824,081 A | 10/1998 | Knapp et al. |
| 5,826,587 A | 10/1998 | Berenstein et al. |
| 5,830,183 A | 11/1998 | Krieger |
| 5,833,705 A | 11/1998 | Ken et al. |
| 5,843,118 A | 12/1998 | Sepetka et al. |
| 5,846,210 A | 12/1998 | Ogawa et al. |
| 5,851,206 A | 12/1998 | Guglielmi et al. |
| 5,853,418 A | 12/1998 | Ken et al. |
| 5,855,578 A | 1/1999 | Guglielmi |
| 5,863,627 A | 1/1999 | Szycher ...................... 428/36.8 |
| 5,865,814 A | 2/1999 | Tuch ........................... 604/265 |
| 5,865,844 A | 2/1999 | Plaia et al. |
| 5,871,496 A | 2/1999 | Ginn et al. |
| 5,882,334 A | 3/1999 | Sepetka et al. |
| 5,891,128 A | 4/1999 | Gia et al. |
| 5,891,130 A | 4/1999 | Palermo |
| 5,891,159 A | 4/1999 | Sherman et al. |
| 5,891,192 A | 4/1999 | Murayama et al. |
| 5,891,558 A | 4/1999 | Bell et al. .................... 428/218 |
| 5,894,843 A | 4/1999 | Benetti et al. |
| 5,895,385 A | 4/1999 | Guglielmi |
| 5,895,391 A | 4/1999 | Farnholtz |
| 5,895,407 A | 4/1999 | Jayaraman |
| 5,904,703 A | 5/1999 | Gilson |
| 5,911,728 A | 6/1999 | Sepetka et al. |
| 5,911,731 A | 6/1999 | Pham et al. |
| 5,916,235 A | 6/1999 | Guglielmi |
| 5,925,037 A | 7/1999 | Guglielmi |
| 5,925,054 A | 7/1999 | Taylor et al. |
| 5,925,059 A | 7/1999 | Palermo et al. |
| 5,925,060 A | 7/1999 | Forber |
| 5,928,226 A | 7/1999 | Guglielmi |
| 5,928,260 A | 7/1999 | Chin et al. |
| 5,944,714 A | 8/1999 | Guglielmi |
| 5,944,733 A | 8/1999 | Engelson |
| 5,944,736 A | 8/1999 | Taylor et al. |
| 5,947,962 A | 9/1999 | Guglielmi |
| 5,947,963 A | 9/1999 | Guglielmi |
| 5,951,539 A | 9/1999 | Nita et al. |
| 5,962,620 A | 10/1999 | Reich et al. |
| 5,968,078 A | 10/1999 | Grotz |
| 5,976,126 A | 11/1999 | Guglielmi |
| 5,984,929 A | 11/1999 | Bashiri |
| 5,986,034 A | 11/1999 | DiDomenico et al. ......... 528/72 |
| 5,989,242 A | 11/1999 | Saadat |
| 6,001,111 A | 12/1999 | Sepetka et al. |
| 6,010,498 A | 1/2000 | Guglielmi |
| 6,011,995 A | 1/2000 | Guglielmi et al. |
| 6,015,422 A | 1/2000 | Kerr |
| 6,015,424 A | 1/2000 | Rosenbluth et al. |

| | | | |
|---|---|---|---|
| 6,019,757 A | 2/2000 | Scheldrup | |
| 6,019,771 A | 2/2000 | Bennett et al. | |
| 6,022,340 A | 2/2000 | Sepetka et al. | |
| 6,024,754 A | 2/2000 | Engelson | |
| 6,033,423 A | 3/2000 | Ken et al. | |
| 6,034,149 A | 3/2000 | Bleys et al. | |
| 6,036,706 A | 3/2000 | Morejohn et al. | |
| 6,036,720 A | 3/2000 | Abrams et al. | |
| 6,039,967 A | 3/2000 | Ottoboni | |
| 6,042,563 A | 3/2000 | Morejohn et al. | |
| 6,042,592 A | 3/2000 | Schmitt | |
| 6,048,333 A | 4/2000 | Lennox et al. | |
| 6,050,266 A | 4/2000 | Benetti et al. | |
| 6,054,142 A | 4/2000 | Li et al. | 424/426 |
| 6,063,070 A | 5/2000 | Eder | |
| 6,063,100 A | 5/2000 | Diaz | |
| 6,063,104 A | 5/2000 | Villar et al. | |
| 6,063,395 A | 5/2000 | Markkula | |
| 6,066,133 A | 5/2000 | Guglielmi | |
| 6,066,776 A | 5/2000 | Goodwin et al. | |
| 6,068,644 A | 5/2000 | Lulo | |
| 6,071,297 A | 6/2000 | Salahieh et al. | |
| 6,077,260 A | 6/2000 | Wheelock | |
| 6,083,220 A | 7/2000 | Guglielmi | |
| 6,086,591 A | 7/2000 | Bojarski | |
| 6,093,199 A | 7/2000 | Brown et al. | |
| 6,096,060 A | 8/2000 | Fitts et al. | |
| 6,099,562 A | 8/2000 | Ding et al. | |
| 6,102,917 A | 8/2000 | Maitland | |
| 6,102,932 A | 8/2000 | Kurz | |
| 6,102,939 A | 8/2000 | Pinchuk | 623/1 |
| 6,110,190 A | 8/2000 | Ginn et al. | |
| 6,111,052 A | 8/2000 | DiDomenico et al. | 528/72 |
| 6,113,616 A | 9/2000 | Taylor et al. | |
| 6,113,622 A | 9/2000 | Hieshima | |
| 6,113,629 A | 9/2000 | Ken | |
| 6,117,142 A | 9/2000 | Goodson | |
| 6,117,441 A | 9/2000 | Moo-Young | |
| 6,123,714 A | 9/2000 | Gia et al. | |
| 6,135,193 A | 10/2000 | Lloyd | |
| 6,136,015 A | 10/2000 | Kurz et al. | |
| 6,139,510 A | 10/2000 | Palermo | |
| 6,139,520 A | 10/2000 | McCrory et al. | |
| 6,139,535 A | 10/2000 | Greelis | |
| 6,139,564 A | 10/2000 | Teoh | |
| 6,149,664 A | 11/2000 | Kurz | |
| 6,149,678 A | 11/2000 | DiDomenico et al. | 607/122 |
| 6,153,292 A | 11/2000 | Bell et al. | |
| 6,159,165 A | 12/2000 | Ferrera et al. | |
| 6,165,193 A | 12/2000 | Greene, Jr. et al. | 606/191 |
| 6,165,212 A | 12/2000 | Dereume et al. | |
| 6,168,592 B1 | 1/2001 | Kupiecki et al. | |
| 6,168,615 B1 | 1/2001 | Ken et al. | |
| 6,168,622 B1 | 1/2001 | Mazzocchi | |
| 6,169,048 B1 | 1/2001 | Sjögren et al. | 501/95.3 |
| 6,171,298 B1 | 1/2001 | Matsuura | |
| 6,177,522 B1 | 1/2001 | Brady et al. | 525/452 |
| 6,183,461 B1 | 2/2001 | Matsuura et al. | |
| 6,183,491 B1 | 2/2001 | Lulo | |
| 6,183,518 B1 | 2/2001 | Ross | |
| 6,187,027 B1 | 2/2001 | Mariant et al. | |
| 6,190,311 B1 | 2/2001 | Glines et al. | |
| 6,190,357 B1 | 2/2001 | Ferrari et al. | |
| 6,190,373 B1 | 2/2001 | Palermo | |
| 6,193,708 B1 | 2/2001 | Ken et al. | |
| RE37,117 E | 3/2001 | Palermo | |
| 6,197,240 B1 | 3/2001 | Pinchuk | 264/309 |
| 6,203,547 B1 | 3/2001 | Nguyen | |
| 6,207,180 B1 | 3/2001 | Ottoboni et al. | |
| 6,213,941 B1 | 4/2001 | Benetti et al. | |
| 6,214,002 B1 | 4/2001 | Fleischman et al. | |
| 6,214,022 B1 | 4/2001 | Taylor et al. | |
| 6,221,061 B1 | 4/2001 | Engelson et al. | |
| 6,221,066 B1 | 4/2001 | Ferrera et al. | |
| 6,224,610 B1 | 5/2001 | Ferrera | |
| 6,224,630 B1 | 5/2001 | Bao et al. | |
| 6,231,586 B1 | 5/2001 | Mariant | |
| 6,231,590 B1 | 5/2001 | Slaikeu et al. | |
| 6,231,879 B1 | 5/2001 | Li et al. | 424/422 |
| 6,238,403 B1 | 5/2001 | Greene, Jr. et al. | |
| 6,238,415 B1 | 5/2001 | Sepetka et al. | |
| 6,245,090 B1 | 6/2001 | Gilson et al. | 606/213 |
| 6,245,107 B1 | 6/2001 | Ferree | |
| 6,254,592 B1 | 7/2001 | Samson et al. | |
| 6,258,055 B1 | 7/2001 | McCrory et al. | |
| 6,270,456 B1 | 8/2001 | Keith et al. | |
| 6,270,465 B1 | 8/2001 | Keith et al. | |
| 6,273,897 B1 | 8/2001 | Dalessandro et al. | |
| 6,277,125 B1 | 8/2001 | Barry | |
| 6,277,126 B1 | 8/2001 | Barry | |
| 6,280,455 B1 | 8/2001 | Ginn et al. | |
| 6,280,457 B1 | 8/2001 | Wallace et al. | |
| 6,290,691 B1 | 9/2001 | Krieger | |
| 6,293,923 B1 | 9/2001 | Yachia | |
| 6,296,622 B1 | 10/2001 | Kurz | |
| 6,299,619 B1 | 10/2001 | Greene, Jr. et al. | |
| 6,306,153 B1 | 10/2001 | Kurz et al. | |
| 6,306,159 B1 | 10/2001 | Schwartz et al. | |
| 6,306,424 B1 | 10/2001 | Vyakarnam et al. | 424/426 |
| 6,309,413 B1 | 10/2001 | Dereume et al. | 623/1.13 |
| 6,312,421 B1 | 11/2001 | Boock | |
| 6,313,254 B1 | 11/2001 | Meijs et al. | 528/26 |
| 6,315,717 B1 | 11/2001 | Benetti et al. | |
| 6,319,267 B1 | 11/2001 | Kurz | |
| 6,322,576 B1 | 11/2001 | Wallace et al. | |
| 6,333,029 B1 | 12/2001 | Vyakarnam et al. | |
| 6,335,384 B1 | 1/2002 | Evans et al. | |
| 6,344,048 B1 | 2/2002 | Chin et al. | |
| 6,346,077 B1 | 2/2002 | Taylor et al. | |
| 6,346,117 B1 | 2/2002 | Greenhalgh | |
| 6,444,035 B1 | 2/2002 | Chudzik et al. | |
| 6,355,030 B1 | 3/2002 | Aldrich et al. | |
| 6,355,063 B1 | 3/2002 | Calcote | 623/1.42 |
| 6,355,699 B1 | 3/2002 | Vyakarnam et al. | 521/61 |
| 6,361,547 B1 | 3/2002 | Hieshima | |
| 6,365,149 B2 | 4/2002 | Vyakarnam et al. | 424/93.1 |
| 6,368,338 B1 | 4/2002 | Konya et al. | |
| 6,372,228 B1 | 4/2002 | Gregory | |
| 6,375,662 B1 | 4/2002 | Schmitt | |
| 6,375,668 B1 | 4/2002 | Gifford et al. | |
| 6,375,669 B1 | 4/2002 | Rosenbluth et al. | |
| 6,379,329 B1 | 4/2002 | Naglreiter et al. | |
| 6,379,373 B1 | 4/2002 | Sawhney et al. | |
| 6,379,374 B1 | 4/2002 | Hieshima | |
| 6,383,171 B1 | 5/2002 | Gifford et al. | |
| 6,387,108 B1 | 5/2002 | Taylor et al. | |
| 6,394,951 B1 | 5/2002 | Taylor et al. | |
| 6,398,718 B1 | 6/2002 | Yachia et al. | |
| 6,402,750 B1 | 6/2002 | Atkinson et al. | |
| 6,409,721 B1 | 6/2002 | Wheelock | |
| 6,420,452 B1 | 7/2002 | Gunatillake et al. | 523/105 |
| 6,425,893 B1 | 7/2002 | Guglielmi | |
| 6,425,919 B1 | 7/2002 | Lambrecht | |
| 6,428,557 B1 | 8/2002 | Hilaire | |
| 6,428,558 B1 | 8/2002 | Jones et al. | |
| 6,428,576 B1 | 8/2002 | Haldimann | |
| 6,430,426 B2 | 8/2002 | Avitall | |
| 6,432,122 B1 | 8/2002 | Gilson et al. | |
| 6,436,135 B1 | 8/2002 | Goldfarb | 623/1.39 |
| 6,437,073 B1 | 8/2002 | Gunatilake et al. | 528/28 |
| 6,448,049 B1 | 9/2002 | Tsutsumi et al. | 435/98 |
| 6,454,780 B1 | 9/2002 | Wallace | |
| 6,454,811 B1 | 9/2002 | Sherwood et al. | |
| 6,458,119 B1 | 10/2002 | Berenstein et al. | |
| 6,458,127 B1 | 10/2002 | Truckai et al. | |
| 6,475,232 B1 | 11/2002 | Babbs et al. | |

| Patent No. | Date | Inventor | | Patent No. | Date | Inventor | |
|---|---|---|---|---|---|---|---|
| 6,478,773 B1 | 11/2002 | Gandhi | | 6,884,428 B2 | 4/2005 | Binette et al. | |
| 6,482,235 B1 | 11/2002 | Lambrecht et al. | | 6,893,464 B2 | 5/2005 | Kiester | |
| 6,485,575 B2 | 11/2002 | Yuan | 127/71 | 6,905,503 B2 | 6/2005 | Gifford et al. | |
| 6,494,884 B2 | 12/2002 | Gifford | | 6,953,473 B2 | 10/2005 | Porter | |
| 6,500,149 B2 | 12/2002 | Gandhi | | 6,958,068 B2 | 10/2005 | Hieshima | |
| 6,500,190 B2 | 12/2002 | Greene, Jr. et al. | | 6,966,892 B2 | 11/2005 | Gandhi et al. | |
| 6,506,204 B2 | 1/2003 | Mazzocchi | | 6,984,247 B2 | 1/2006 | Cauthen | |
| 6,514,264 B1 | 2/2003 | Naglreiter | | 6,994,711 B2 | 2/2006 | Hieshima et al. | |
| 6,514,280 B1 | 2/2003 | Gilson | | 6,994,717 B2 | 2/2006 | Konya et al. | |
| 6,530,934 B1 | 3/2003 | Jacobsen et al. | | 6,997,929 B2 | 2/2006 | Manzi et al. | |
| 6,531,154 B1 | 3/2003 | Mathiowitz et al. | | 7,008,979 B2 | 3/2006 | Schottman et al. | |
| 6,537,569 B2 | 3/2003 | Cruise | | 7,018,394 B2 | 3/2006 | Diaz | |
| 6,544,225 B1 | 4/2003 | Lulo | | 7,025,982 B2 | 4/2006 | Mattes et al. | |
| 6,544,262 B2 | 4/2003 | Fleischman | | 7,029,487 B2 | 4/2006 | Greene | |
| 6,545,097 B2 | 4/2003 | Pinchuk et al. | 525/240 | 7,033,388 B2 | 4/2006 | Zilla et al. | |
| 6,554,842 B2 | 4/2003 | Heuser et al. | | 7,044,962 B2 | 5/2006 | Elliott | |
| 6,569,653 B1 | 5/2003 | Alard et al. | 435/161 | 7,112,417 B2 | 9/2006 | Vyakarnam et al. | |
| 6,578,580 B2 | 6/2003 | Conrad et al. | | 7,128,736 B1 | 10/2006 | Abrams et al. | |
| 6,579,291 B1 | 6/2003 | Keith et al. | | 7,147,618 B2 | 12/2006 | Kurz | |
| 6,589,199 B1 | 7/2003 | McCrory et al. | | 7,160,333 B2 | 1/2007 | Plouhar | |
| 6,589,230 B2 | 7/2003 | Gia et al. | | 7,179,276 B2 | 2/2007 | Barry | |
| 6,589,265 B1 | 7/2003 | Palmer et al. | | 7,182,774 B2 | 2/2007 | Barry | |
| 6,592,625 B2 | 7/2003 | Cauthen | | 7,192,604 B2 | 3/2007 | Brown et al. | |
| 6,599,323 B2 | 7/2003 | Melican et al. | | 7,198,613 B2 | 4/2007 | Gandhi | |
| 6,602,189 B1 | 8/2003 | Bennetti et al. | | 7,255,707 B2 | 8/2007 | Ramzipoor | |
| 6,602,261 B2 | 8/2003 | Greene, Jr. et al. | | 7,323,000 B2 | 1/2008 | Monstdt | |
| 6,602,291 B1 | 8/2003 | Ray et al. | | 2001/0002438 A1 | 5/2001 | Sepetka et al. | |
| 6,605,101 B1 | 8/2003 | Schaefer et al. | | 2001/0016738 A1 | 8/2001 | Harrington et al. | |
| 6,607,538 B1 | 8/2003 | Ferrera et al. | | 2001/0019719 A1 | 9/2001 | Offoloni | |
| 6,610,317 B2 | 8/2003 | Straub et al. | | 2001/0044572 A1 | 11/2001 | Benetti et al. | |
| 6,616,617 B1 | 9/2003 | Ferrera et al. | | 2001/0049521 A1 | 12/2001 | Gia et al. | |
| 6,617,014 B1 | 9/2003 | Thomson | | 2002/0002383 A1 | 1/2002 | Sepetka et al. | |
| 6,620,152 B2 | 9/2003 | Guglielmi | | 2002/0005600 A1 | 1/2002 | Ma | 264/49 |
| 6,623,493 B2 | 9/2003 | Wallace et al. | | 2002/0010388 A1 | 1/2002 | Taylor et al. | |
| 6,635,068 B1 | 10/2003 | Dubrul et al. | | 2002/0018795 A1 | 2/2002 | Whitbourne | |
| 6,636,758 B2 | 10/2003 | Sanchez et al. | | 2002/0018884 A1 | 2/2002 | Thomson | 428/306.6 |
| 6,638,243 B2 | 10/2003 | Kupiecki | | 2002/0040182 A1 | 4/2002 | Benetti et al. | |
| 6,638,245 B2 | 10/2003 | Miller et al. | | 2002/0055730 A1 | 5/2002 | Yachia et al. | |
| 6,638,293 B1 | 10/2003 | Makower et al. | | 2002/0055786 A1 | 5/2002 | Atala | |
| 6,638,312 B2 | 10/2003 | Plouhar et al. | | 2002/0072550 A1 | 6/2002 | Brady et al. | 521/155 |
| 6,656,201 B2 | 12/2003 | Ferrera et al. | | 2002/0072764 A1 | 6/2002 | Sepetka et al. | |
| 6,663,650 B2 | 12/2003 | Sepetka et al. | | 2002/0072791 A1 | 6/2002 | Eder | |
| 6,664,389 B1 | 12/2003 | Shi et al. | 536/102 | 2002/0091380 A1 | 7/2002 | Wheelock | |
| 6,669,706 B2 | 12/2003 | Schmitt et al. | | 2002/0099270 A1 | 7/2002 | Taylor et al. | |
| 6,673,013 B2 | 1/2004 | Benetti et al. | | 2002/0099408 A1 | 7/2002 | Marks | |
| 6,673,285 B2 | 1/2004 | Ma | | 2002/0101008 A1 | 8/2002 | Sokolowski | |
| 6,679,903 B2 | 1/2004 | Kurz | | 2002/0107330 A1 | 8/2002 | Pinchuk et al. | 525/242 |
| 6,689,125 B1 | 2/2004 | Keith et al. | | 2002/0111646 A1 | 8/2002 | Gifford, III et al. | |
| 6,689,141 B2 | 2/2004 | Ferrera | | 2002/0119177 A1 | 8/2002 | Bowman et al. | |
| 6,692,510 B2 | 2/2004 | West | | 2002/0120348 A1 | 8/2002 | Melican et al. | 623/23.72 |
| 6,701,930 B2 | 3/2004 | Benetti et al. | | 2002/0123738 A1 | 9/2002 | Jansen et al. | |
| 6,702,782 B2 | 3/2004 | Miller et al. | | 2002/0123765 A1 | 9/2002 | Sepetka et al. | |
| 6,706,025 B2 | 3/2004 | Engelson et al. | | 2002/0133189 A1 | 9/2002 | Gifford, III et al. | |
| 6,712,842 B1 | 3/2004 | Gifford, III et al. | | 2002/0133190 A1 | 9/2002 | Horton et al. | |
| 6,723,108 B1 | 4/2004 | Jones et al. | | 2002/0138095 A1 | 9/2002 | Mazzocchi et al. | |
| 6,723,112 B2 | 4/2004 | Ho et al. | | 2002/0142413 A1 | 10/2002 | Brady et al. | 435/181 |
| 6,726,621 B2 | 4/2004 | Suon et al. | | 2002/0143349 A1 | 10/2002 | Gifford, III et al. | |
| 6,730,104 B1 | 5/2004 | Sepetka et al. | | 2002/0165450 A1 | 11/2002 | Sanchez et al. | |
| 6,743,169 B1 | 6/2004 | Green et al. | | 2002/0169066 A1 | 11/2002 | Cassidy et al. | |
| 6,743,236 B2 | 6/2004 | Barry | | 2002/0169473 A1 | 11/2002 | Sepetka et al. | |
| 6,746,467 B1 | 6/2004 | Taylor et al. | | 2002/0169495 A1 | 11/2002 | Gifford et al. | |
| 6,746,468 B1 | 6/2004 | Sepetka et al. | | 2002/0169497 A1 | 11/2002 | Wholey et al. | 623/1.13 |
| 6,780,196 B2 | 8/2004 | Chin et al. | | 2002/0169499 A1 | 11/2002 | Zilla et al. | 623/1.15 |
| 6,784,273 B1 | 8/2004 | Spaans et al. | | 2002/0172717 A1 | 11/2002 | Leong et al. | |
| 6,811,560 B2 | 11/2004 | Jones et al. | | 2002/0173851 A1 | 11/2002 | McKay | |
| 6,811,561 B2 | 11/2004 | Diaz | | 2002/0177870 A1 | 11/2002 | Sepetka et al. | |
| 6,824,500 B2 | 11/2004 | Noriega et al. | | 2002/0183858 A1 | 12/2002 | Contiliano et al. | 623/23.76 |
| 6,824,545 B2 | 11/2004 | Sepetka et al. | | 2002/0188311 A1 | 12/2002 | Ferrera | |
| 6,835,185 B2 | 12/2004 | Ramzipoor et al. | | 2002/0198491 A1 | 12/2002 | Miller et al. | |
| 6,846,328 B2 | 1/2005 | Cauthen | | 2002/0198492 A1 | 12/2002 | Miller et al. | |
| 6,849,081 B2 | 2/2005 | Sepetka et al. | | 2002/0198599 A1 | 12/2002 | Haldimann | |
| 6,852,330 B2 | 2/2005 | Bowman et al. | | 2003/0008015 A1 | 1/2003 | Levisage et al. | |
| 6,872,218 B2 | 3/2005 | Ferrera et al. | | 2003/0014073 A1 | 1/2003 | Bashiri | |

| | | |
|---|---|---|
| 2003/0014075 A1 | 1/2003 | Rosenbluth et al. ......... 606/213 |
| 2003/0014118 A1 | 1/2003 | Lambrecht et al. ....... 623/17.16 |
| 2003/0051735 A1 | 3/2003 | Pavcnik et al. .............. 128/831 |
| 2003/0074075 A1 | 4/2003 | Thomas et al. |
| 2003/0100920 A1 | 5/2003 | Akin et al. ................... 606/213 |
| 2003/0120261 A1 | 6/2003 | Gellman |
| 2003/0120345 A1 | 6/2003 | Cauthen |
| 2003/0130689 A1 | 7/2003 | Wallace et al. |
| 2003/0153976 A1 | 8/2003 | Cauthen, III et al. |
| 2003/0171739 A1 | 9/2003 | Murphy et al. |
| 2003/0171773 A1 | 9/2003 | Carrison ..................... 606/213 |
| 2003/0193104 A1 | 10/2003 | Melican |
| 2003/0195560 A1 | 10/2003 | Ginn ......................... 606/213 |
| 2003/0199887 A1 | 10/2003 | Ferrera et al. |
| 2003/0204246 A1 | 10/2003 | Chu et al. ................... 623/1.23 |
| 2003/0208259 A1 | 11/2003 | Penhasi ..................... 623/1.15 |
| 2003/0215564 A1 | 11/2003 | Heller et al. ............... 427/2.25 |
| 2003/0220690 A1 | 11/2003 | Cauthen, III |
| 2004/0039392 A1 | 2/2004 | Trieu |
| 2004/0068314 A1 | 4/2004 | Jones et al. |
| 2004/0073243 A1 | 4/2004 | Sepetka et al. |
| 2004/0078077 A1 | 4/2004 | Binette et al. |
| 2004/0079429 A1 | 4/2004 | Miller et al. |
| 2004/0087834 A1 | 5/2004 | Benetti et al. |
| 2004/0098024 A1 | 5/2004 | Dieck et al. |
| 2004/0115164 A1 | 6/2004 | Pierce et al. |
| 2004/0133233 A1 | 7/2004 | Sepetka et al. |
| 2004/0158282 A1 | 8/2004 | Jones et al. |
| 2004/0161451 A1 | 8/2004 | Pierce et al. |
| 2004/0162519 A1 | 8/2004 | Helkowski et al. |
| 2004/0167534 A1 | 8/2004 | Errico et al. |
| 2004/0175408 A1 | 9/2004 | Chun et al. |
| 2004/0181253 A1 | 9/2004 | Sepetka et al. |
| 2004/0193246 A1 | 9/2004 | Ferrera |
| 2004/0204701 A1 | 10/2004 | Cox |
| 2004/0220563 A1 | 11/2004 | Eder |
| 2004/0230099 A1 | 11/2004 | Taylor et al. |
| 2004/0230285 A1 | 11/2004 | Gifford, III et al. |
| 2004/0265880 A1 | 12/2004 | Donahue et al. |
| 2005/0021023 A1 | 1/2005 | Guglielmi |
| 2005/0021077 A1 | 1/2005 | Chin et al. |
| 2005/0033348 A1 | 2/2005 | Sepetka et al. |
| 2005/0033350 A1 | 2/2005 | Ken et al. |
| 2005/0043585 A1 | 2/2005 | Datta et al. |
| 2005/0043780 A1 | 2/2005 | Gifford et al. |
| 2005/0043816 A1 | 2/2005 | Datta et al. |
| 2005/0049619 A1 | 3/2005 | Sepetka et al. |
| 2005/0059995 A1 | 3/2005 | Sepetka et al. |
| 2005/0060022 A1 | 3/2005 | Felt et al. |
| 2005/0085849 A1 | 4/2005 | Sepetka et al. |
| 2005/0125024 A1 | 6/2005 | Sepetka et al. |
| 2005/0149046 A1 | 7/2005 | Friedman et al. |
| 2005/0149108 A1 | 7/2005 | Cox |
| 2005/0149197 A1 | 7/2005 | Cauthen |
| 2005/0154417 A1 | 7/2005 | Sepetka |
| 2005/0154463 A1 | 7/2005 | Trieu |
| 2005/0165480 A1 | 7/2005 | Jordan et al. |
| 2005/0171572 A1 | 8/2005 | Martinez |
| 2005/0177237 A1 | 8/2005 | Shappley et al. |
| 2005/0182418 A1 | 8/2005 | Boyd |
| 2005/0209696 A1 | 9/2005 | Lin et al. |
| 2005/0216030 A1 | 9/2005 | Sepetka et al. |
| 2005/0216050 A1 | 9/2005 | Sepetka et al. |
| 2005/0222580 A1 | 10/2005 | Gifford, III et al. |
| 2005/0222662 A1 | 10/2005 | Thompson |
| 2005/0245882 A1 | 11/2005 | Elkins et al. |
| 2005/0246021 A1 | 11/2005 | Ringeisen et al. |
| 2005/0251200 A1 | 11/2005 | Porter |
| 2005/0288686 A1 | 12/2005 | Sepetka et al. |
| 2006/0015182 A1 | 1/2006 | Tsou |
| 2006/0025801 A1 | 2/2006 | Lulo |
| 2006/0025802 A1 | 2/2006 | Sowers |
| 2006/0025803 A1 | 2/2006 | Mitelberg |
| 2006/0030814 A1 | 2/2006 | Valencia et al. |
| 2006/0030939 A1 | 2/2006 | Frank |
| 2006/0036218 A1 | 2/2006 | Goodson et al. |
| 2006/0052814 A1 | 3/2006 | Sater |
| 2006/0052815 A1 | 3/2006 | Fitz |
| 2006/0052816 A1 | 3/2006 | Bates |
| 2006/0069323 A1 | 3/2006 | Elkins et al. |
| 2006/0106420 A1 | 5/2006 | Dolan et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |
| 2006/0195137 A1 | 8/2006 | Sepetka et al. |
| 2006/0200192 A1 | 9/2006 | Fitz et al. |
| 2006/0265044 A1 | 11/2006 | Gifford, III et al. |
| 2006/0282112 A1 | 12/2006 | Griffin |
| 2007/0118172 A1 | 5/2007 | Balgobin |
| 2007/0270903 A1 | 11/2007 | Davis |
| 2007/0293930 A1 | 12/2007 | Wang |
| 2008/0027482 A1 | 1/2008 | Sekido |
| 2008/0045997 A1 | 2/2008 | Balgobin |

FOREIGN PATENT DOCUMENTS

| | | |
|---|---|---|
| EP | 0572932 | 12/1993 |
| EP | 0649288 | 12/1993 |
| EP | 0598025 | 5/1994 |
| EP | 0601044 | 6/1994 |
| EP | 0606392 | 7/1994 |
| EP | 0615459 | 9/1994 |
| EP | 0617632 | 10/1994 |
| EP | 0681492 | 7/1995 |
| EP | 0693948 | 12/1995 |
| EP | 0703798 | 4/1996 |
| EP | 0711532 | 5/1996 |
| EP | 0754435 | 1/1997 |
| EP | 0765636 | 4/1997 |
| EP | 0778005 | 6/1997 |
| EP | 0847772 | 6/1998 |
| EP | 0853955 | 7/1998 |
| EP | 0616543 | 9/1998 |
| EP | 0970704 | 1/2000 |
| EP | 0820726 | 9/2003 |
| EP | 0274898 | 12/2005 |
| EP | 1202683 | 5/2006 |
| WO | 94/06460 | 3/1994 |
| WO | 98/46287 | 10/1998 |
| WO | 99/05977 | 2/1999 |
| WO | 99/23954 | 5/1999 |
| WO | 99/024084 | 5/1999 |
| WO | 99/24084 | 5/1999 |
| WO | 99/24106 | 5/1999 |
| WO | 99/61084 | 12/1999 |
| WO | 00/07524 | 2/2000 |
| WO | 00/67812 | 11/2000 |
| WO | 01/03607 | 1/2001 |
| WO | WO 01/21108 A1 | 3/2001 |
| WO | 01/074581 | 10/2001 |
| WO | 01/74582 | 10/2001 |
| WO | WO 01/74582 A1 | 10/2001 |
| WO | WO 2004/02351 | 1/2004 |
| WO | WO 2004/62531 | 7/2004 |
| WO | WO 2006/88531 | 8/2006 |

OTHER PUBLICATIONS

Pinchuk, "A review of the biostability and carcinogenecity of polyurethanes in medicine and the new generation of 'biostable' polyurethanes," J. Biomater. Sci. Polymer Edn. 6(3):225-267 (1994).

Ward et al., "The Effect of Microgeometry, Implant Thickness and Polyurethane Chemistry on the Foreign Body Response to Subcutaneous Implants," Biomaterials 23:4185-4192 (2002).

Yang et al., "The Design of Scaffolds for Use in Tissue Engineering. Part I. Traditional Factors," Tissue Engineering 7(6):679-689 (2001).

U.S. Appl. No. 60/471,518, filed May 15, 2003, Constantino et al.
U.S. Appl. No. 60/471,520, filed May 15, 2003, Constantino et al.
Bioabsorbable Polymers <<http://courses.ahc.umn.edu/medical-school/BMEn/5001/notes/bioabs.html>>, pp. 1-8
Gianturco-Gritka Vascular Occlusion Devices <<www.cookmedical.com/di/dataSheet.do? id=39>>, 2006.
Pediatric Cardiology <<www.egyptheart.org/EHJI/JESPCI/jespc02.htm>> The Egyptian Society of Pediatric Cardiologists, Vol./Iss: 1(2), pp. 1-18, Dec. 1997.
Ahlgren et al. Anular Incision Technique on the Strength and Multidirectional Flexibility of the Healing Intervertebral Disc, *Spine*, Vol./Iss: 19(8), pp. 948-954, 1994.
Ahlgren et al., Effect of Anular Repair on the Healing Strength of the Intervertebral Disc, *Spine*, Vol./Iss: 25(17), pp. 2165-2170, 2000.
B. W. Sauer et al., Porous High Density Polyethylene (PHDPE) - Autogenous Tissue Tracheal Prosthesis, *Trans Am. Soc. Artif. Intern. Organs*, Vol./Iss: 28, pp. 369-373, Apr. 14-16.
Barone et al., The Biomechanical and Histopathologic Effects of Surface Texturing with Silicone and Polyurethane in Tissue Implantation and Expansion, *Plast. Reconstr. Surg.*, Vol./Iss: 90(1), pp. 77-86, 1992.
Bettina Marty et al., Biologic Fixation of Polyester-versus Polyurethane-covered Stents in a Porcine Model, *Laboratory Investigations*, Vol./Iss: 13(6), pp. 601-607 Jun. 2002.
Clarke et al., Innovative Manufacture of-Olefin Foams, *Paper 17 in the proceedings of Blowing Agents and Foaming Processes, Munich Germany*, 2006.
David J. Mooney et al., Novel Approach to Fabricate Porous Sponges of poly(D,L-lactic-co-glycolic acid) without the use of organic solvents, *Biomaterials*, Vol./Iss: 17, pp. 1417-1422, 1996.
Eugene Whilte et al., Biomaterial Aspects of Interpore-200 Porous Hydroxyapatite, *Dental Clinics of North America*, Vol./Iss: 30(1), pp. 49-67, Jan. 1986.
Fraser et al., The Future of Bladder Control - Intravesical Drug Delivery, a Pinch of Pepper and Gene Therapy, *Reviews in Urology*, Vol./Iss: 4(1), pp. 1-11, 2002.
Hugh U. Cameron, Essential Design Considerations for Microporous Implants: Preliminary Communication, *Journal of the Royal Society of Medicine*, Vol./Iss: 74, pp. 887-891, Dec. 1981.
Kang Moo Huh et al., PLGA-PEG Copolymers, <<www.drugdeliverytech.com/cgi-bin/articles.cgi!idArticle=152>>, pp. 1-11.
M. Conley Wake et al., Pore Morphology Effects on the Fibrovascular Tissue Growth in Porous Polymer Substrates, *Cell Transplantation*, Vol./Iss: 3(4), pp. 339-343, 1994.
Macha et al., A Phorbid 20-Homovanilates Induce Apoptosis Through a VRI-Indepndent Mechanism, *Chem. Biol.* pp. 440-447.
Marshall Hicks et al., Intervention Radiology for the Cancer Patient, *Principles of Imaging* pp. 440-447.
Mikos et al., Laminated Three-Dimensional Biodegradable Foams for Use in Tissue Engineering, <<www.ncbi.nlm.nih.gov/entrez/query.fegi?cnd=Retreive&db=pubmed&list_uids=85 . . . >>page Abstract, 1993.
Olah et al., Ligand-induced Dynamic Membrane changes and Cell Deletion Conferred by Vanilloid receptor 1, *The Journal of Biological Chemistry*, Vol./Iss: 276(14), pp. 11021-11030, 2001.

Paul S. Schreuders et al., Norman Wound Healing Compared to Healing with Porous Dacron Implants, *Journal of Biomedical Materials Research*, Vol./Iss: 22(2), pp. 121-135, Feb. 1988.
Peter A.D. Rubin et al., Comparison of Fibrovascular Ingrowth into Hydroxyapatite and Porous Polyethylene Orbital Implants, *Ophthalmic Plastics and Reconstructive Surgery* Vol./Iss: 10(2), pp. 96-103, Nov. 2, 1994.
Peter J. van Mullem et al., Bone and Soft Connective Tissue Response to Prous Acrylic Implants, *J. Cranio-Max. - Fac. Surg.*, Vol./Iss: 16, pp. 99-109, 1988.
Ralph E. Holmes et al., Porous Hydroxyapatite as a Bone Graft substitute in Diaphyseal Defects: A Histomeric Study, *Journal of Orthopaedic Research*, Vol./Iss: 5, pp. 114-121, 1987.
Richard J. Klasa et al., Eradication of Human Non-Hodgkin's Lymphoma in SCID Mice by BCL-2 Antisense Oligonucleotides Combined with Low-Dose cyclophosphamid, *Clinical Cancer Research*, Vol./Iss: 6, pp. 2492-2500, Jun. 2000.
Robert M. Brohim et al., Early Tissue Reaction to Texture Breast Implant Surfaces, *Annals of Plastic Surgery*, Vol./Iss: 28(4), pp. 354-362, Apr. 1992.
Schuber et al., Role of Oxygen in Biodegradation of Poly(etherurethan urea) Elastomers, *Journal of Biomedical Materials Research*, Vol./Iss: 34, pp. 519-530, 1997.
Shoufeng Yang et al., The Design of Scaffolds for Use in Tissue Engineering. Part 1. Traditional Factors, *Tissue Engineering*, Vol./Iss: 7, pp. 679-689, Nov. 6, 2001.
Song et al., Bladder Tissue Pharmacokinetics of Intravesical Taxol, *Cancer Chemother Pharmacol*, Vol./Iss: 40, pp. 285-292, 1997.
Stock et al., Tissue Engineering of Car dac Valves on the Basis of PGA/PLA Co-Polymers <<www.ncbi.nlm.nih.gov/entrez/query.fegi? cmd=Retrieve&db=pubmed&dopt-abstr . . .>>. pp. 1-2, 2001.
Stokes et al., Polyurethane Elastomer Biostahility, *Journal of Biomedical Materials Applications*. Vol./Iss: 9, pp. 321-354, 350, 1995.
Szallasi et al., A Vanilloid (Capsion) Receptors and Mechanisms, *Pharmacol. Rev.* Vol./Iss: 51, p. 159, 1991.
Szallasi et al., A resiniferatoxin-type Phorbid Vanillolds Display Capsaicin-like selectivity at Native Vanilloid receptors on Rat DR6 Neurons and at the cloned Vanilloid Receptor VR1, Vol./Iss: 128(2), pp. 428-434, 1999.
Szycher, Prosthetic and Biomedical Devices, *Encyclopedia of Chemical, Technology 4th ed.*, Vol./Iss: 20, pp. 351-395, 1996.
Vert et al., Biodegradation of PLA/GA Polymers: Increasing Complexity, <<www.ncbi.nlm.nih.gov/entrez/query.fegi?cmd-Retrieve&dbmed&dopt=abstr . . . >>., 1994.
William J. Rashkind et al., Nonsurgical Closure of Patent Ductus Arteriosus: Clinical Application of the Rashkind PDA Occluder System, *Circulation*, Vol./Iss: 75(3), pp. 583-592, Mar. 1987.
Office Action dated Jun. 11, 2009 issued in the U.S. Appl. No. 10/900,982, 11 pages.
Final Office Action dated May 29, 2008 issued in the U.S. Appl. No. 10/900,982, 14 pages.
Final Office Action dated Feb. 8, 2007 issued in the U.S. Appl. No. 10/900,982, 16 pages.
Office Action dated Jul. 26, 2006 issued in the U.S. Appl. No. 10/900,982, 11 pages.
U.S. Appl. No. 10/900,982, filed Jul. 27, 2004, Maybelle Jordan et al.

RETICULATED ELASTOMERIC MATRICES, THEIR MANUFACTURE AND USE IN IMPLANTABLE DEVICES

This application claims the benefit of U.S. provisional application No. 60/471,518, filed May 15, 2003, and International Application no. PCT/US03/33750, filed Oct. 23, 2003, the disclosure of each application being incorporated by reference herein in its entirety.

FIELD OF THE INVENTION

This invention relates to reticulated elastomeric matrices, their manufacture and uses including uses for implantable devices into or for topical treatment of patients, such as humans and other animals, for therapeutic, nutritional, or other useful purposes. For these and other purposes the inventive products may be used alone or may be loaded with one or more deliverable substances.

BACKGROUND OF THE INVENTION

The tissue engineering ("TE") approach generally includes the delivery of a biocompatible tissue substrate that serves as a scaffold or support onto which cells may attach, grow and/or proliferate, thereby synthesizing new tissue by regeneration or new tissue growth to repair a wound or defect. Open cell biocompatible foams have been recognized to have significant potential for use in the repair and regeneration of tissue. However, because of their ability to break down and be absorbed by the body without causing any adverse tissue response during and after the body has synthesized new tissue to repair the wound, prior work in this area has focused on tissue engineering scaffolds made from synthetic bioabsorbable materials.

Several attempts have been made to make bioabsorbable TE scaffolds using various processing methods and materials such as those described in U.S. Pat. No. 5,522,895 (Mikos), U.S. Pat. No. 5,514,378 (Mikos et al.), U.S. Pat. No. 5,133,755 (Brekke), U.S. Pat. No. 5,716,413 (Walter et al.), U.S. Pat. No. 5,607,474 (Athanasiou et al.), U.S. Pat. No. 6,306,424 (Vyakarnam et. al), U.S. Pat. No. 6,355,699 (Vyakarnam et. al), U.S. Pat. No. 5,677,355 (Shalaby et al.), U.S. Pat. No. 5,770,193 (Vacanti et al.), and U.S. Pat. No. 5,769,899 (Schwartz et al.). Synthetic bioabsorbable biocompatible polymers used in the above-mentioned references are well known in the art and, in most cases, include aliphatic polyesters, homopolymers and copolymers (random, block, segmented and graft) of monomers such as glycolic acid, glycolide, lactic acid, lactide (d, 1, meso or a mixture thereof), ε-caprolactone, trimethylene carbonate and p-dioxanone.

The major weaknesses of these approaches relating to bioabsorbable three-dimensional porous scaffolds used for tissue regeneration are undesirable tissue response during the product's life cycle as the polymers biodegrade and the inability to engineer the degradation characteristics of the TE scaffold in vivo, thus severely limiting their ability to serve as effective scaffolds. Also, there remains a need for an implant that withstands compression in a delivery-device during delivery to a biological site, e.g., by a catheter, endoscope, arthoscope or syringe, capable of expansion by resiliently recovering to occupy and remain in the biological site, and of a particular pore size such that the implant can become ingrown with tissue at that site to serve a useful therapeutic purpose. Furthermore, many materials produced from polyurethane foams formed by blowing during the polymerization process are unattractive from the point of view of biodurability because undesirable materials that can produce adverse biological reactions are generated during polymerization, for example, carcinogens, cytotoxins and the like. In contrast, the biodurable reticulated elastomeric matrix materials of the present invention are suitable for such applications as long-term TE implants, especially where dynamic loadings and/or extensions are experienced, such as in soft tissue related orthopedic applications.

A number of polymers having varying degrees of biodurability are known, but commercially available materials either lack the mechanical properties needed to provide an implantable device that can be compressed for delivery-device delivery and can resiliently expand in situ, at the intended biological site, or lack sufficient porosity to induce adequate cellular ingrowth and proliferation. Some proposals of the art are further described below.

Brady et al., in U.S. Pat. No. 6,177,522 ("Brady '522"), disclose implantable porous polycarbonate polyurethane products comprising a polycarbonate that is disclosed to be a random copolymer of alkyl carbonates. Brady '522's crosslinked polymer comprises urea and biuret groups, when urea is present, and urethane and allophanate groups, when urethane is present.

Brady et al., in U.S. Patent Application Publication No. 2002/0072550 A1 ("Brady '550"), disclose implantable porous polyurethane products formed from a polyether or a polycarbonate linear long chain diol. Brady '550 does not broadly disclose a biostable porous polyether or polycarbonate polyurethane implant having a void content in excess of 85%. The diol of Brady '550 is disclosed to be free of tertiary carbon linkages. Additionally, Brady '550's diisocyanate is disclosed to be 4,4'-diphenylmethane diisocyanate containing less than 3% 2,4'-diphenylmethane diisocyanate. Furthermore, the final foamed polyurethane product of Brady '550 contains isocyanurate linkages and is not reticulated.

Brady et al., in U.S. Patent Application Publication No. 2002/0142413 A1 ("Brady '413"), disclose a tissue engineering scaffold for cell, tissue or organ growth or reconstruction, comprising a solvent-extracted, or purified, reticulated polyurethane, e.g. a polyether or a polycarbonate, having a high void content and surface area. Certain embodiments employ a blowing agent during polymerization for void creation. A minimal amount of cell window opening is effected by a hand press or by crushing and solvent extraction is used to remove the resulting residue. Accordingly, Brady '413 does not disclose a resiliently-compressible reticulated product or a process to make it.

Gilson et al., in U.S. Pat. No. 6,245,090 B1 ("Gilson"), disclose an open cell foam transcatheter occluding implant with a porous outer surface said to have good hysteresis properties, i.e., which, when used in a vessel that is continually expanding and contracting, is said to be capable of expanding and contracting faster than the vessel. Gilson's open cell foam is not reticulated.

Pinchuk, in U.S. Pat. Nos. 5,133,742 and 5,229,431 ("Pinchuk '742" and "Pinchuk '431", respectively), discloses a crack-resistant polyurethane said to be useful for medical prostheses, implants, roofing insulators and the like. The polymer is a polycarbonate polyurethane polymer which is substantially completely devoid of ether linkages.

Szycher et al., in U.S. Pat. No. 5,863,627 ("Szycher"), disclose a biocompatible polycarbonate polyurethane with internal polysiloxane segments.

MacGregor, in U.S. Pat. No. 4,459,252, discloses cardiovascular prosthetic devices or implants comprising a porous surface and a network of interconnected interstitial pores below the surface in fluid flow communication with the surface pores.

Gunatillake et al., in U.S. Pat. No. 6,420,452 ("Gunatillake '452"), disclose a degradation resistant silicone-containing elastomeric polyurethane. Gunatillake et al., in U.S. Pat. No. 6,437,073 ("Gunatillake '073"), disclose a degradation-resistant silicone-containing polyurethane which is, furthermore, non-elastomeric.

Pinchuk, in U.S. Pat. No. 5,741,331 ("Pinchuk '331"), and its divisional U.S. Pat. Nos. 6,102,939 and 6,197,240, discloses supposed polycarbonate stability problems of microfiber cracking and breakage. Pinchuk '331 does not disclose a self-supporting, space-occupying porous element having three-dimensional resilient compressibility that can be catheter-, endoscope-, or syringe-introduced, occupy a biological site and permit cellular ingrowth and proliferation into the occupied volume.

Pinchuk et al., in U.S. Patent Application Publication No. 2002/0107330 A1 ("Pinchuk '330"), disclose a composition for implantation delivery of a therapeutic agent which comprises: a biocompatible block copolymer having an elastomeric block, e.g., polyolefin, and a thermoplastic block, e.g., styrene, and a therapeutic agent loaded into the block copolymer. The Pinchuk '330 compositions lack adequate mechanical properties to provide a compressible catheter-, endoscope-, or syringe-introducible, resilient, space-occupying porous element that can occupy a biological site and permit cellular ingrowth and proliferation into the occupied volume.

Tuch, in U.S. Pat. No. 5,820,917, discloses a blood-contacting medical device coated with a layer of water-soluble heparin, overlaid by a porous polymeric coating through which the heparin can elute. The porous polymer coating is prepared by methods such as phase inversion precipitation onto a stent yielding a product with a pore size of about 0.5-10 μm. Tuch's disclosed pore sizes are too small for effective cellular ingrowth and proliferation of uncoated substrates.

The above references do not disclose, e.g., an implantable device that is entirely suitable for delivery-device delivery, resilient recovery from that delivery, and long-term residence as a tissue engineering scaffold with the therapeutic benefits, e.g., tissue repair and regeneration, associated with appropriately-sized interconnected pores. Moreover, the above references do not disclose, e.g., such a device containing polycarbonate moieties.

The foregoing description of background art may include insights, discoveries, understandings or disclosures, or associations together of disclosures, that were not known to the relevant art prior to the present invention but which were provided by the invention. Some such contributions of the invention may have been specifically pointed out herein, whereas other such contributions of the invention will be apparent from their context. Merely because a document may have been cited here, no admission is made that the field of the document, which may be quite different from that of the invention, is analogous to the field or fields of the invention. The citation of any reference in the background section of this application is not an admission that the reference is prior art to the application.

SUMMARY OF THE INVENTION

The implantable devices of the invention are useful for many applications as long-term TE implants, especially where dynamic loadings and/or extensions are experienced, such as in soft tissue related orthopedic applications for repair and regeneration. The implantable devices of the invention are deliverable by a delivery-device, e.g., catheter, endoscope, arthoscope, laproscop, cystoscope or syringe, for long-term residence in a patient, for example a mammal. In one embodiment, the invention provides as an implantable device a biodurable, reticulated, resiliently compressible elastomeric matrix. In another embodiment, the implantable device is biodurable for at least 29 days. In another embodiment, the implantable device is biodurable for at least 2 months. In another embodiment, the implantable device is biodurable for at least 6 months. In another embodiment, the implantable device is biodurable for at least 12 months. In another embodiment, the implantable device is biodurable for longer than 12 months. In another embodiment, the implantable device is biodurable for at least 24 months. In another embodiment, the implantable device is biodurable for at least 5 years. In another embodiment, the implantable device is biodurable for longer than 5 years.

The structure, morphology and properties of the elastomeric matrices of this invention can be engineered or tailored over a wide range of performance by varying the starting materials and/or the processing conditions for different functional or therapeutic uses.

The ability to engineer the properties of an implantable device to complement the tissues that are targeted for repair and/or regeneration provides flexibility and the potential for using the invention described herein in a number of orthopedic applications. An implantable device formed from the biodurable reticulated elastomeric matrix, when used as a TE scaffold in one embodiment, can maintain its physical characteristics and performance in vivo over long periods of time, up to as long as the life of the implantable device. In another embodiment, the implantable device does not initiate undesirable tissue response over long periods of time, up to as long as the life of the implantable device. In another embodiment, a high void content and/or a high degree of reticulation is thought to allow the implantable device to become completely ingrown and proliferated with cells including tissues such as fibroblasts, fibrous tissues, synovial cells, bone marrow stromal cells, stem cells and/or fibrocartilage cells. Such ingrown and proliferated tissue is able to provide functionality, such as load-bearing capability, that the original tissue that is being repaired and/or replaced previously possessed.

In one embodiment, the invention provides an elastomeric matrix having a reticulated structure. In another embodiment, the elastomeric matrix, as it becomes encapsulated and ingrown with cells and/or tissue, can play a less important role. In another embodiment, the encapsulated and ingrown elastomeric matrix occupies only a small amount of space, does not interfere with the function of the regrown cells and/or tissue, and has no tendency to migrate.

The inventive implantable device is reticulated, i.e., comprises an interconnected network of pores, either by being formed having a reticulated structure and/or undergoing a reticulation process. This provides fluid permeability throughout the implantable device and permits cellular ingrowth and proliferation into the interior of the implantable device. For this purpose, in one embodiment relating to orthopedic applications and the like, the reticulated elastomeric matrix has pores with an average diameter or other largest transverse dimension of at least about 20 μm. In another embodiment, the reticulated elastomeric matrix has pores with an average diameter or other largest transverse dimension of from about 20 μm to about 150 μm. In another embodiment, the reticulated elastomeric matrix has pores with an average diameter or other largest transverse dimension of from about 150 μm to about 250 μm. In another embodiment, the reticulated elastomeric matrix has pores with an average diameter or other largest transverse dimension of from about 250 μm to about 500 μm. In another embodiment, the reticulated elastomeric matrix has pores with an average diameter or other largest transverse dimension of from greater than 250 μm to about 600 μm.

In one embodiment, an implantable device comprise a reticulated elastomeric matrix that is flexible and resilient and can recover its shape and most of its size after compression. In another embodiment, the inventive implantable devices have a resilient compressibility that allows the implantable device to be compressed under ambient conditions, e.g., at 25° C., from a relaxed configuration to a first, compact configuration for in vivo delivery via a delivery-device and to expand to a second, working configuration in situ. In another embodiment, the elastomeric matrix 10 expands in dimension from the first, compact configuration to the second, working configuration over a short time, e.g., to recover about 90% of the pre-compression dimension (the dimension before compression is applied along that dimension) in 30 seconds or less in one embodiment, or in 20 seconds or less in another embodiment, each from 75% compression strain held for up to 10 minutes. In another embodiment, the expansion from the first, compact configuration to the second, working configuration occurs over a short time, e.g., about 90% recovery in 120 seconds or less in one embodiment, in 60 seconds or less in another embodiment, in 30 seconds or less in another embodiment, each from 75% compression strain held for up to 30 minutes. In another embodiment, the elastomeric matrix 10 expands from the first, compact configuration to the second, working configuration over a short time, e.g., about 95% recovery in 90 seconds or less in one embodiment, or in 40 seconds or less in another embodiment, each from 75% compression strain held for up to 10 minutes. In another embodiment, the expansion from the first, compact configuration to the second, working configuration occurs over a short time, e.g., about 95% recovery in 180 seconds or less in one embodiment, in 90 seconds or less in another embodiment, in 60 seconds or less in another embodiment, each from 75% compression strain held for up to 30 minutes. In another embodiment, at least one dimension of the second, working configuration is substantially equivalent to, i.e., from about 95% to about 105% of, the corresponding dimension of the implantable device's relaxed configuration. In another embodiment, the dimensions of the second, working configuration are substantially equivalent to the corresponding dimensions of the implantable device's relaxed configuration.

The present invention can provide truly reticulated, flexible, resilient, biodurable elastomeric matrix, suitable for long-term implantation and having sufficient porosity to encourage cellular ingrowth and proliferation, in vivo.

In another embodiment, the invention provides a process for producing a biodurable, flexible, reticulated, resiliently-compressible elastomeric matrix, suitable for implantation into patients, the process comprising forming interconnected pores in a biodurable elastomer by a process free of undesirable residuals to yield an elastomeric matrix having a reticulated structure that, when implanted in a patient, is biodurable for at least 29 days and has porosity providing fluid permeability throughout the elastomeric matrix and permitting cellular ingrowth and proliferation into the interior of the elastomeric matrix.

In another embodiment, the process is conducted to provide an elastomeric matrix configuration allowing cellular ingrowth and proliferation into the interior of the elastomeric matrix and the elastomeric matrix is implantable into a patient, as described herein. Without being bound by any particular theory, having a high void content and a high degree of reticulation is thought to allow the implantable devices to be completely ingrown and proliferated with cells including tissues such as fibrous tissues.

Reticulated elastomers may be adequate for many applications for longer-term implantable devices especially in cases where dynamic loadings or extensions are experienced. The ability to engineer the properties to match the tissues that are being targeted for repair and regeneration can, provide tremendous flexibility and potential for using the inventions described here in a number of orthopedic applications. The reticulated elastomeric matrix when used as a scaffold maintains its physical characteristics and performance in vivo over longer periods of time and in fact during the life of the implantable device. Thus it does not initiate undesirable tissue response during the product's life cycle.

The ingrown and proliferated tissues thereby provide functionality, such as load bearing capability, of the original tissue that is being repaired or replaced.

In another embodiment, the invention provides a polymerization process for preparing a reticulated elastomeric matrix, the process comprising admixing:
  a) a polyol component,
  b) an isocyanate component,
  c) a blowing agent,
  d) optionally, a crosslinking agent,
  e) optionally, a chain extender,
  f) optionally, at least one catalyst,
  g) optionally, at least one cell opener,
  h) optionally, a surfactant, and
  i) optionally, a viscosity modifier;

to provide a crosslinked elastomeric matrix and reticulating the elastomeric matrix by a reticulation process to provide the reticulated elastomeric matrix. The ingredients are present in quantities and the elastomeric matrix is prepared and under conditions to (i) provide a crosslinked resiliently-compressible biodurable elastomeric matrix, (ii) control formation of biologically undesirable residues, and (iii) reticulate the foam by a reticulation process, to provide the reticulated elastomeric matrix.

In another embodiment, the invention provides a lyophilization process for preparing a reticulated elastomeric matrix comprising lyophilizing a flowable polymeric material. In another embodiment, the polymeric material comprises a solution of a solvent-soluble biodurable elastomer in a solvent. In another embodiment, the flowable polymeric material is subjected to a lyophilization process comprising solidifying the flowable polymeric material to form a solid, e.g., by cooling a solution, then removing the non-polymeric material, e.g., by subliming the solvent from the solid under reduced pressure, to provide an at least partially reticulated elastomeric matrix. In another embodiment, a solution of a biodurable elastomer in a solvent is substantially, but not necessarily completely, solidified, then the solvent is sublimed from that material to provide an at least partially reticulated elastomeric matrix. In another embodiment, the temperature to which the solution is cooled is below the freezing temperature of the solution. In another embodiment, the temperature to which the solution is cooled is above the apparent glass transition temperature of the solid and below the freezing temperature of the solution.

In another embodiment, the invention provides a lyophilization process for producing an elastomeric matrix having a reticulated structure, the process comprising:
  a) forming a solution comprising a solvent-soluble biodurable elastomer in a solvent;

b) at least partially solidifying the solution to form a solid, optionally by cooling the solution; and c) removing the non-polymeric material, optionally by subliming the solvent from the solid under reduced pressure, to provide an at least partially reticulated elastomeric matrix comprising the elastomer.

In another embodiment, the invention provides a process for preparing a reticulated composite elastomeric implantable device for implantation into a patient, the process comprising surface coating or endoporously coating a biodurable reticulated elastomeric matrix with a coating material selected to encourage cellular ingrowth and proliferation. The coating material can, for example, comprise a foamed coating of a biodegradable material, optionally, collagen, fibronectin, elastin, hyaluronic acid or a mixture thereof. Alternatively, the coating comprises a biodegradable polymer and an inorganic component.

In another embodiment, the invention provides a process for preparing a reticulated composite elastomeric implantable device useful for implantation into a patient, the process comprising surface coating or endoporously coating or impregnating a reticulated biodurable elastomer. This coating or impregnating material can, for example, comprise polyglycolic acid ("PGA"), polylactic acid ("PLA"), polycaprolactic acid ("PCL"), poly-p-dioxanone ("PDO"), PGA/PLA copolymers, PGA/PCL copolymers, PGA/PDO copolymers, PLA/PCL copolymers, PLA/PDO copolymers, PCL/PDO copolymers or combinations of any two or more of the foregoing. Another embodiment involves surface coating or surface fusion, wherein the porosity of the surface is altered.

In another embodiment, the invention provides a method for treating an orthopedic disorder in a patient, such as an animal, the method comprising:

a) compressing the herein-described inventive implantable device from a relaxed configuration to a first, compact configuration;

b) delivering the compressed implantable device to the in vivo site of the orthopedic disorder via a delivery-device; and c) allowing the implantable device to resiliently recover and expand to a second, working configuration at the in vivo site.

In another embodiment, the inventive implantable device is inserted by an open surgical procedure.

In another embodiment, the invention provides a method for treating an orthopedic disorder in a patient comprising delivering the inventive implantable device to the in vivo site of the orthopedic disorder with negligible or no compaction of the implantable device, e.g., about 90% or greater recovery in 120 seconds or less in one embodiment, in 75 seconds or less in another embodiment, in 60 seconds or less in another embodiment, in 30 seconds or less in another embodiment, each from 75% compression strain held for up to 30 minutes.

In another embodiment, the implantable device made from biodurable reticulated elastomeric matrix provides a method for treating so-called hard-tissue disorders, e.g., maxillofacial or cranial tissue disorders. In another embodiment, the implantable device made from biodurable reticulated elastomeric matrix provides a method for treating so-called soft-tissue disorders, e.g., tendon augmentation, repair of articular cartilage, meniscal repair and reconstruction, anterior cruciate ligament reconstruction, stabilization of a herniated disc, scaffolds for nucleus replacement, and scaffolds for annulus repair.

In another embodiment, the implantable device made from biodurable reticulated elastomeric matrix can be seeded with a type of cell and cultured before being inserted into the patient, optionally using a delivery-device. In another embodiment, the implantable device is placed into a patient's tissue repair and regeneration site after being subjected to in vitro cell culturing.

BRIEF DESCRIPTION OF THE DRAWINGS

Some embodiments of the invention, and of making and using the invention, are described in detail below, which description is to be read with and in the light of the foregoing description, by way of example, with reference to the accompanying drawings, in which like reference characters designate the same or similar elements throughout the several views, and in which.

DETAILED DESCRIPTION OF THE INVENTION

Figure 1:
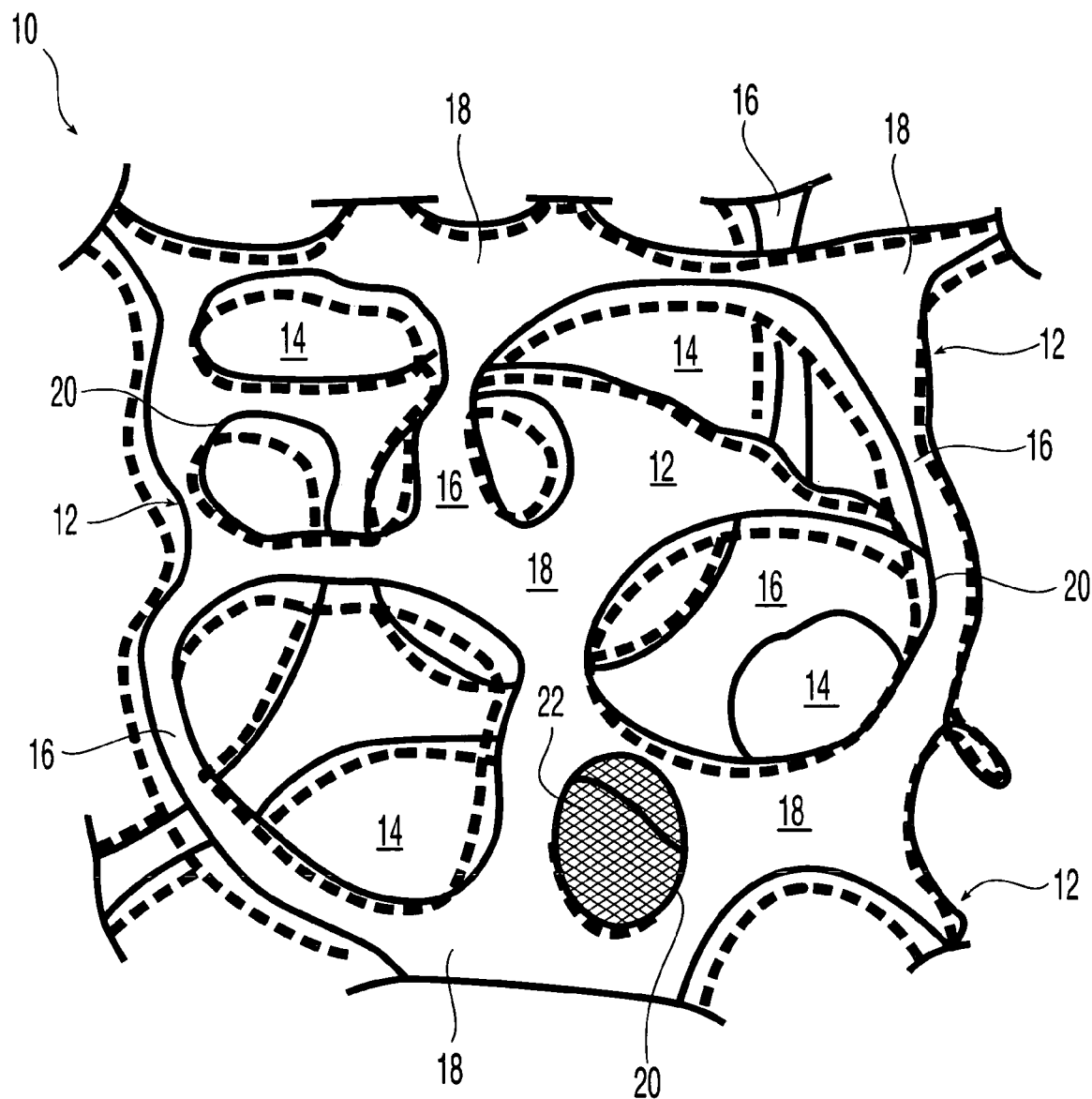
FIG. 1 is a schematic view showing one possible morphology for a portion of the microstructure of one embodiment of a porous biodurable elastomeric product according to the invention.

Certain embodiments of the invention comprise reticulated biodurable elastomer products, which are also compressible and exhibit resilience in their recovery, that have a diversity of applications and can be employed, by way of example, in biological implantation, especially into humans, for long-term TE implants, especially where dynamic loadings and/or extensions are experienced, such as in soft tissue related orthopedic applications; for tissue augmentation, support and repair; for therapeutic purposes; for cosmetic, reconstructive, urologic or gastroesophageal purposes; or as substrates for pharmaceutically-active agent, e.g., drug, delivery. Other embodiments involve reticulated biodurable elastomer products for in vivo delivery via catheter, endoscope, arthoscope, laproscop, cystoscope, syringe or other suitable delivery-device and can be satisfactorily implanted or otherwise exposed to living tissue and fluids for extended periods of time, for example, at least 29 days.

There is a need in medicine, as recognized by the present invention, for innocuous implantable devices that can be delivered to an in vivo patient site, for example a site in a human patient, that can occupy that site for extended periods of time without being harmful to the host. In one embodiment, such implantable devices can also eventually become integrated, e.g., ingrown with tissue. Various biodegradable porous polymeric materials have been proposed for tissue augmentation and repair.

It would be desirable to form implantable devices suitable for use as tissue engineering scaffolds, or other comparable substrates, to support in vivo cell propagation applications, for example in a large number of orthopedic applications especially in soft tissue attachment, regeneration, augmentation, support and ingrowth of a prosthetic organ. Without being bound by any particular theory, having a high void content and a high degree of reticulation is thought to allow the implantable device to become at least partially ingrown and/or proliferated, in some cases substantially ingrown and proliferated, in some cases completely ingrown and proliferated, with cells including tissues such as fibroblasts, fibrous tissues, synovial cells, bone marrow stromal cells, stem cells and/or fibrocartilage cells. The ingrown and/or proliferated tissues thereby provide functionality, such as load bearing capability, of the original tissue that is being repaired or replaced. However, prior to the advent of the present invention, materials and/or products meeting the requirements for such implantable devices have not been available.

Broadly stated, certain embodiments of the reticulated biodurable elastomeric products of the invention comprise, or are largely if not entirely, constituted by a highly permeable, reticulated matrix formed of a biodurable polymeric elastomer that is resiliently-compressible so as to regain its shape after delivery to a biological site. In one embodiment, the elastomeric matrix is chemically well-characterized. In another embodiment, the elastomeric matrix is physically well-characterized. In another embodiment, the elastomeric matrix is chemically and physically well-characterized.

Certain embodiments of the invention can support cell growth and permit cellular ingrowth and proliferation in vivo and are useful as in vivo biological implantable devices, for example, for tissue engineering scaffolds that may be used in vitro or in vivo to provide a substrate for cellular propagation.

In one embodiment, the reticulated elastomeric matrix of the invention facilitates tissue ingrowth by providing a surface for cellular attachment, migration, proliferation and/or coating (e.g., collagen) deposition. In another embodiment, any type of tissue can grow into an implantable device comprising a reticulated elastomeric matrix of the invention, including, by way of example, epithelial tissue (which includes, e.g., squamous, cuboidal and columnar epithelial tissue), connective tissue (which includes, e.g., areolar tissue, dense regular and irregular tissue, reticular tissue, adipose tissue, cartilage and bone), and muscle tissue (which includes, e.g., skeletal, smooth and cardiac muscle), or any combination thereof, e.g., fibrovascular tissue. In another embodiment of the invention, an implantable device comprising a reticulated elastomeric matrix of the invention can have tissue ingrowth substantially throughout the volume of its interconnected pores.

In one embodiment, the invention comprises an implantable device having sufficient resilient compressibility to be delivered by a "delivery-device", i.e., a device with a chamber for containing an elastomeric implantable device while it is delivered to the desired site then released at the site, e.g., using a catheter, endoscope, arthoscope, laproscope, cystoscope or syringe. In another embodiment, the thus-delivered elastomeric implantable device substantially regains its shape after delivery to a biological site and has adequate biodurability and biocompatibility characteristics to be suitable for long-term implantation.

The structure, morphology and properties of the elastomeric matrices of this invention can be engineered or tailored over a wide range of performance by varying the starting materials and/or the processing conditions for different functional or therapeutic uses.

Without being bound by any particular theory, it is thought that an aim of the invention, to provide a light-weight, durable structure that can fill a biological volume or cavity and containing sufficient porosity distributed throughout the volume, can be fulfilled by permitting one or more of: occlusion, embolization, cellular ingrowth, cellular proliferation, tissue regeneration, cellular attachment, drug delivery, enzymatic action by immobilized enzymes, and other useful processes as described herein including, in particular, the applications to which priority is claimed.

In one embodiment, elastomeric matrices of the invention have sufficient resilience to allow substantial recovery, e.g., to at least about 50% of the size of the relaxed configuration in at least one dimension, after being compressed for implantation in the human body, for example, a low compression set, e.g., at 25° C. or 37° C., and sufficient strength and flow-through for the matrix to be used for controlled release of pharmaceutically-active agents, such as a drug, and for other medical applications. In another embodiment, elastomeric matrices of the invention have sufficient resilience to allow recovery to at least about 60% of the size of the relaxed configuration in at least one dimension after being compressed for implantation in the human body. In another embodiment, elastomeric matrices of the invention have sufficient resilience to allow recovery to at least about 90% of the size of the relaxed configuration in at least one dimension after being compressed for implantation in the human body.

In the present application, the term "biodurable" describes elastomers and other products that are stable for extended periods of time in a biological environment. Such products should not exhibit significant symptoms of breakdown or degradation, erosion or significant deterioration of mechanical properties relevant to their employment when exposed to biological environments for periods of time commensurate with the use of the implantable device. The period of implantation may be weeks, months or years; the lifetime of a host product in which the elastomeric products of the invention are incorporated, such as a graft or prosthetic; or the lifetime of a patient host to the elastomeric product. In one embodiment, the desired period of exposure is to be understood to be at least about 29 days. In another embodiment, the desired period of exposure is to be understood to be at least 29 days. In one embodiment, the implantable device is biodurable for at least 2 months. In another embodiment, the implantable device is biodurable for at least 6 months. In another embodiment, the implantable device is biodurable for at least 12 months. In another embodiment, the implantable device is biodurable for longer than 12 months. In another embodiment, the implantable device is biodurable for at least 24 months. In another embodiment, the implantable device is biodurable for at least 5 years. In another embodiment, the implantable device is biodurable for longer than 5 years.

In one embodiment, biodurable products of the invention are also biocompatible. In the present application, the term "biocompatible" means that the product induces few, if any, adverse biological reactions when implanted in a host patient. Similar considerations applicable to "biodurable" also apply to the property of "biocompatibility".

An intended biological environment can be understood to in vivo, e.g., that of a patient host into which the product is implanted or to which the product is topically applied, for example, a mammalian host such as a human being or other primate, a pet or sports animal, a livestock or food animal, or a laboratory animal. All such uses are contemplated as being within the scope of the invention. As used herein, a "patient" is an animal. In one embodiment, the animal is a bird, including but not limited to a chicken, turkey, duck, goose or quail, or a mammal. In another embodiment, the animal is a mammal, including but not limited to a cow, horse, sheep, goat, pig, cat, dog, mouse, rat, hamster, rabbit, guinea pig, monkey and a human. In another embodiment, the animal is a primate or a human. In another embodiment, the animal is a human.

In one embodiment, structural materials for the inventive porous elastomers are synthetic polymers, especially but not exclusively, elastomeric polymers that are resistant to biological degradation, for example, in one embodiment, polycarbonate polyurethanes, polycarbonate urea-urethanes, polyether polyurethanes, poly(carbonate-co-ether)urea-urethanes, polysiloxanes and the like, in another embodiment polycarbonate urea-urethanes, poly(carbonate-co-ether) urea-urethanes and polysiloxanes. Such elastomers are generally hydrophobic but, pursuant to the invention, may be treated to have surfaces that are less hydrophobic or somewhat hydrophilic. In another embodiment, such elastomers may be produced with surfaces that are less hydrophobic or somewhat hydrophilic.

The reticulated biodurable elastomeric products of the invention can be described as having a "macrostructure" and a "microstructure", which terms are used herein in the general senses described in the following paragraphs.

The "macrostructure" refers to the overall physical characteristics of an article or object formed of the biodurable elastomeric product of the invention, such as: the outer periphery as described by the geometric limits of the article or object, ignoring the pores or voids; the "macrostructural surface area" which references the outermost surface areas as though any pores thereon were filled, ignoring the surface areas within the pores; the "macrostructural volume" or simply the "volume" occupied by the article or object which is the volume bounded by the macrostructural, or simply "macro", surface area; and the "bulk density" which is the weight per unit volume of the article or object itself as distinct from the density of the structural material.

The "microstructure" refers to the features of the interior structure of the biodurable elastomeric material from which the inventive products are constituted such as pore dimensions; pore surface area, being the total area of the material surfaces in the pores; and the configuration of the struts and intersections that constitute the solid structure of certain embodiments of the inventive elastomeric product.

Referring to FIG. 1, what is shown for convenience is a schematic depiction of the particular morphology of a reticulated foam. FIG. 1 is a convenient way of illustrating some of the features and principles of the microstructure of some embodiments of the invention. This figure is not intended to be an idealized depiction of an embodiment of, nor is it a detailed rendering of a particular embodiment of the elastomeric products of the invention. Other features and principles of the microstructure will be apparent from the present specification, or will be apparent from one or more of the inventive processes for manufacturing porous elastomeric products that are described herein.

Morphology

Described generally, the microstructure of the illustrated porous biodurable elastomeric matrix 10, which may, inter alia, be an individual element having a distinct shape or an extended, continuous or amorphous entity, comprises a reticulated solid phase 12 formed of a suitable biodurable elastomeric material and interspersed therewithin, or defined thereby, a continuous interconnected void phase 14, the latter being a principle feature of a reticulated structure.

In one embodiment, the elastomeric material of which elastomeric matrix 10 is constituted may be a mixture or blend of multiple materials. In another embodiment, the elastomeric material is a single synthetic polymeric elastomer such as will be described in more detail below.

Void phase 14 will usually be air- or gas-filled prior to use. During use, void phase 14 will in many but not all cases become filled with liquid, for example, with biological fluids or body fluids.

Solid phase 12 of elastomeric matrix 10, as shown in FIG. 1, has an organic structure and comprises a multiplicity of relatively thin struts 16 that extend between and interconnect a number of intersections 18. The intersections 18 are substantial structural locations where three or more struts 16 meet one another. Four or five or more struts 16 may be seen to meet at an intersection 18 or at a location where two intersections 18 can be seen to merge into one another. In one embodiment, struts 16 extend in a three-dimensional manner between intersections 18 above and below the plane of the paper, favoring no particular plane. Thus, any given strut 16 may extend from an intersection 18 in any direction relative to other struts 16 that join at that intersection 18. Struts 16 and intersections 18 may have generally curved shapes and define between them a multitude of pores 20 or interstitial spaces in solid phase 12. Struts 16 and intersections 18 form an interconnected, continuous solid phase.

As illustrated in FIG. 1, the structural components of the solid phase 12 of elastomeric matrix 10, namely struts 16 and intersections 18, may appear to have a somewhat laminar configuration as though some were cut from a single sheet, it will be understood that this appearance may in part be attributed to the difficulties of representing complex three-dimensional structures in a two dimensional figure. Struts 16 and intersections 18 may have, and in many cases will have, non-laminar shapes including circular, elliptical and non-circular cross-sectional shapes and cross sections that may vary in area along the particular structure, for example, they may taper to smaller and/or larger cross sections while traversing along their longest dimension.

A small number of pores 20 may have a cell wall of structural material also called a "window" or "window pane" such as cell wall 22. Such cell walls are undesirable to the extent that they obstruct the passage of fluid and/or propagation and proliferation of tissues through pores 20. Cell walls 22 may, in one embodiment, be removed in a suitable process step, such as reticulation as discussed below.

Except for boundary terminations at the macrostructural surface, in the embodiment shown in FIG. 1 solid phase 12 of elastomeric matrix 10 comprises few, if any, free-ended, dead-ended or projecting "strut-like" structures extending from struts 16 or intersections 18 but not connected to another strut or intersection.

However, in an alternative embodiment, solid phase 12 can be provided with a plurality of such fibrils (not shown), e.g., from about 1 to about 5 fibrils per strut 16 or intersection 18. In some applications, such fibrils may be useful, for example, for the additional surface area they provide.

Struts 16 and intersections 18 can be considered to define the shape and configuration of the pores 20 that make up void phase 14 (or vice versa). Many of pores 20, in so far as they may be discretely identified, open into and communicate, by the at least partial absence of cell walls 22, with at least two other pores 20. At intersections 18, three or more pores 20 may be considered to meet and intercommunicate. In certain embodiments, void phase 14 is continuous or substantially continuous throughout elastomeric matrix 10, meaning that there are few if any closed cell pores. Such closed cell pores, the interior volume of each of which has no communication with any other cell, e.g., is isolated from an adjacent cells by cell walls 22, represent loss of useful volume and may obstruct access of useful fluids to interior strut and intersection structures 16 and 18 of elastomeric matrix 10.

In one embodiment, closed cell pores, if present, comprise less than about 30% of the volume of elastomeric matrix 10. In another embodiment, closed cell pores, if present, comprise less than about 25% of the volume of elastomeric matrix 10. In another embodiment, closed cell pores, if present, comprise less than about 20% of the volume of elastomeric matrix 10. In another embodiment, closed cell pores, if present, comprise less than about 15% of the volume of elastomeric matrix 10. In another embodiment, closed cell pores, if present, comprise less than about 10% of the volume of elastomeric matrix 10. In another embodiment, closed cell pores, if present, comprise less than about 5% of the volume of elastomeric matrix 10. In another embodiment, closed cell pores, if present, comprise less than about 2% of the volume of elastomeric matrix 10. The presence of closed cell pores can be noted by their influence in reducing the volumetric flow rate of a fluid through elastomeric matrix 10 and/or as a reduction in cellular ingrowth and proliferation into elastomeric matrix 10.

In another embodiment, elastomeric matrix 10 is reticulated. In another embodiment, elastomeric matrix 10 is substantially reticulated. In another embodiment, elastomeric matrix 10 is fully reticulated. In another embodiment, elastomeric matrix 10 has many cell walls 22 removed. In another embodiment, elastomeric matrix 10 has most cell walls 22 removed. In another embodiment, elastomeric matrix 10 has substantially all cell walls 22 removed.

In another embodiment, solid phase 12, which may be described as reticulated, comprises a continuous network of solid structures, such as struts 16 and intersections 18, without any significant terminations, isolated zones or discontinuities, other than at the boundaries of the elastomeric matrix, in which network a hypothetical line may be traced entirely through the material of solid phase 12 from one point in the network to any other point in the network.

In another embodiment, void phase 14 is also a continuous network of interstitial spaces, or intercommunicating fluid passageways for gases or liquids, which fluid passageways extend throughout and are defined by (or define) the structure of solid phase 12 of elastomeric matrix 10 and open into all its exterior surfaces. In other embodiments, as described above, there are only a few, substantially no, or no occlusions or closed cell pores that do not communicate with at least one other pore 20 in the void network. Also in this void phase network, a hypothetical line may be traced entirely through void phase 14 from one point in the network to any other point in the network.

In concert with the objectives of the invention, in one embodiment the microstructure of elastomeric matrix 10 is constructed to permit or encourage cellular adhesion to the surfaces of solid phase 12, neointima formation thereon and cellular and tissue ingrowth and proliferation into pores 20 of void phase 14, when elastomeric matrix 10 resides in suitable in vivo locations for a period of time.

In another embodiment, such cellular or tissue ingrowth and proliferation, which may for some purposes include fibrosis, can occur or be encouraged not just into exterior layers of pores 20, but into the deepest interior of and throughout elastomeric matrix 10. Thus, in this embodiment, the space occupied by elastomeric matrix 10 becomes entirely filled by the cellular and tissue ingrowth and proliferation in the form of fibrotic, scar or other tissue except for the space occupied by the elastomeric solid phase 12. In another embodiment, the inventive implantable device functions so that ingrown tissue is kept vital, for example, by the prolonged presence of a supportive microvasculature.

To this end, particularly with regard to the morphology of void phase 14, in one embodiment elastomeric matrix 10 is reticulated with open interconnected pores. Without being bound by any particular theory, this is thought to permit natural irrigation of the interior of elastomeric matrix 10 with bodily fluids, e.g., blood, even after a cellular population has become resident in the interior of elastomeric matrix 10 so as to sustain that population by supplying nutrients thereto and removing waste products therefrom. In another embodiment, elastomeric matrix 10 is reticulated with open interconnected pores of a particular size range. In another embodiment, elastomeric matrix 10 is reticulated with open interconnected pores with a distribution of size ranges.

It is intended that the various physical and chemical parameters of elastomeric matrix 10 including in particular the parameters to be described below, be selected to encourage cellular ingrowth and proliferation according to the particular application for which an elastomeric matrix 10 is intended.

It will be understood that such constructions of elastomeric matrix 10 that provide interior cellular irrigation will be fluid permeable and may also provide fluid access through and to the interior of the matrix for purposes other than cellular irrigation, for example, for elution of pharmaceutically-active agents, e.g., a drug, or other biologically useful materials. Such materials may optionally be secured to the interior surfaces of elastomeric matrix 10.

In another embodiment of the invention, gaseous phase 12 can be filled or contacted with a deliverable treatment gas, for example, a sterilant such as ozone or a wound healant such as nitric oxide, provided that the macrostructural surfaces are sealed, for example by a bioabsorbable membrane to contain the gas within the implanted product until the membrane erodes releasing the gas to provide a local therapeutic or other effect.

Useful embodiments of the invention include structures that are somewhat randomized, as shown in FIG. 1 where the shapes and sizes of struts 16, intersections 18 and pores 20 vary substantially, and more ordered structures which also exhibit the described features of three-dimensional interpenetration of solid and void phases, structural complexity and high fluid permeability. Such more ordered structures can be produced by the processes of the invention as will be further described below.

Porosity

Void phase 14 may comprise as little as 50% by volume of elastomeric matrix 10, referring to the volume provided by the interstitial spaces of elastomeric matrix 10 before any optional interior pore surface coating or layering is applied. In one embodiment, the volume of void phase 14, as just defined, is from about 70% to about 99% of the volume of elastomeric matrix 10. In another embodiment, the volume of void phase 14 is from about 80% to about 98% of the volume of elastomeric matrix 10. In another embodiment, the volume of void phase 14 is from about 90% to about 98% of the volume of elastomeric matrix 10.

As used herein, when a pore is spherical or substantially spherical, its largest transverse dimension is equivalent to the diameter of the pore. When a pore is non-spherical, for example, ellipsoidal or tetrahedral, its largest transverse dimension is equivalent to the greatest distance within the pore from one pore surface to another, e.g., the major axis length for an ellipsoidal pore or the length of the longest side for a tetrahedral pore. As used herein, the "average diameter or other largest transverse dimension" refers to the number average diameter, for spherical or substantially spherical pores, or to the number average largest transverse dimension, for non-spherical pores.

In one embodiment relating to orthopedic applications and the like, to encourage cellular ingrowth and proliferation and to provide adequate fluid permeability, the average diameter or other largest transverse dimension of pores 20 is at least about 10 μm. In another embodiment, the average diameter or other largest transverse dimension of pores 20 is at least about 20 μm. In another embodiment, the average diameter or other largest transverse dimension of pores 20 is at least about 50 μm. In another embodiment, the average diameter or other largest transverse dimension of pores 20 is at least about 150 μm. In another embodiment, the average diameter or other largest transverse dimension of pores 20 is at least about 250 μm. In another embodiment, the average diameter or other largest transverse dimension of pores 20 is greater than about 250 μm. In another embodiment, the average diameter or other largest transverse dimension of pores 20 is greater than 250 μm. In another embodiment, the average diameter or other largest transverse dimension of pores 20 is at least about 450 μm. In another embodiment, the average diameter or other largest transverse dimension of pores 20 is greater than about 450 μm. In another embodiment, the average diameter or other largest transverse dimension of pores 20 is greater than 450 μm. In another embodiment, the average diameter or other largest transverse dimension of pores 20 is at least about 500 μm.

In another embodiment relating to orthopedic applications and the like, the average diameter or other largest transverse dimension of pores 20 is not greater than about 600 μm. In another embodiment, the average diameter or other largest transverse dimension of pores 20 is not greater than about 450 μm. In another embodiment, the average diameter or other largest transverse dimension of pores 20 is not greater than about 250 μm. In another embodiment, the average diameter or other largest transverse dimension of pores 20 is not greater than about 150 μm. In another embodiment, the average diameter or other largest transverse dimension of pores 20 is not greater than about 20 μm.

In another embodiment relating to orthopedic applications and the like, the average diameter or other largest transverse dimension of pores 20 is from about 10 μm to about 50 μm. In another embodiment, the average diameter or other largest transverse dimension of pores 20 is from about 20 μm to about 150 μm. In another embodiment, the average diameter or other largest transverse dimension of pores 20 is from about 150 μm to about 250 μm. In another embodiment, the average diameter or other largest transverse dimension of pores 20 is from about 250 μm to about 500 μm. In another embodiment, the average diameter or other largest transverse dimension of pores 20 is from about 450 μm to about 600 μm. In another embodiment, the average diameter or other largest transverse dimension of pores 20 is from about 10 μm to about 500 μm. In another embodiment, the average diameter or other largest transverse dimension of pores 10 is from about 20 μm to about 600 μm.

In another embodiment, an implantable device made from elastomeric matrix 10 may comprise pore sizes that vary from small, e.g., 20 μm, to large, e.g., 500 μm, in a single device. In another embodiment, such a variation may occur across the cross-section of the entire material or across any sub-section of a cross-section. In another embodiment, such a variation occurs in a systematic gradual transition. In another embodiment, such a variation occurs in a stepwise manner. For example, the pore size distribution can be from about 20 μm to about 70 μm on one end of an implantable device and be from about 300 μm to about 500 μm on another end of the device. This change in pore size distribution can take place in one or more continuous transitions or in one or more discrete steps. Such variations in pore size distribution result in continuous transition zones or in discrete steps, i.e., the transition from one pore size distribution to another may be more gradual in the case of a continuous transition or transitions but more distinct in the case of a discrete step or steps. With regard to pore orientation, similar transitions may occur in the orientation of the pores, with more oriented pores transitioning into less oriented pores or even into pores substantially devoid of orientation across the cross-section or across a sub-section of the cross-section. The difference in the pore size distribution and/or orientation of the pores across a cross-section of implantable devices made from elastomeric matrix 10 may allow the device to be engineered for preferential behavior in terms of cell type, cell attachment, cell ingrowth and/or cell proliferation. Alternatively, different pore size distribution and/or orientation of the pores across the cross-section of implantable devices made from elastomeric matrix 10 may allow the device to be engineered for preferential behavior in terms of tissue type, tissue attachment, tissue ingrowth and/or tissue proliferation.

It is well known that cells will adhere, proliferate and differentiate along and through the contours of the structure formed by the pore size distribution. The cell orientation and cell morphology will result in engineered or newly-formed tissue that may substantially replicate or mimic the anatomical features of real tissues, e.g., of the tissues being replaced. This preferential cell morphology and orientation ascribed to the continuous or step-wise pore size distribution variations, with or without pore orientation, can occur when the implantable device is placed, without prior cell seeding, into the tissue repair and regeneration site. This preferential cell morphology and orientation ascribed to the continuous or step-wise pore size distribution can also occur when the implantable device is placed into a patient, e.g., human or animal, tissue repair and regeneration site after being subjected to in vitro cell culturing. These continuous or step-wise pore size distribution variations, with or without pore orientation, can be important characteristics for TE scaffolds in a number of orthopedic applications, especially in soft tissue attachment, repair, regeneration, augmentation and/or support encompassing the spine, shoulder, knee, hand or joints, and in the growth of a prosthetic organ.

Pore size, pore size distribution, surface area, gas permeability and liquid permeability can be measured by conventional methods known to those in the art. Some measurement methods are summarized, e.g., by A. Jena and K. Gupta in "Advanced Technology for Evaluation of Pore Structure Characteristics of Filtration Media to Optimize Their Design and Performance", available at www.pmjapp.com/papers/index.html, and in the publication "A Novel Mercury Free Technique for Determination of Pore Volume, Pore Size and Liquid Permeability." Apparatus that can be used to conduct such determinations includes the Capillary Flow Porometer and the Liquid Extrusion Porosimeter, each available from Porous Materials, Inc. (Ithaca, N.Y.).

Size and Shape

Elastomeric matrix 10 can be readily fabricated in any desired size and shape. It is a benefit of the invention that elastomeric matrix 10 is suitable for mass production from bulk stock by subdividing such bulk stock, e.g., by cutting, die punching, laser slicing, or compression molding. In one embodiment, subdividing the bulk stock can be done using a heated surface. It is a further benefit of the invention that the shape and configuration of elastomeric matrix 10 may vary widely and can readily be adapted to desired anatomical morphologies.

The size, shape, configuration and other related details of elastomeric matrix 10 can be either customized to a particular application or patient or standardized for mass production. However, economic considerations favor standardization. To this end, elastomeric matrix 10 can be embodied in a kit comprising elastomeric implantable device pieces of different sizes and shapes. Also, as discussed elsewhere in the present specification and as is disclosed in the applications to which priority is claimed, multiple, e.g. two, three or four, individual elastomeric matrices 10 can be used as an implantable device system for a single target biological site, being sized or shaped or both sized and shaped to function cooperatively for treatment of an individual target site.

The practitioner performing the procedure, who may be a surgeon or other medical or veterinary practitioner, researcher or the like, may then choose one or more implantable devices from the available range to use for a specific treatment, for example, as is described in the applications to which priority is claimed.

By way of example, the minimum dimension of elastomeric matrix 10 may be as little as 0.5 mm and the maximum dimension as much as 100 mm or even greater. However, in one embodiment it is contemplated that an elastomeric matrix 10 of such dimension intended for implantation would have an elongated shape, such as the shapes of cylinders, rods, tubes or elongated prismatic forms, or a folded, coiled, helical or other more compact configuration. Comparably, a dimension as small as 0.5 mm can be a transverse dimension of an elongated shape or of a ribbon or sheet-like implantable device.

In an alternative embodiment, an elastomeric matrix 10 having a spherical, cubical, tetrahedral, toroidal or other form having no dimension substantially elongated when compared to any other dimension and with a diameter or other maximum dimension of from about 0.5 mm to about 500 mm may have utility, for example, for an orthopedic application site. In another embodiment, the elastomeric matrix 10 having such a form has a diameter or other maximum dimension from about 3 mm to about 20 mm.

For most implantable device applications, macrostructural sizes of elastomeric matrix 10 include the following embodiments: compact shapes such as spheres, cubes, pyramids, tetrahedrons, cones, cylinders, trapezoids, parallelepipeds, ellipsoids, fusiforms, tubes or sleeves, and many less regular shapes having transverse dimensions of from about 1 mm to about 200 mm (In another embodiment, these transverse dimensions are from about 5 mm to about 100 mm.); and sheet- or strip-like shapes having a thickness of from about 0.5 to about 20 mm (In another embodiment, these thickness are from about 1 to about 5 mm.) and lateral dimensions of from about 5 to about 200 mm (In another embodiment, these, lateral dimensions are from about 10 to about 100 mm.).

For treatment of orthopedic applications, it is an advantage of the invention that the implantable elastomeric matrix elements can be effectively employed without any need to closely conform to the configuration of the orthopedic application site, which may often be complex and difficult to model. Thus, in one embodiment, the implantable elastomeric matrix elements of the invention have significantly different and simpler configurations, for example, as described in the applications to which priority is claimed.

Furthermore, in one embodiment, the implantable device of the present invention, or implantable devices if more than one is used, should not completely fill the orthopedic application site even when fully expanded in situ. In one embodiment, the fully expanded implantable device(s) of the present invention are smaller in a dimension than the orthopedic application site and provide sufficient space within the orthopedic application site to ensure vascularization, cellular ingrowth and proliferation, and for possible passage of blood to the implantable device. In another embodiment, the fully expanded implantable device(s) of the present invention are substantially the same in a dimension as the orthopedic application site. In another embodiment, the fully expanded implantable device(s) of the present invention are larger in a dimension than the orthopedic application site. In another embodiment, the fully expanded implantable device(s) of the present invention are smaller in volume than the orthopedic application site. In another embodiment, the fully expanded implantable device(s) of the present invention are substantially the same volume as orthopedic application site. In another embodiment, the fully expanded implantable device(s) of the present invention are larger in volume than the orthopedic application site. In another embodiment, after being placed in the orthopedic application site the expanded implantable device(s) of the present invention may swell, e.g., by up to 1-20% in one dimension, by absorption and/or adsorption of water or other body fluids.

Some useful implantable device shapes may approximate the contour of a portion of the target orthopedic application site. In one embodiment, the implantable device is shaped as relatively simple convex, dish-like or hemispherical or hemi-ellipsoidal shape and size that is appropriate for treating multiple different sites in different patients.

It is contemplated, in another embodiment, that upon implantation, before their pores become filled with biological fluids, bodily fluids and/or tissue, such implantable devices for orthopedic applications and the like do not entirely fill, cover or span the biological site in which they reside and that an individual implanted elastomeric matrix 10 will, in many cases although not necessarily, have at least one dimension of no more than 50% of the biological site within the entrance thereto or over 50% of the damaged tissue that is being repaired or replaced. In another embodiment, an individual implanted elastomeric matrix 10 as described above will have at least one dimension of no more than 75% of the biological site within the entrance thereto or over 75% of the damaged tissue that is being repaired or replaced. In another embodiment, an individual implanted elastomeric matrix 10 as described above will have at least one dimension of no more than 95% of the biological site within the entrance thereto or over 95% of the damaged tissue that is being repaired or replaced.

In another embodiment, that upon implantation, before their pores become filled with biological fluids, bodily fluids and/or tissue, such implantable devices for orthopedic applications and the like substantially fill, cover or span the biological site in which they reside and an individual implanted elastomeric matrix 10 will, in many cases, although not necessarily, have at least one dimension of no more than about 100% of the biological site within the entrance thereto or cover 100% of the damaged tissue that is being repaired or replaced. In another embodiment, an individual implanted elastomeric matrix 10 as described above will have at least one dimension of no more than about 98% of the biological site within the entrance thereto or cover 98% of the damaged tissue that is being repaired or replaced. In another embodiment, an individual implanted elastomeric matrix 10 as described above will have at least one dimension of no more than about 102% of the biological site within the entrance thereto or cover 102% of the damaged tissue that is being repaired or replaced.

In another embodiment, that upon implantation, before their pores become filled with biological fluids, bodily fluids and/or tissue, such implantable devices for orthopedic applications and the like over fill, cover or span the biological site in which they reside and an individual implanted elastomeric matrix 10 will, in many cases, although not necessarily, have at least one dimension of more than about 105% of the biological site within the entrance thereto or cover 105% of the damaged tissue that is being repaired or replaced. In another embodiment, an individual implanted elastomeric matrix 10 as described above will have at least one dimension of more than about 125% of the biological site within the entrance thereto or cover 125% of the damaged tissue that is being repaired or replaced. In another embodiment, an individual implanted elastomeric matrix 10 as described above will have at least one dimension of more than about 150% of the biological site within the entrance thereto or cover 150% of the damaged tissue that is being repaired or replaced. In another embodiment, an individual implanted elastomeric matrix 10 as described above will have at least one dimension of more than about 200% of the biological site within the entrance thereto or cover 200% of the damaged tissue that is being repaired or replaced. In another embodiment, an individual implanted elastomeric matrix 10 as described above will have at least one dimension of more than about 300% of the biological site within the entrance thereto or cover 300% of the damaged tissue that is being repaired or replaced.

It is contemplated, in another embodiment, that even when their pores become filled with biological fluids, bodily fluids and/or tissue in the course of time, such implantable devices for orthopedic applications and the like do not entirely fill, cover or span the biological site in which they reside and that an individual implanted elastomeric matrix 10 will, in many cases although not necessarily, have a volume of no more than 50% of the biological site within the entrance thereto or over 50% of the damaged tissue that is being repaired or replaced. In another embodiment, an individual implanted elastomeric matrix 10 with pores filled as described above will have a volume of no more than 75% of the biological site within the entrance thereto or over 75% of the damaged tissue that is being repaired or replaced. In another embodiment, an individual implanted elastomeric matrix 10 with pores filled as described above will have a volume of no more than 95% of the biological site within the entrance thereto or over 95% of the damaged tissue that is being repaired or replaced.

In another embodiment, when their pores become filled with biological fluids, bodily fluids and/or tissue in the course of time, such implantable devices for orthopedic applications and the like substantially fill, cover or span the biological site in which they reside and an individual implanted elastomeric matrix 10 will, in many cases, although not necessarily, have a volume of no more than about 100% of the biological site within the entrance thereto or cover 100% of the damaged tissue that is being repaired or replaced. In another embodiment, an individual implanted elastomeric matrix 10 with pores filled as described above will have a volume of no more than about 98% of the biological site within the entrance thereto or cover 98% of the damaged tissue that is being repaired or replaced. In another embodiment, an individual implanted elastomeric matrix 10 with pores filled as described above will have a volume of no more than about 102% of the biological site within the entrance thereto or cover 102% of the damaged tissue that is being repaired or replaced.

In another embodiment, when their pores become filled with biological fluids, bodily fluids and/or tissue in the course of time, such implantable devices for orthopedic applications and the like over fill, cover or span the biological site in which they reside and an individual implanted elastomeric matrix 10 will, in many cases, although not necessarily, have a volume of more than about 105% of the biological site within the entrance thereto or cover 105% of the damaged tissue that is being repaired or replaced. In another embodiment, an individual implanted elastomeric matrix 10 with pores filled as described above will have a volume of more than about 125% of the biological site within the entrance thereto or cover 125% of the damaged tissue that is being repaired or replaced. In another embodiment, an individual implanted elastomeric matrix 10 with pores filled as described above will have a volume of more than about 150% of the biological site within the entrance thereto or cover 300% of the damaged tissue that is being repaired or replaced. In another embodiment, an individual implanted elastomeric matrix 10 with pores filled as described above will have a volume of more than about 150% of the biological site within the entrance thereto or cover 300% of the damaged tissue that is being repaired or replaced.

Well-Characterized Elastomers and Elastomeric Implantable Devices

Elastomers for use as the structural material of elastomeric matrix 10 alone or in combination in blends or solutions are, in one embodiment, well-characterized synthetic elastomeric polymers having suitable mechanical properties which have been sufficiently characterized with regard to chemical, physical or biological properties as to be considered biodurable and suitable for use as in vivo implantable devices in patients, particularly in mammals and especially in humans. In another embodiment, elastomers for use as the structural material of elastomeric matrix 10 are sufficiently characterized with regard to chemical, physical and biological properties as to be considered biodurable and suitable for use as in vivo implantable devices in patients, particularly in mammals and especially in humans.

Elastomeric Matrix Physical Properties

Elastomeric matrix 10 can have any suitable bulk density, also known as specific gravity, consistent with its other properties. For example, in one embodiment, the bulk density, as measured pursuant to the test method described in ASTM Standard D3574, may be from about 0.005 g/cc to about 0.15 g/cc (from about 0.31 lb/ft$^3$ to about 9.4 lb/ft$^3$). In another embodiment, the bulk density may be from about 0.008 g/cc to about 0.127 g/cc (from about 0.5 lb/ft$^3$ to about 8 lb/ft$^3$). In another embodiment, the bulk density may be from about 0.015 g/cc to about 0.115 g/cc (from about 0.93 lb/ft$^3$ to about 7.2 lb/ft$^3$). In another embodiment, the bulk density may be from about 0.024 g/cc to about 0.104 g/cc (from about 1.5 lb/ft$^3$ to about 6.5 lb/ft$^3$).

Elastomeric matrix 10 can have any suitable microscopic surface area consistent with its other properties. Those skilled in the art, e.g., from an exposed plane of the porous material, can routinely estimate the microscopic surface area from the pore frequency, e.g., the number of pores per linear millimeter, and can routinely estimate the pore frequency from the average cell side diameter in µm.

Other suitable physical properties will be apparent to, or will become apparent to, those skilled in the art.

Elastomeric Matrix Mechanical Properties

In one embodiment, reticulated elastomeric matrix 10 has sufficient structural integrity to be self-supporting and free-standing in vitro. However, in another embodiment, elastomeric matrix 10 can be furnished with structural supports such as ribs or struts.

The reticulated elastomeric matrix 10 has sufficient tensile strength such that it can withstand normal manual or mechanical handling during its intended application and during post-processing steps that may be required or desired without tearing, breaking, crumbling, fragmenting or otherwise disintegrating, shedding pieces or particles, or otherwise losing its structural integrity. The tensile strength of the starting material(s) should not be so high as to interfere with the fabrication or other processing of elastomeric matrix 10.

Thus, for example, in one embodiment reticulated elastomeric matrix 10 may have a tensile strength of from about 700 kg/m$^2$ to about 350,000 kg/m$^2$ (from about 1 psi to about 500 psi). In another embodiment, elastomeric matrix 10 may have a tensile strength of from about 700 kg/m$^2$ to about 70,000 kg/m$^2$ (from about 1 psi to about 100 psi).

Sufficient ultimate tensile elongation is also desirable. For example, in another embodiment, reticulated elastomeric matrix 10 has an ultimate tensile elongation of at least about 25%. In another embodiment, elastomeric matrix 10 has an ultimate tensile elongation of at least about 200%.

One embodiment for use in the practice of the invention is a reticulated elastomeric matrix 10 which is sufficiently flexible and resilient, i.e., resiliently-compressible, to enable it to be initially compressed under ambient conditions, e.g., at 25° C., from a relaxed configuration to a first, compact configuration for delivery via a delivery-device, e.g., catheter, endoscope, syringe, cystoscope, trocar or other suitable introducer instrument, for delivery in vitro and, thereafter, to expand to a second, working configuration in situ. Furthermore, in another embodiment, an elastomeric matrix has the herein described resilient-compressibility after being compressed about 5-95% of an original dimension (e.g., compressed about 19/20th-1/20th of an original dimension). In another embodiment, an elastomeric matrix has the herein described resilient-compressibility after being compressed about 10-90% of an original dimension (e.g., compressed about 9/10th-1/10th of an original dimension). As used herein, elastomeric matrix 10 has "resilient-compressibility", i.e., is "resiliently-compressible", when the second, working configuration, in vitro, is at least about 50% of the size of the relaxed configuration in at least one dimension. In another embodiment, the resilient-compressibility of elastomeric matrix 10 is such that the second, working configuration, in vitro, is at least about 80% of the size of the relaxed configuration in at least one dimension. In another embodiment, the resilient-compressibility of elastomeric matrix 10 is such that the second, working configuration, in vitro, is at least about 90% of the size of the relaxed configuration in at least one dimension. In another embodiment, the resilient-compressibility of elastomeric matrix 10 is such that the second, working configuration, in vitro, is at least about 97% of the size of the relaxed configuration in at least one dimension.

In another embodiment, an elastomeric matrix has the herein described resilient-compressibility after being compressed about 5-95% of its original volume (e.g., compressed about 19/20th-1/20th of its original volume). In another embodiment, an elastomeric matrix has the herein described resilient-compressibility after being compressed about 10-90% of its original volume (e.g., compressed about 9/10th-1/10th of its original volume). As used herein, "volume" is the volume swept-out by the outermost 3-dimensional contour of the elastomeric matrix. In another embodiment, the resilient-compressibility of elastomeric matrix 10 is such that the second, working configuration, in vivo, is at least about 50% of the volume occupied by the relaxed configuration. In another embodiment, the resilient-compressibility of elastomeric matrix 10 is such that the second, working configuration, in vivo, is at least about 80% of the volume occupied by the relaxed configuration. In another embodiment, the resilient-compressibility of elastomeric matrix 10 is such that the second, working configuration, in vivo, is at least about 90% of the volume occupied by the relaxed configuration. In another embodiment, the resilient-compressibility of elastomeric matrix 10 is such that the second, working configuration, in vivo, occupies at least about 97% of the volume occupied by the elastomeric matrix in its relaxed configuration.

In one embodiment, the elastomeric matrix 10 expands from the first, compact configuration to the second, working configuration over a short time, e.g., about 95% recovery in 90 seconds or less in one embodiment, or in 40 seconds or less in another embodiment, each from 75% compression strain held for up to 10 minutes. In another embodiment, the expansion from the first, compact configuration to the second, working configuration occurs over a short time, e.g., about 95% recovery in 180 seconds or less in one embodiment, in 90 seconds or less in another embodiment, in 60 seconds or less in another embodiment, each from 75% compression strain held for up to 30 minutes. In another embodiment, elastomeric matrix 10 recovers in about 10 minutes to occupy at least about 97% of the volume occupied by its relaxed configuration, following 75% compression strain held for up to 30 minutes.

In one embodiment, reticulated elastomeric matrix 10 has a compressive strength of from about 700 kg/m$^2$ to about 350,000 kg/m$^2$ (from about 1 psi to about 500 psi) at 50% compression strain. In another embodiment, reticulated elastomeric matrix 10 has a compressive strength of from about 700 kg/m$^2$ to about 70,000 kg/m$^2$ (from about 1 psi to about 100 psi) at 50% compression strain. In another embodiment, reticulated elastomeric matrix 10 has a compressive strength of from about 7,000 kg/m$^2$ to about 420,000 kg/m$^2$ (from about 10 psi to about 600 psi) at 75% compression strain. In another embodiment, reticulated elastomeric matrix 10 has a compressive strength of from about 7,000 kg/m$^2$ to about 140,000 kg/m$^2$ (from about 10 psi to about 200 psi) at 75% compression strain.

In another embodiment, reticulated elastomeric matrix 10 has a compression set, when compressed to 50% of its thickness at about 25° C., i.e., pursuant to ASTM D3574, of not more than about 30%. In another embodiment, elastomeric matrix 10 has a compression set of not more than about 20%. In another embodiment, elastomeric matrix 10 has a compression set of not more than about 10%. In another embodiment, elastomeric matrix 10 has a compression set of not more than about 5%.

In another embodiment, reticulated elastomeric matrix 10 has a tear strength, as measured pursuant to the test method described in ASTM Standard D3574, of from about 0.18 kg/linear cm to about 8.90 kg/linear cm (from about 1 lbs/linear inch to about 50 lbs/linear inch). In another embodiment, reticulated elastomeric matrix 10 has a tear strength, as measured pursuant to the test method described in ASTM Standard D3574, of from about 0.18 kg/linear cm to about 1.78 kg/linear cm (from about 1 lbs/linear inch to about 10 lbs/linear inch).

Table 1 summarizes mechanical property and other properties applicable to embodiments of reticulated elastomeric matrix 10. Additional suitable mechanical properties will be apparent to, or will become apparent to, those skilled in the art.

TABLE 1

Properties of Reticulated Elastomeric Matrix 10

| Property | Typical Values |
| --- | --- |
| Specific Gravity/Bulk Density | 0.31-9.4 lb/ft$^3$ (0.005-0.15 g/cc) |
| Tensile Strength | 1-500 psi (700-350,000 kg/m$^2$) |
| Ultimate Tensile Elongation | ≧25% |
| Compressive Strength at 50% Compression | 1-500 psi (700-350,000 kg/m$^2$) |
| Compressive Strength at 75% Compression | 10-600 psi (7,000-420,000 kg/m$^2$) |
| 50% Compression Set, 22 hours at 25° C. | ≦30% |
| Tear Strength | 1-50 lbs/linear inch (0.18-8.90 kg/linear cm) |

The mechanical properties of the porous materials described herein, if not indicated otherwise, may be determined according to ASTM D3574-01 entitled "Standard Test Methods for Flexible Cellular Materials—Slab, Bonded and Molded Urethane Foams", or other such method as is known to be appropriate by those skilled in the art.

Furthermore, if porosity is to be imparted to the elastomer employed for elastomeric matrix 10 after rather than during the polymerization reaction, good processability is also desirable for post-polymerization shaping and fabrication. For example, in one embodiment, elastomeric matrix 10 has low tackiness.

Biodurability and Biocompatibility

In one embodiment, elastomers are sufficiently biodurable so as to be suitable for long-term implantation in patients, e.g., animals or humans. Biodurable elastomers and elastomeric matrices have chemical, physical and/or biological properties so as to provide a reasonable expectation of biodurability, meaning that the elastomers will continue to exhibit stability when implanted in an animal, e.g., a mammal, for a period of at least 29 days. The intended period of long-term implantation may vary according to the particular application. For many applications, substantially longer periods of implantation may be required and for such applications biodurability for periods of at least 6, 12 or 24 months or 5 years, or longer, may be desirable. Of especial benefit are elastomers that may be considered biodurable for the life of a patient. In the case of the possible use of an embodiment of elastomeric matrix 10 to treat, e.g., a spinal column deficiency, because such conditions may present themselves in rather young human patients, perhaps in their thirties, biodurability in excess of 50 years may be advantageous.

In another embodiment, the period of implantation will be at least sufficient for cellular ingrowth and proliferation to commence, for example, in at least about 4-8 weeks. In another embodiment, elastomers are sufficiently well characterized to be suitable for long-term implantation by having been shown to have such chemical, physical and/or biological properties as to provide a reasonable expectation of biodurability, meaning that the elastomers will continue to exhibit biodurability when implanted for extended periods of time.

Without being bound by any particular theory, biodurability of the elastomeric matrix of the invention can be promoted by selecting a biodurable polymer(s) as the polymeric component of the flowable material used in the sacrificial molding or lyophilization processes for preparing a reticulated elastomeric matrix of the invention. Furthermore, additional considerations to promote the biodurability of the elastomeric matrix formed by a process comprising polymerization, crosslinking, foaming and reticulation include the selection of starting components that are biodurable and the stoichiometric ratios of those components, such that the elastomeric matrix retains the biodurability of its components. For example, elastomeric matrix biodurability can be promoted by minimizing the presence and formation of chemical bonds and groups, such as ester groups, that are susceptible to hydrolysis, e.g., at the patient's body fluid temperature and pH. As a further example, a curing step in excess of about 2 hours can be performed after crosslinking and foaming to minimize the presence of free amine groups in the elastomeric matrix. Moreover, it is important to minimize degradation that can occur during the elastomeric matrix preparation process, e.g., because of exposure to shearing or thermal energy such as may occur during admixing, dissolution, crosslinking and/or foaming, by ways known to those in the art.

As previously discussed, biodurable elastomers and elastomeric matrices are stable for extended periods of time in a biological environment. Such products do not exhibit significant symptoms of breakdown, degradation, erosion or significant deterioration of mechanical properties relevant to their use when exposed to biological environments and/or bodily stresses for periods of time commensurate with that use. However, some amount of cracking, fissuring or a loss in toughness and stiffening—at times referred to as ESC or environmental stress cracking—may not be relevant to many orthopedic and other uses as described herein. Many in vivo applications, e.g., when elastomeric matrix 10 is used for treatment at an orthopedic application site, expose it to little, if any, mechanical stress and, thus, are unlikely to result in mechanical failure leading to serious patient consequences. Accordingly, the absence of ESC may not be a prerequisite for biodurability of suitable elastomers in such applications for which the present invention is intended because elastomeric properties become less important as endothielozation, encapsulation and cellular ingrowth and proliferation advance.

Furthermore, in certain implantation applications, it is anticipated that elastomeric matrix 10 will become in the course of time, for example, in 2 weeks to 1 year, walled-off or encapsulated by tissue, scar tissue or the like, or incorporated and totally integrated into, e.g., the tissue being repaired or the lumen being treated. In this condition, elastomeric matrix 10 has reduced exposure to mobile or circulating biological fluids. Accordingly, the probabilities of biochemical degradation or release of undesired, possibly nocuous, products into the host organism may be attenuated if not eliminated.

In one embodiment, the elastomeric matrix has good biodurability accompanied by good biocompatibility such that the elastomer induces few, if any, adverse reactions in vivo. To that end, in another embodiment for use in the invention are elastomers or other materials that are free of biologically undesirable or hazardous substances or structures that can induce such adverse reactions or effects in vivo when lodged in an intended site of implantation for the intended period of implantation. Such elastomers accordingly should either entirely lack or should contain only very low, biologically tolerable quantities of cytotoxins, mutagens, carcinogens and/or teratogens. In another embodiment, biological characteristics for biodurability of elastomers to be used for fabrication of elastomeric matrix 10 include at least one of resistance to biological degradation, and absence of or extremely low: cytotoxicity, hemotoxicity, carcinogenicity, mutagenicity, or teratogenicity.

Elastomeric Matrices from Elastomer Polymerization, Crosslinking and Foaming

In further embodiments, the invention provides a porous biodurable elastomer and a process for polymerizing, crosslinking and foaming the same which can be used to produce a biodurable reticulated elastomeric matrix 10 as described herein. In another embodiment, reticulation follows.

More particularly, in another embodiment, the invention provides a process for preparing a biodurable elastomeric polyurethane matrix which comprises synthesizing the matrix from a polycarbonate polyol component and an isocyanate component by polymerization, crosslinking and foaming, thereby forming pores, followed by reticulation of the foam to provide a reticulated product. The product is designated as a polycarbonate polyurethane, being a polymer comprising urethane groups formed from, e.g., the hydroxyl groups of the polycarbonate polyol component and the isocyanate groups of the isocyanate component. In this embodiment, the process employs controlled chemistry to provide a reticulated elastomer product with good biodurability characteristics. Pursuant to the invention, the polymerization is conducted to provide a foam product employing chemistry that avoids biologically undesirable or nocuous constituents therein.

In one embodiment, as one starting material, the process employs at least one polyol component. For the purposes of this application, the term "polyol component" includes molecules comprising, on the average, about 2 hydroxyl groups per molecule, i.e., a difunctional polyol or a diol, as well as those molecules comprising, on the average, greater than about 2 hydroxyl groups per molecule, i.e., a polyol or a multi-functional polyol. Exemplary polyols can comprise, on the average, from about 2 to about 5 hydroxyl groups per molecule. In one embodiment, as one starting material, the process employs a difunctional polyol component. In this embodiment, because the hydroxyl group functionality of the diol is about 2, it does not provide the so-called "soft segment" with soft segment crosslinking. In another embodiment, as one starting material of the polyol component, the process employs a multi-functional polyol component in sufficient quantity to provide a controlled degree of soft segment crosslinking. In another embodiment, the process provides sufficient soft segment crosslinking to yield a stable foam. In another embodiment, the soft segment is composed of a polyol component that is generally of a relatively low molecular weight, in one embodiment from about 350 to about 6,000 Daltons, and from about 450 to about 4,000 Daltons in another embodiment. Thus, these polyols are generally liquids or low-melting-point solids. This soft segment polyol is terminated with hydroxyl groups, either primary or secondary. In another embodiment, a soft segment polyol component has about 2 hydroxyl groups per molecule. In another embodiment, a soft segment polyol component has greater than about 2 hydroxyl groups per molecule; more than 2 hydroxyl groups per polyol molecule are required of some polyol molecules to impart soft-segment crosslinking.

In one embodiment, the average number of hydroxyl groups per molecule in the polyol component is about 2. In another embodiment, the average number of hydroxyl groups per molecule in the polyol component is greater than about 2. In another embodiment, the average number of hydroxyl groups per molecule in the polyol component is greater than 2. In one embodiment, the polyol component comprises a tertiary carbon linkage. In one embodiment, the polyol component comprises a plurality of tertiary carbon linkages.

In one embodiment, the polyol component is a polyether polyol, polyester polyol, polycarbonate polyol, hydrocarbon polyol, polysiloxane polyol, poly(ether-co-ester)polyol, poly(ether-co-carbonate)polyol, poly(ether-co-hydrocarbon) polyol, poly(ether-co-siloxane)polyol, poly(ester-co-carbonate)polyol, poly(ester-co-hydrocarbon)polyol, poly(ester-co-siloxane)polyol, poly(carbonate-co-hydrocarbon)polyol, poly(carbonate-co-siloxane)polyol, poly(hydrocarbon-co-siloxane)polyol, or a mixture thereof.

Polyether-type polyols are oligomers of, e.g., alkylene oxides such as ethylene oxide or propylene oxide, polymerized with glycols or polyhydric alcohols, the latter to result in hydroxyl functionalities greater than 2 to allow for soft segment crosslinking. Polyester-type polyols are oligomers of, e.g., the reaction product of a carboxylic acid with a glycol or triol, such as ethylene glycol adipate, propylene glycol adipate, butylene glycol adipate, diethylene glycol adipate, phthalates, polycaprolactone and castor oil. When the reactants include those with hydroxyl functionalities greater than 2, e.g., polyhydric alcohols, soft segment crosslinking is possible.

Polycarbonate-type polyols typically result from the reaction, with a carbonate monomer, of one type of hydrocarbon diol or, for a plurality of diols, hydrocarbon diols each with a different hydrocarbon chain length between the hydroxyl groups. The length of the hydrocarbon chain between adjacent carbonates is the same as the hydrocarbon chain length of the original diol(s). For example, a difunctional polycarbonate polyol can be made by reacting 1,6-hexanediol with a carbonate, such as sodium hydrogen carbonate, to provide the polycarbonate-type polyol 1,6-hexanediol carbonate. The molecular weight for the commercial-available products of this reaction varies from about 500 to about 5,000 Daltons. If the polycarbonate polyol is a solid at 25° C., it is typically melted prior to further processing. Alternatively, in one embodiment, a liquid polycarbonate polyol component can prepared from a mixture of hydrocarbon diols, e.g., all three or any binary combination of 1,6-hexanediol, cyclohexyl dimethanol and 1,4-butanediol. Without being bound by any particular theory, such a mixture of hydrocarbon diols is thought to break-up the crystallinity of the product polycarbonate polyol component, rendering it a liquid at 25° C., and thereby, in foams comprising it, yield a relatively softer foam.

When the reactants used to produce the polycarbonate polyol include those with hydroxyl functionalities greater than 2, e.g., polyhydric alcohols, soft segment crosslinking is possible. Polycarbonate polyols with an average number of hydroxyl groups per molecule greater than 2, e.g., a polycarbonate triol, can be made by using, for example, hexane triol, in the preparation of the polycarbonate polyol component. To make a liquid polycarbonate triol component, mixtures with other hydroxyl-comprising materials, for example, cyclohexyl trimethanol and/or butanetriol, can be reacted with the carbonate along with the hexane triol.

Commercial hydrocarbon-type polyols typically result from the free-radical polymerization of dienes with vinyl monomers, therefore, they are typically difunctional hydroxyl-terminated materials.

Polysiloxane polyols are oligomers of, e.g., alkyl and/or aryl substituted siloxanes such as dimethyl siloxane, diphenyl siloxane or methyl phenyl siloxane, comprising hydroxyl end-groups. Polysiloxane polyols with an average number of hydroxyl groups per molecule greater than 2, e.g., a polysiloxane triol, can be made by using, for example, methyl hydroxymethyl siloxane, in the preparation of the polysiloxane polyol component.

A particular type of polyol need not be limited to those formed from a single monomeric unit. For example, a polyether-type polyol can be formed from a mixture of ethylene oxide and propylene oxide.

Additionally, in another embodiment, copolymers or copolyols can be formed from any of the above polyols by methods known to those in the art. Thus, the following binary component polyol copolymers can be used: poly(ether-co-ester)polyol, poly(ether-co-carbonate)polyol, poly(ether-co-hydrocarbon)polyol, poly(ether-co-siloxane)polyol, poly(ester-co-carbonate)polyol, poly(ester-co-hydrocarbon)polyol, poly(ester-co-siloxane)polyol, poly(carbonate-co-hydrocarbon)polyol, poly(carbonate-co-siloxane)polyol and poly(hydrocarbon-co-siloxane)polyol. For example, a poly(ether-co-ester) polyol can be formed from units of polyethers formed from ethylene oxide copolymerized with units of polyester comprising ethylene glycol adipate. In another embodiment, the copolymer is a poly(ether-co-carbonate)polyol, poly(ether-co-hydrocarbon)polyol, poly(ether-co-siloxane) polyol, poly(carbonate-co-hydrocarbon)polyol, poly(carbonate-co-siloxane)polyol, poly(hydrocarbon-co-siloxane) polyol or a mixture thereof. In another embodiment, the copolymer is a poly(carbonate-co-hydrocarbon)polyol, poly(carbonate-co-siloxane)polyol, poly(hydrocarbon-co-siloxane)polyol or a mixture thereof. In another embodiment, the copolymer is a poly(carbonate-co-hydrocarbon)polyol. For example, a poly(carbonate-co-hydrocarbon)polyol can be formed by polymerizing 1,6-hexanediol, 1,4-butanediol and a hydrocarbon-type polyol with carbonate.

In another embodiment, the polyol component is a polyether polyol, polycarbonate polyol, hydrocarbon polyol, polysiloxane polyol, poly(ether-co-carbonate)polyol, poly(ether-co-hydrocarbon)polyol, poly(ether-co-siloxane)polyol, poly(carbonate-co-hydrocarbon)polyol, poly(carbonate-co-siloxane)polyol, poly(hydrocarbon-co-siloxane)polyol or a mixture thereof. In another embodiment, the polyol component is a polycarbonate polyol, hydrocarbon polyol, polysiloxane polyol, poly(carbonate-co-hydrocarbon)polyol, poly(carbonate-co-siloxane)polyol, poly(hydrocarbon-co-siloxane)polyol or a mixture thereof. In another embodiment, the polyol component is a polycarbonate polyol, poly(carbonate-co-hydrocarbon)polyol, poly(carbonate-co-siloxane)polyol, poly(hydrocarbon-co-siloxane) polyol or a mixture thereof. In another embodiment, the polyol component is a polycarbonate polyol, poly(carbonate-co-hydrocarbon)polyol, poly(carbonate-co-siloxane)polyol or a mixture thereof. In another embodiment, the polyol component is a polycarbonate polyol.

Furthermore, in another embodiment, mixtures, admixtures and/or blends of polyols and copolyols can be used in the elastomeric matrix of the present invention. In another embodiment, the molecular weight of the polyol is varied. In another embodiment, the functionality of the polyol is varied.

In another embodiment, as either difunctional polycarbonate polyols or difunctional hydrocarbon polyols cannot, on their own, induce soft segment crosslinking, higher functionality is introduced into the formulation through the use of a chain extender component with a hydroxyl group functionality greater than about 2. In another embodiment, higher functionality is introduced through the use of an isocyanate component with an isocyanate group functionality greater than about 2.

Commercial polycarbonate diols with molecular weights of from about 500 to about 5,000 Daltons, such as POLY-CD CD220 from Arch Chemicals, Inc. (Norwalk, Conn.) and PC-1733 from Stahl USA, Inc. (Peabody, Mass.), are readily available. Commercial hydrocarbon polyols are available from Sartomer (Exton, Pa.). Commercial polyether polyols are readily available, such as the PLURACOL®, e.g., PLURACOL® GP430 with functionality of 3 and LUPRANOL® lines from BASF Corp. (Wyandotte, Mich.), VORANOL® from Dow Chemical Corp. (Midland, Mich.), BAYCOLL® B, DESMOPHEN® and MULTRANOL® from Bayer Corp. (Leverkusen, Germany), and from Huntsman Corp. (Madison Heights, Mich.). Commercial polyester polyols are readily available, such as LUPRAPHEN® from BASF, TONE® polycaprolactone and VORANOL from Dow, BAYCOLL A and the DESMOPHEN® U series from Bayer, and from Huntsman. Commercial polysiloxane polyols are readily available, such as from Dow.

The process also employs at least one isocyanate component and, optionally, at least one chain extender component to provide the so-called "hard segment". For the purposes of this application, the term "isocyanate component" includes molecules comprising, on the average, about 2 isocyanate groups per molecule as well as those molecules comprising, on the average, greater than about 2 isocyanate groups per molecule. The isocyanate groups of the isocyanate component are reactive with reactive hydrogen groups of the other ingredients, e.g., with hydrogen bonded to oxygen in hydroxyl groups and with hydrogen bonded to nitrogen in amine groups of the polyol component, chain extender, crosslinker and/or water.

In one embodiment, the average number of isocyanate groups per molecule in the isocyanate component is about 2. In another embodiment, the average number of isocyanate groups per molecule in the isocyanate component is greater than about 2. In another embodiment, the average number of isocyanate groups per molecule in the isocyanate component is greater than 2.

The isocyanate index, a quantity well known to those in the art, is the mole ratio of the number of isocyanate groups in a formulation available for reaction to the number of groups in the formulation that are able to react with those isocyanate groups, e.g., the reactive groups of diol(s), polyol component(s), chain extender(s) and water, when present. In one embodiment, the isocyanate index is from about 0.9 to about 1.1. In another embodiment, the isocyanate index is from about 0.9 to about 1.02. In another embodiment, the isocyanate index is from about 0.98 to about 1.02. In another embodiment, the isocyanate index is from about 0.9 to about 1.0. In another embodiment, the isocyanate index is from about 0.9 to about 0.98.

Exemplary diisocyanates include aliphatic diisocyanates, isocyanates comprising aromatic groups, the so-called "aromatic diisocyanates", or a mixture thereof. Aliphatic diisocyanates include tetramethylene diisocyanate, cyclohexane-1,2-diisocyanate, cyclohexane-1,4-diisocyanate, hexamethylene diisocyanate, isophorone diisocyanate, methylene-bis-(p-cyclohexyl isocyanate) ("$H_{12}$ MDI"), or a mixture thereof. Aromatic diisocyanates include p-phenylene diisocyanate, 4,4'-diphenylmethane diisocyanate ("4,4'-MDI"), 2,4'-diphenylmethane diisocyanate ("2,4'-MDI"), 2,4-toluene diisocyanate ("2,4-TDI"), 2,6-toluene diisocyanate ("2,6-TDI"), m-tetramethylxylene diisocyanate, or a mixture thereof.

Exemplary isocyanate components comprising, on the average, greater than about 2 isocyanate groups per molecule, include an adduct of hexamethylene diisocyanate and water comprising about 3 isocyanate groups, available commercially as DESMODUR® N100 from Bayer, and a trimer of hexamethylene diisocyanate comprising about 3 isocyanate groups, available commercially as MONDUR® N3390 from Bayer.

In one embodiment, the isocyanate component contains a mixture of at least about 5% by weight of 2,4'-MDI with the balance 4,4'-MDI. In another embodiment, the isocyanate component contains a mixture of at least 5% by weight of 2,4'-MDI with the balance 4,4'-MDI. In another embodiment, the isocyanate component contains a mixture of from about 5% to about 50% by weight of 2,4'-MDI with the balance 4,4'-MDI. In another embodiment, the isocyanate component contains a mixture of from 5% to about 50% by weight of 2,4'-MDI with the balance 4,4'-MDI. In another embodiment, the isocyanate component contains a mixture of from about 5% to about 40% by weight of 2,4'-MDI with the balance 4,4'-MDI. In another embodiment, the isocyanate component contains a mixture of from 5% to about 40% by weight of 2,4'-MDI with the balance 4,4'-MDI. In another embodiment, the isocyanate component contains a mixture of from 5% to about 35% by weight of 2,4'-MDI with the balance 4,4'-MDI. Without being bound by any particular theory, it is thought that the use of higher amounts of 2,4'-MDI in a blend with 4,4'-MDI results in a softer elastomeric matrix because of the disruption of the crystallinity of the hard segment arising out of the asymmetric 2,4'-MDI structure.

Suitable diisocyanates include MDI, such as ISONATE® 125M, certain members of the PAPI® series from Dow and ISONATE 500P from Dow; isocyanates containing a mixture of 4,4'-MDI and 2,4'-MDI, such as RUBINATE® 9433 and RUBINATE 9258, each from Huntsman, and MONDUR MRS 2 and MRS 20 from Bayer; TDI, e.g., from Lyondell Corp. (Houston, Tex.); isophorone diisocyanate, such as VESTAMAT® from Degussa (Germany); $H_{12}$ MDI, such as DESMODUR W from Bayer; and various diisocyanates from BASF.

Suitable isocyanate components comprising, on the average, greater than about 2 isocyanate groups per molecule, include the following modified diphenylmethane-diisocyanate type, each available from Dow: ISOBIND® 1088, with an isocyanate group functionality of about 3; ISONATE 143L, with an isocyanate group functionality of about 2.1; PAPI 27, with an isocyanate group functionality of about 2.7; PAPI 94, with an isocyanate group functionality of about 2.3; PAPI 580N, with an isocyanate group functionality of about 3; and PAPI 20, with an isocyanate group functionality of about 3.2.

Exemplary chain extenders include diols, diamines, alkanol amines or a mixture thereof. In one embodiment, the chain extender is an aliphatic diol having from 2 to 10 carbon atoms. In another embodiment, the diol chain extender is selected from ethylene glycol, 1,2-propane diol, 1,3-propane diol, 1,4-butane diol, 1,5-pentane diol, diethylene glycol, triethylene glycol or a mixture thereof. In another embodiment, the chain extender is a diamine having from 2 to 10 carbon atoms. In another embodiment, the diamine chain extender is selected from ethylene diamine, 1,3-diaminobutane, 1,4-diaminobutane, 1,5 diaminopentane, 1,6-diaminohexane, 1,7-diaminoheptane, 1,8-diaminooctane, isophorone diamine or a mixture thereof. In another embodiment, the chain extender is an alkanol amine having from 2 to 10 carbon atoms. In another embodiment, the alkanol amine chain extender is selected from diethanolamine, triethanolamine, isopropanolamine, dimethylethanolamine, methyldiethanolamine, diethylethanolamine or a mixture thereof.

Commercially available chain extenders include the the JEFFAMINE® series of diamines, triamines and polyetheramines available from Huntsman, VERSAMIN® isophorone diamine from Creanova, the VERSALINK® series of diamines available from Air Products Corp. (Allentown, Pa.), ethanolamine, diethylethanolamine and isopropanolamine available from Dow, and various chain extenders from Bayer, BASF and UOP Corp. (Des Plaines, Ill.).

In one embodiment, a small quantity of an optional ingredient, such as a multi-functional hydroxyl compound or other crosslinker having a functionality greater than 2, e.g., glycerol, is present to allow crosslinking. In another embodiment, the optional multi-functional crosslinker is present in an amount just sufficient to achieve a stable foam, i.e., a foam that does not collapse to become non-foamlike. Alternatively, or in addition, polyfunctional adducts of aliphatic and cycloaliphatic isocyanates can be used to impart crosslinking in combination with aromatic diisocyanates. Alternatively, or in addition, polyfunctional adducts of aliphatic and cycloaliphatic isocyanates can be used to impart crosslinking in combination with aliphatic diisocyanates.

Optionally, the process employs at least one catalyst in certain embodiments selected from a blowing catalyst, e.g., a tertiary amine, a gelling catalyst, e.g., dibutyltin dilaurate, or a mixture thereof. Moreover, it is known in the art that tertiary amine catalysts can also have gelling effects, that is, they can act as a blowing and gelling catalyst. Exemplary tertiary amine catalysts include the TOTYCAT® line from Toyo Soda Co. (Japan), the TEXACAT® line from Texaco Chemical Co. (Austin, Tex.), the KOSMOS® and TEGO® lines from Th. Goldschmidt Co. (Germany), the DMP® line from Rohm and Haas (Philadelphia, Pa.), the KAO LIZER® line from Kao Corp. (Japan), and the QUINCAT® line from Enterprise Chemical Co. (Altamonte Springs, Fla.). Exemplary organotin catalysts include the FOMREZ® and FOMREZ UL® lines from Witco Corporation (Middlebury, Conn.), the COCURE® and COSCAT® lines from Cosan Chemical Co. (Carlstadt, N.J.), and the DABCO® and POLYCAT® lines from Air Products.

In certain embodiments, the process employs at least one surfactant. Exemplary surfactants include TEGOSTAB® BF 2370 from Goldschmidt, DC 5241 from Dow Corning (Midland, Mich.), and other non-ionic organosilicones, such as the polydimethylsiloxane types available from Dow Corning, Air Products and General Electric (Waterford, N.Y.).

In certain embodiments, the process employs at least one cell-opener. Exemplary cell-openers include ORTEGOL® 501 from Goldschmidt.)

Crosslinked polyurethanes may be prepared by approaches which include the prepolymer process and the one-shot process. An embodiment involving a prepolymer is as follows. First, the prepolymer is prepared by a conventional method from at least one isocyanate component (e.g., MDI) and at least one multi-functional soft segment material with a functionality greater than 2 (e.g., a polyether-based soft segment with a functionality of 3). Then, the prepolymer, optionally at least one catalyst (e.g., dibutyltin dilaurate) and at least one difunctional chain extender (e.g., 1,4-butanediol) are admixed in a mixing vessel to cure or crosslink the mixture. In another embodiment, crosslinking takes place in a mold. In another embodiment, crosslinking and foaming, i.e., pore formation, take place together. In another embodiment, crosslinking and foaming take place together in a mold.

Alternatively, the so-called "one-shot" approach may be used. A one-shot embodiment requires no separate prepolymer-making step. In one embodiment, the starting materials, such as those described in the previous paragraph, are admixed in a mixing vessel and then foamed and crosslinked. In another embodiment, the ingredients are heated before they are admixed. In another embodiment, the ingredients are heated as they are admixed. In another embodiment, crosslinking takes place in a mold. In another embodiment, foaming and crosslinking take place together. In another embodiment, crosslinking and foaming take place together in a mold. In another embodiment, all of the ingredients except for the isocyanate component are admixed in a mixing vessel. The isocyanate component is then added, e.g., with high-speed stirring, and crosslinking and foaming ensue. In another embodiment, this foaming mix is poured into a mold and allowed to rise.

In another embodiment, the polyol component is admixed with the isocyanate component and other optional additives, such as a viscosity modifier, surfactant and/or cell opener, to form a first liquid. In another embodiment, the polyol component is a liquid at the mixing temperature. In another embodiment, the polyol component is a solid, therefore, the mixing temperature is raised such that the polyol component is liquefied prior to mixing, e.g., by heating. Next, a second liquid is formed by admixing a blowing agent and optional additives, such as gelling catalyst and/or blowing catalyst. Then, the first liquid and the second liquid are admixed in a mixing vessel and then foamed and crosslinked.

In another embodiment, any or all of the processing approaches of the invention may be used to make foam with a density greater than 3.4 lbs/ft$^3$ (0.054 g/cc). In this embodiment, no or a minimum amount of crosslinker(s), such as glycerol, are used; the functionality of the isocyanate component is from 2.0 to 2.3; the isocyanate component consists essentially of MDI; and the amount of 4,4'-MDI is greater than about 55% by weight of the isocyanate component. The molecular weight of the polyol component is from about 1,000 to about 2,000 Daltons. The amount of blowing agent, e.g., water, is adjusted to obtain non-reticulated foam densities greater than 3.4 lbs/ft$^3$ (0.054 g/cc). A reduced amount of blowing agent may reduce the number of urea linkages in the material. Any reduction in stiffness and/or tensile strength and/or compressive strength caused by lower crosslinking and/or fewer urea linkages can be compensated for by using di-functional chain extenders, such as butanediol, and/or increasing the density of the foam. Reducing the degree of crosslinking and, consequently, increasing the foam's toughness and/or elongation to break should allow for more efficient reticulation because the higher density foam material which results can better withstand the sudden impact a reticulation process can provide with minimal, if any, damage to struts 16.

In one embodiment, the invention provides a process for preparing a flexible polyurethane biodurable matrix capable of being reticulated based on polycarbonate polyol component and isocyanate component starting materials. In another embodiment, a porous biodurable elastomer polymerization process for making a resilient polyurethane matrix is provided which process comprises admixing a polycarbonate polyol component and an aliphatic isocyanate component, for example $H_{12}$ MDI.

In another embodiment, the foam is substantially free of isocyanurate linkages. In another embodiment, the foam has no isocyanurate linkages. In another embodiment, the foam is substantially free of biuret linkages. In another embodiment, the foam has no biuret linkages. In another embodiment, the foam is substantially free of allophanate linkages. In another embodiment, the foam has no allophanate linkages. In another embodiment, the foam is substantially free of isocyanurate and biuret linkages. In another embodiment, the foam has no isocyanurate and biuret linkages. In another embodiment, the foam is substantially free of isocyanurate and allophanate linkages. In another embodiment, the foam has no isocyanurate and allophanate linkages. In another embodiment, the foam is substantially free of allophanate and biuret linkages. In another embodiment, the foam has no allophanate and biuret linkages. In another embodiment, the foam is substantially free of allophanate, biuret and isocyanurate linkages. In another embodiment, the foam has no allophanate, biuret and isocyanurate linkages. Without being bound by any particular theory, it is thought that the absence of allophanate, biuret and/or isocyanurate linkages provides an enhanced degree of flexibility to the elastomeric matrix because of lower crosslinking of the hard segments.

In certain embodiments, additives helpful in achieving a stable foam, for example, surfactants and catalysts, can be included. By limiting the quantities of such additives to the minimum desirable while maintaining the functionality of each additive, the impact on the toxicity of the product can be controlled.

In one embodiment, elastomeric matrices of various densities, e.g., from about 0.005 to about 0.15 g/cc (from about 0.31 to about 9.4 lb/ft$^3$) are produced. The density is controlled by, e.g., the amount of blowing or foaming agent, the isocyanate index, the isocyanate component content in the formulation, the reaction exotherm, and/or the pressure of the foaming environment.

Exemplary blowing agents include water and the physical blowing agents, e.g., volatile organic chemicals such as hydrocarbons, ethanol and acetone, and various fluorocarbons and their more environmentally friendly replacements, such as hydrofluorocarbons, chlorofluorocarbons and hydrochlorofluorocarbons. The reaction of water with an isocyanate group yields carbon dioxide, which serves as a blowing agent. Moreover, combinations of blowing agents, such as water with a fluorocarbon, can be used in certain embodiments. In another embodiment, water is used as the blowing agent. Commercial fluorocarbon blowing agents are available from Huntsman, E.I. duPont de Nemours and Co. (Wilmington, Del.), Allied Chemical (Minneapolis, Minn.) and Honeywell (Morristown, N.J.).

For the purpose of this invention, for every 100 parts by weight (or 100 grams) of polyol component (e.g., polycarbonate polyol, polysiloxane polyol) used to make an elastomeric matrix through foaming and crosslinking, the amounts of the other components present, by weight, in a formulation are as follows: from about 10 to about 90 parts (or grams) isocyanate component (e.g., MDIs, their mixtures, $H_{12}$MDI) with an isocyanate index of from about 0.85 to about 1.10, from about 0.5 to about 6.0 parts (or grams) blowing agent (e.g., water), from about 0.1 to about 2.0 parts (or grams) blowing catalyst (e.g., tertiary amine), from about 0.1 to about 8.0 parts (or grams) surfactant, and from about 0.1 to about 8.0 parts (or grams) cell opener. Of course, the actual amount of isocyanate component used is related to and depends upon the magnitude of the isocyanate index for a particular formulation. Additionally, for every 100 parts by weight (or 100 grams) of polyol component used to make an elastomeric matrix through foaming and crosslinking, the amounts of the following optional components, when present in a formulation, are as follows by weight: up to about 20 parts (or grams) chain extender, up to about 20 parts (or grams) crosslinker, up to about 0.5 parts (or grams) gelling catalyst (e.g., a compound comprising tin), up to about 10.0 parts (or grams) physical blowing agent (e.g., hydrocarbons, ethanol, acetone, fluorocarbons), and up to about 15 parts (or grams) viscosity modifier.

Matrices with appropriate properties for the purposes of the invention, as determined by testing, for example, acceptable compression set at human body temperature, airflow, tensile strength and compressive properties, can then be reticulated.

In another embodiment, the gelling catalyst, e.g., the tin catalyst, is omitted and optionally substituted with another catalyst, e.g., a tertiary amine. In one embodiment, the tertiary amine catalyst comprises one or more non-aromatic amines. In another embodiment, the reaction is conducted so that the tertiary amine catalyst, if employed, is wholly reacted into the polymer, and residues of same are avoided. In another embodiment, the gelling catalyst is omitted and, instead, higher foaming temperatures are used.

In another embodiment, to enhance biodurability and biocompatibility, ingredients for the polymerization process are selected so as to avoid or minimize the presence in the end product elastomeric matrix of biologically adverse substances or substances susceptible to biological attack.

An alternative preparation embodiment pursuant to the invention involves partial or total replacement of water as a blowing agent with water-soluble spheres, fillers or particles which are removed, e.g., by washing, extraction or melting, after full crosslinking of the matrix.

Further Process Aspects of the Invention

Figure 2:
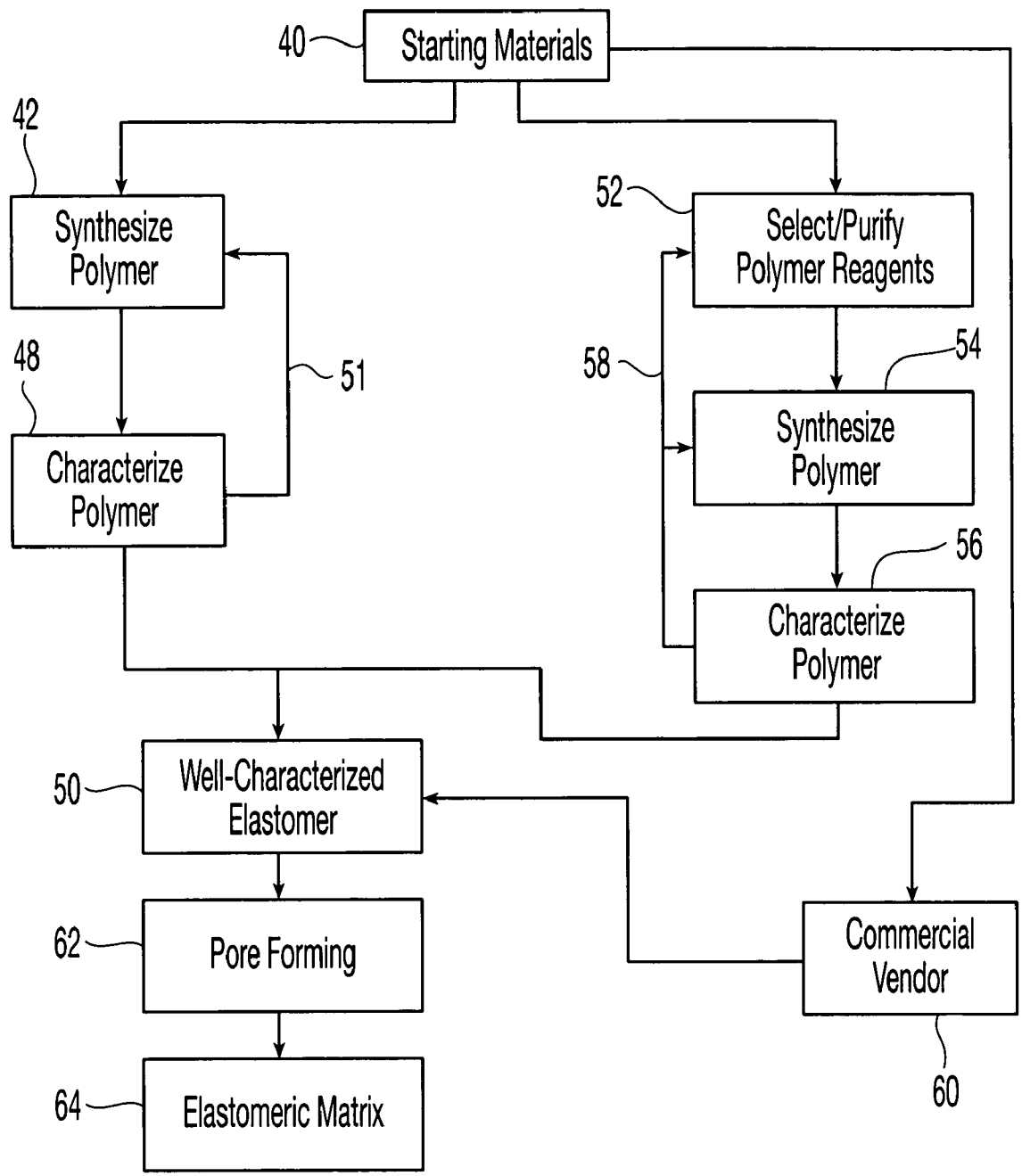
FIG. 2 is a schematic block flow diagram of a process for preparing a porous biodurable elastomeric implantable device according to the invention.

Referring now to FIG. 2, the schematic block flow diagram shown gives a broad overview of alternative embodiments of processes according to the invention whereby an implantable device comprising a biodurable, porous, reticulated, elastomeric matrix 10 can be prepared from raw elastomer or elastomer reagents by one or another of several different process routes.

In a first route, elastomers prepared by a process according to the invention, as described herein, are rendered to comprise a plurality of cells by using, e.g., a blowing agent or agents, employed during their preparation. In particular, starting materials 40, which may comprise, for example, a polyol component, an isocyanate, optionally a crosslinker, and any desired additives such as surfactants and the like, are employed to synthesize the desired elastomeric polymer, in synthesis step 42, either with or without significant foaming or other pore-generating activity. The starting materials are selected to provide desirable mechanical properties and to enhance biocompatibility and biodurability. The elastomeric polymer product of step 42 is then characterized, in step 48, as to chemical nature and purity, physical and mechanical properties and, optionally, also as to biological characteristics, all as described above, yielding well-characterized elastomer 50. Optionally, the characterization data can be employed to control or modify step 42 to enhance the process or the product, as indicated by pathway 51.

Alternately, well-characterized elastomer 50 is generated from starting materials 40 and supplied to the process facility by a commercial vendor 60. Such elastomers are synthesized pursuant to known methods and subsequently rendered porous. Exemplary elastomers of this type are BIONATE® 80A aromatic polyurethane elastomer and CARBOTHANE PC 3575A aliphatic polyurethane elastomer. The elastomer 50 can be rendered porous, e.g., by a blowing agent employed in a polymerization reaction or in a post-polymerization step. In the post-polymerization step (e.g., starting with a commercially available exemplary elastomer or elastomers) a blowing agents or agents can enter the starting material(s), e.g., by absorbtion therein and/or adsorption thereon, optionally under the influence of elevated temperature and/or pressure, before the blowing gas is released from the blowing agent(s) to form an elastomeric matrix comprising pores. In one embodiment, the pores are interconnected. The amount of interconnectivity can depend on, e.g., the temperature applied to the polymer, the pressure applied to the polymer, the gas concentration in the polymer, the gas concentration on the polymer surface, the rate of gas release, and/or the mode of gas release.

If desired, the elastomeric polymer reagents employed in starting material 40 may be selected to avoid adverse by-products or residuals and purified, if necessary, in step 52. Polymer synthesis, step 54, is then conducted on the selected and purified starting materials and is conducted to avoid generation of adverse by-products or residuals. The elastomeric polymer produced in step 54 is then characterized, in step 56, as described previously for step 48, to facilitate production of a high quality, well-defined product, well-characterized elastomer 50. In another embodiment, the characterization results are fed back for process control as indicated by pathway 58 to facilitate production of a high quality, well-defined product, well-characterized elastomer 50.

The invention provides, in one embodiment, a reticulated biodurable elastomeric matrix comprising polymeric elements which are specifically designed for the purpose of biomedical implantation. The elastomeric matrix comprises biodurable polymeric materials and is prepared by a process or processes which avoid chemically changing the polymer, the formation of undesirable by-products, and residuals comprising undesirable unreacted starting materials. In some cases, foams comprising polyurethanes and created by known techniques may not be appropriate for long-term endovascular, orthopedic and related applications because of, e.g., the presence of undesirable unreacted starting materials or undesirable by-products. In one embodiment, the elastomeric matrix is formed from commercially available biodurable polymeric elastomeric material(s) and chemical change to the starting elastomeric material(s) is avoided in the process or processes by which the porous and reticulated elastomeric matrix is formed.

In another embodiment, chemical characteristics for biodurability of elastomers to be used for fabrication of elastomeric matrix 10 include one or more of: good oxidative stability; a chemistry that is free or substantially free of linkages that are prone to biological degradation, for example, certain polyether linkages or hydrolyzable ester linkages that may be introduced by incorporating a polyether or polyester polyol component into the polyurethane; a chemically well-defined product which is relatively refined or purified and free or substantially free of adverse impurities, reactants, by-products; oligomers and the like; a well-defined molecular weight, unless the elastomer is crosslinked; and solubility in a biocompatible solvent unless, of course, the elastomer is crosslinked.

In another embodiment, process-related characteristics, referring to a process used for the preparation of the elastomer of the solid phase 12, for biodurability of elastomers to be used for fabrication of elastomeric matrix 10 include one or more of: process reproducibility; process control for product consistency; and avoidance or substantial removal of adverse impurities, reactants, by-products, oligomers and the like.

The pore-making, reticulation and other post-polymerization processes of the invention discussed below are, in certain embodiments, carefully designed and controlled. To this end, in certain embodiments, processes of the invention avoid introducing undesirable residuals or otherwise adversely affecting the desirable biodurability properties of the starting material(s). In another embodiment, the starting material(s) may be further processed and/or characterized to enhance, provide or document a property relevant to biodurability. In another embodiment, the requisite properties of elastomers can be characterized as appropriate and the process features can be adapted or controlled to enhance biodurability, pursuant to the teachings of the present specification.

Reticulation of Elastomeric Matrices

Elastomeric matrix 10 can be subjected to any of a variety of post-processing treatments to enhance its utility, some of which are described herein and others of which will be apparent to those skilled in the art. In one embodiment, reticulation of an elastomeric matrix 10 of the invention, if not already a part of the described production process, may be used to remove at least a portion of any existing interior "windows", i.e., the residual cell walls 22 illustrated in FIG. 1. Reticulation tends to increase porosity and fluid permeability.

Porous or foam materials with some ruptured cell walls are generally known as "open-cell" materials or foams. In contrast, porous materials known as "reticulated" or "at least partially reticulated" have many, i.e., at least about 40%, of the cell walls that would be present in an identical porous material except composed exclusively of cells that are closed, at least partially removed. Where the cell walls are least partially removed by reticulation, adjacent reticulated cells open into, interconnect with, and communicate with each other. Porous materials from which more, i.e., at least about 65%, of the cell walls have been removed are known as "further reticulated". If most, i.e., at least about 80%, or substantially all, i.e., at least about 90%, of the cell walls have been removed then the porous material that remains is known as "substantially reticulated" or "fully reticulated", respectfully. It will be understood that, pursuant to this art usage, a reticulated material or foam comprises a network of at least partially open interconnected cells.

"Reticulation" generally refers to a process for at least partially removing cell walls, not merely rupturing or tearing them by a crushing process. Moreover, crushing undesirable creates debris that must be removed by further processing. In another embodiment, the reticulation process substantially fully removes at least a portion of the cell walls. Reticulation may be effected, for example, by at least partially dissolving away cell walls, known variously as "solvent reticulation" or "chemical reticulation"; or by at least partially melting, burning and/or exploding out cell walls, known variously as "combustion reticulation", "thermal reticulation" or "percussive reticulation". Melted material arising from melted cell walls can be deposited on the struts. In one embodiment, such a procedure may be employed in the processes of the invention to reticulate elastomeric matrix 10. In another embodiment, all entrapped air in the pores of elastomeric matrix 10 is evacuated by application of vacuum prior to reticulation. In another embodiment, reticulation is accomplished through a plurality of reticulation steps. In another embodiment, two reticulation steps are used. In another embodiment, a first combustion reticulation is followed by a second combustion reticulation. In another embodiment, combustion reticulation is followed by chemical reticulation. In another embodiment, chemical reticulation is followed by combustion reticulation. In another embodiment, a first chemical reticulation is followed by a second chemical reticulation.

In one embodiment relating to orthopedic applications and the like, the elastomeric matrix 10 can be reticulated to provide an interconnected pore structure, the pores having an average diameter or other largest transverse dimension of at least about 10 μm. In another embodiment, the elastomeric matrix can be reticulated to provide pores with an average diameter or other largest transverse dimension of at least about 20 μm. In another embodiment, the elastomeric matrix can be reticulated to provide pores with an average diameter or other largest transverse dimension of at least about 50 μm. In another embodiment, the elastomeric matrix can be reticulated to provide pores with an average diameter or other largest transverse dimension of at least about 150 μm. In another embodiment, the elastomeric matrix can be reticulated to provide pores with an average diameter or other largest transverse dimension of at least about 250 μm. In another embodiment, the elastomeric matrix can be reticulated to provide pores with an average diameter or other largest transverse dimension of greater than about 250 μm. In another embodiment, the elastomeric matrix can be reticulated to provide pores with an average diameter or other largest transverse dimension of greater than 250 μm. In another embodiment, the elastomeric matrix can be reticulated to provide pores with an average diameter or other largest transverse dimension of at least about 450 μm. In another embodiment, the elastomeric matrix can be reticulated to provide pores with an average diameter or other largest transverse dimension of greater than about 450 μm. In another embodiment, the elastomeric matrix can be reticulated to provide pores with an average diameter or other largest transverse dimension of greater than 450 μm. In another embodiment, the elastomeric matrix can be reticulated to provide pores with an average diameter or other largest transverse dimension of at least about 500 μm.

In another embodiment relating to orthopedic applications and the like, the elastomeric matrix can be reticulated to provide pores with an average diameter or other largest transverse dimension of not greater than about 600 μm. In another embodiment, the elastomeric matrix can be reticulated to provide pores with an average diameter or other largest transverse dimension of not greater than about 450 μm. In another embodiment, the elastomeric matrix can be reticulated to provide pores with an average diameter or other largest transverse dimension of not greater than about 250 μm. In another embodiment, the elastomeric matrix can be reticulated to provide pores with an average diameter or other largest transverse dimension of not greater than about 150 μm. In another embodiment, the elastomeric matrix can be reticulated to provide pores with an average diameter or other largest transverse dimension of not greater than about 20 μm.

In another embodiment relating to orthopedic applications and the like, the elastomeric matrix can be reticulated to provide pores with an average diameter or other largest transverse dimension of from about 10 μm to about 50 μm. In another embodiment, the elastomeric matrix can be reticulated to provide pores with an average diameter or other largest transverse dimension of from about 20 μm to about 150 μm. In another embodiment, the elastomeric matrix can be reticulated to provide pores with an average diameter or other largest transverse dimension of from about 150 μm to about 250 μm. In another embodiment, the elastomeric matrix can be reticulated to provide pores with an average diameter or other largest transverse dimension of from about 250 μm to about 500 μm. In another embodiment, the elastomeric matrix can be reticulated to provide pores with an average diameter or other largest transverse dimension of from about 450 μm to about 600 μm. In another embodiment, the elastomeric matrix can be reticulated to provide pores with an average diameter or other largest transverse dimension of from about 10 μm to about 500 μm. In another embodiment, the elastomeric matrix can be reticulated to provide pores with an average diameter or other largest transverse dimension of from about 10 μm to about 600 μm.

Optionally, the reticulated elastomeric matrix may be purified, for example, by solvent extraction, either before or after reticulation. Any such solvent extraction, such as with isopropyl alcohol, or other purification process is, in one embodiment, a relatively mild process which is conducted so as to avoid or minimize possible adverse impact on the mechanical or physical properties of the elastomeric matrix that may be necessary to fulfill the objectives of this invention.

One embodiment employs chemical reticulation, where the elastomeric matrix is reticulated in an acid bath comprising an inorganic acid. Another embodiment employs chemical reticulation, where the elastomeric matrix is reticulated in a caustic bath comprising an inorganic base. Another embodiment employs solvent reticulation, where a volatile solvent that leaves no residue is used in the process. Another embodiment employs solvent reticulation at a temperature elevated above 25° C. In another embodiment, an elastomeric matrix comprising polycarbonate polyurethane is solvent reticulated with a solvent selected from tetrahydrofuran ("THF"), dimethyl acetamide ("DMAC"), dimethyl sulfoxide ("DMSO"), dimethylformamide ("DMF"), N-methyl-2-pyrrolidone, also known as m-pyrol, or a mixture thereof. In another embodiment, an elastomeric matrix comprising polycarbonate polyurethane is solvent reticulated with THF. In another embodiment, an elastomeric matrix comprising polycarbonate polyurethane is solvent reticulated with N-methyl-2-pyrrolidone. In another embodiment, an elastomeric matrix comprising polycarbonate polyurethane is chemically reticulated with a strong base. In another embodiment, the pH of the strong base is at least about 9.

In any of these chemical or solvent reticulation embodiments, the reticulated foam can optionally be washed. In any of these chemical or solvent reticulation embodiments, the reticulated foam can optionally be dried.

In one embodiment, combustion reticulation may be employed in which a combustible atmosphere, e.g., a mixture of hydrogen and oxygen or methane and oxygen, is ignited, e.g., by a spark. In another embodiment, combustion reticulation is conducted in a pressure chamber. In another embodiment, the pressure in the pressure chamber is substantially reduced, e.g., to below about 50-150 millitorr by evacuation for at least about 2 minutes, before, e.g., hydrogen, oxygen or a mixture thereof, is introduced. In another embodiment, the pressure in the pressure chamber is substantially reduced in more than one cycle, e.g., the pressure is substantially reduced, an unreactive gas such as argon or nitrogen is introduced then the pressure is again substantially reduced, before hydrogen, oxygen or a mixture thereof is introduced. The temperature at which reticulation occurs can be influenced by, e.g., the temperature at which the chamber is maintained and/or by the hydrogen/oxygen ratio in the chamber. In another embodiment, combustion reticulation is followed by an annealing period. In any of these combustion reticulation embodiments, the reticulated foam can optionally be washed. In any of these combustion reticulation embodiments, the reticulated foam can optionally be dried.

In one embodiment, the reticulation process is conducted to provide an elastomeric matrix configuration favoring cellular ingrowth and proliferation into the interior of the matrix. In another embodiment, the reticulation process is conducted to provide an elastomeric matrix configuration which favors cellular ingrowth and proliferation throughout the elastomeric matrix configured for implantation, as described herein.

The term "configure" and the like is used to denote the arranging, shaping and dimensioning of the respective structure to which the term is applied. Thus, reference to a structure as being "configured" for a purpose is intended to reference the whole spatial geometry of the relevant structure or part of a structure as being selected or designed to serve the stated purpose.

Reticulated Elastomeric Matrices by Lyophilization

In one embodiment, a biodurable reticulated elastomeric matrix of the invention can be made by lyophilizing a flowable polymeric material. In another embodiment, the polymeric material comprises a solution of a solvent-soluble biodurable elastomer in a solvent. The flowable polymeric material is subjected to a lyophilization process comprising solidifying the flowable polymeric material to form a solid, e.g., by cooling a solution, then removing the non-polymeric material, e.g., by subliming the solvent from the solid under reduced pressure, to provide an at least partially reticulated elastomeric matrix. The bulk density of the at least partially reticulated elastomeric matrix is less than the density of the starting polymeric material. In another embodiment, a solution of a biodurable elastomer in a solvent is substantially, but not necessarily completely, solidified, then the solvent is sublimed from that material to provide an at least partially reticulated elastomeric matrix. By selecting the appropriate solvent or solvent mixture to dissolve the polymer, aided by agitation and/or the application of heat, a homogeneous solution amenable to lyophilization can be obtained by a suitable mixing process. In another embodiment, the temperature to which the solution is cooled is below the freezing temperature of the solution. In another embodiment, the temperature to which the solution is cooled is above the apparent glass transition temperature of the solid and below the freezing temperature of the solution.

Without being bound by any particular theory, it is thought that, during lyophilization, a polymer solution separates in a controlled manner into either two distinct morphologies: (1) one phase (i.e., the solvent) being continuous and the other phase being dispersed in the continuous phase; or (2) two bicontinuous phases. In each case, subsequent removal of the solvent phase results in a porous structure with a range or distribution of pore sizes. These pores are usually interconnected. Their shape, size and orientation depend upon the properties of the solution and the lyophilization processing conditions in conventional ways. For example, a lyophilization product has a range of pore sizes with dimensions that can be changed by altering, e.g., the freezing temperature, freezing rate, nucleation density, polymer concentration, polymer molecular weight, and the type of solvent(s) in ways known to those in the art.

In general, suitable elastomer materials for use in lyophilization, in one embodiment sufficiently well characterized, comprise elastomers that have or can be formulated with the desirable mechanical properties described in the present specification and have a chemistry favorable to biodurability such that they provide a reasonable expectation of adequate biodurability.

Of particular interest are thermoplastic elastomers such as polyurethanes whose chemistry is associated with good biodurability properties, for example. In one embodiment, such thermoplastic polyurethane elastomers include polycarbonate polyurethanes, polyester polyurethanes, polyether polyurethanes, polysiloxane polyurethanes, polyurethanes with so-called "mixed" soft segments, or a mixture thereof. In another embodiment, thermoplastic polyurethane elastomers include polycarbonate polyurethanes, polyether polyurethanes, polysiloxane polyurethanes, mixed soft segment polyurethanes with these soft segments, or a mixture thereof. In another embodiment, thermoplastic polyurethane elastomers include polycarbonate polyurethanes, polysiloxane polyurethanes, mixed soft segment polyurethanes with these soft segments, or a mixture thereof. Mixed soft segment polyurethanes are known to those skilled in the art and include, e.g., polycarbonate-polyester polyurethanes, polycarbonate-polyether polyurethanes, polycarbonate-polysiloxane polyurethanes, polyester-polyether polyurethanes, polyester-polysiloxane polyurethanes and polyether-polysiloxane polyurethanes. In another embodiment, the thermoplastic polyurethane elastomer comprises at least one diisocyanate in the isocyanate component, at least one chain extender and at least one diol, and may be formed from any combination of the diisocyanates, difunctional chain extenders and diols described in detail above.

In one embodiment, the weight average molecular weight of the thermoplastic elastomer is from about 30,000 to about 500,000 Daltons. In another embodiment, the weight average molecular weight of the thermoplastic elastomer is from about 50,000 to about 250,000 Daltons.

Some suitable thermoplastic polyurethanes for practicing the invention, in one embodiment suitably characterized as described herein, include: polyurethanes with mixed soft segments comprising polysiloxane together with a polyether and/or a polycarbonate component, as disclosed by Meijs et al. in U.S. Pat. No. 6,313,254; and those polyurethanes disclosed by DiDomenico et al. in U.S. Pat. Nos. 6,149,678, 6,111,052 and 5,986,034. In another embodiment, an optional therapeutic agent may be loaded into the appropriate block of other elastomers used in the practice of the invention.

Some commercially-available thermoplastic elastomers suitable for use in practicing the present invention include the line of polycarbonate polyurethanes supplied under the trademark BIONATE® by the Polymer Technology Group Inc. (Berkeley, Calif.). For example, the very well-characterized grades of polycarbonate polyurethane polymer BIONATE® 80A, 55D and 90D reportedly have good mechanical properties, lack cytotoxicity, lack mutagenicity, lack carcinogenicity and are non-hemolytic. Another commercially-available elastomer suitable for use in practicing the present invention is the CHRONOFLEX® C line of biodurable medical grade polycarbonate aromatic polyurethane thermoplastic elastomers available from CardioTech International, Inc. (Woburn, Mass.). Yet another commercially-available elastomer suitable for use in practicing the present invention is the PELLETHANE® line of thermoplastic polyurethane elastomers, in particular the 2363 series products and more particularly those products designated 81A and 85A, from the Dow Chemical Company (Midland, Mich.). Other commercially-available elastomers suitable for use in practicing the present invention include CARBOTHANE®, TECOTHANE® and TECOFLEX®, from Viasys Healthcare (Wilmington, Mass.). These commercial polyurethane polymers are reported to be linear, not crosslinked, polymers; therefore, they are soluble, readily analyzable and readily characterizable.

Solvents for use in practicing lyophilization for the present invention include but are not limited to THF, DMAC, DMSO, DMF, cyclohexane, ethanol, dioxane, N-methyl-2-pyrrolidone and their mixtures. Generally, the amount of polymer in the solution is from about 0.5% to about 30% of the solution by weight in one embodiment, depending upon the solubility of the polymer in the solvent and the final desired properties of the elastomeric reticulated matrix. In another embodiment, the amount of polymer in the solution is from about 0.5% to about 15% of the solution by weight.

Additionally, additives may be present in the polymer-solvent solution, e.g., a buffer. In one embodiment, the additive does not react with the polymer or the solvent. In another embodiment, the additive is a solid material that promotes tissue regeneration or regrowth, a buffer, a reinforcing material, a porosity modifier or a pharmaceutically-active agent.

In another embodiment, the polymer solution can comprise various inserts incorporated with the solution, such as films, plates, foams, scrims, woven, nonwoven, knitted or braided textile structures, or implants that have surfaces that are not smooth. In another embodiment, the solution can be prepared in association with a structural insert such as an orthopedic, urological or vascular implant. In another embodiment, these inserts comprise at least one biocompatible material and may have a non-absorbability and/or absorbability aspect.

The type of pore morphology that becomes locked-in during the removal of the non-polymeric material and which is present in the reticulated elastomeric matrix remaining thereafter is a function of, e.g., the solution thermodynamics, freezing rate and temperature to which the solution is cooled, polymer concentration in the solution and type of nucleation, e.g., homogeneous or heterogeneous. In one embodiment, a lyophilizer for the polymer solution is cooled to −70° C. In another embodiment, the lyophilizer for the polymer solution is cooled to −40° C. In one embodiment, the lyophilizer comprises a shelf onto which the polymer solution is placed and the shelf is cooled to −70° C. In another embodiment, the shelf is cooled to −40° C. The rate of cooling to freeze the polymer solution can be from about 0.2° C./min to about 2.5° C./min.

At the start of the lyophilization process of one embodiment, the polymer solution is placed into a mold and the mold is placed into the lyophilizer. The walls of the mold undergo cooling in the lyophilizer, e.g., as they contact the freeze-dryer shelf. The temperature of the lyophilizer is reduced at the desired cooling rate until the final cooling temperature is attained. For example, in a lyophilizer where the mold is placed onto a cooled shelf, the heat transfer front moves upwards from the lyophilizer shelf through the mold wall into the polymer solution. The rate at which this front advances influences the nucleation and the orientation of the frozen structure. This rate depends on, e.g., the cooling rate and the thermal conductivity of the mold. When the temperature of the solution goes below the gellation and/or freezing point of the solvent, the solution can phase separate into a continuous phase and a dispersed phase or into two bicontinuous phases, as discussed previously. The morphology of the phase separated system is locked into place during the freezing step of the lyophilization process. The creation of pores is initiated by the sublimation of the solvent upon exposing the frozen material to reduced pressure.

Without being bound by any particular theory, in general, a higher concentration of the polymer in the solution, higher viscosity (attributable to higher concentration or higher molecular weight of the polymer) or higher cooling rate are thought to lead to smaller pore sizes while lower concentration of the polymer in the solution, lower viscosity (attributable to lower concentration or lower molecular weight of the polymer) or slower cooling rate are thought to lead to larger pore sizes in the lyophilized products.

The lyophilization process is further exemplified in Example 17.

Imparting Endopore Features

Within pores 20, elastomeric matrix 10 may, optionally, have features in addition to the void or gas-filled volume described above. In one embodiment, elastomeric matrix 10 may have what are referred to herein as "endopore" features as part of its microstructure, i.e., features of elastomeric matrix 10 that are located "within the pores". In one embodiment, the internal surfaces of pores 20 may be "endoporously coated", i.e., coated or treated to impart to those surfaces a degree of a desired characteristic, e.g., hydrophilicity. The coating or treating medium can have additional capacity to transport or bond to active ingredients that can then be preferentially delivered to pores 20. In one embodiment, this coating medium or treatment can be used facilitate covalent bonding of materials to the interior pore surfaces, for example, as are described in the applications to which priority is claimed. In another embodiment, the coating comprises a biodegradable polymer and an inorganic component, such as hydroxyapatite. Hydrophilic treatments may be effected by chemical or radiation treatments on the fabricated reticulated elastomeric matrix 10, by exposing the elastomer to a hydrophilic, e.g., aqueous, environment during elastomer setting, or by other means known to those skilled in the art.

Furthermore, one or more coatings may be applied endoporously by contacting with a film-forming biocompatible polymer either in a liquid coating solution or in a melt state under conditions suitable to allow the formation of a biocompatible polymer film. In one embodiment, the polymers used for such coatings are film-forming biocompatible polymers with sufficiently high molecular weight so as not to be waxy or tacky. The polymers should also adhere to the solid phase 12. In another embodiment, the bonding strength is such that the polymer film does not crack or dislodge during handling or deployment of reticulated elastomeric matrix 10.

Suitable biocompatible polymers include polyamides, polyolefins (e.g., polypropylene, polyethylene), nonabsorbable polyesters (e.g., polyethylene terephthalate), and bioabsorbable aliphatic polyesters (e.g., homopolymers and copolymers of lactic acid, glycolic acid, lactide, glycolide, para-dioxanone, trimethylene carbonate, ε-caprolactone or a mixture thereof). Further, biocompatible polymers include film-forming bioabsorbable polymers; these include aliphatic polyesters, poly(amino acids), copoly(ether-esters), polyalkylenes oxalates, polyamides, poly(iminocarbonates), polyorthoesters, polyoxaesters including polyoxaesters containing amido groups, polyamidoesters, polyanhydrides, polyphosphazenes, biomolecules or a mixture thereof. For the purpose of this invention aliphatic polyesters include polymers and copolymers of lactide (which includes lactic acid d-, 1- and meso lactide), ε-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one or a mixture thereof.

Biocompatible polymers further include film-forming biodurable polymers with relatively low chronic tissue response, such as polyurethanes, silicones, poly(meth)acrylates, polyesters, polyalkyl oxides (e.g., polyethylene oxide), polyvinyl alcohols, polyethylene glycols and polyvinyl pyrrolidone, as well as hydrogels, such as those formed from crosslinked polyvinyl pyrrolidinone and polyesters. Other polymers can also be used as the biocompatible polymer provided that they can be dissolved, cured or polymerized. Such polymers and copolymers include polyolefins, polyisobutylene and ethylene-α-olefin copolymers; acrylic polymers (including methacrylates) and copolymers; vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile; polyvinyl ketones; polyvinyl aromatics such as polystyrene; polyvinyl esters such as polyvinyl acetate; copolymers of vinyl monomers with each other and with α-olefins, such as etheylene-methyl methacrylate copolymers and ethylene-vinyl acetate copolymers; acrylonitrile-styrene copolymers; ABS resins; polyamides, such as nylon 66 and polycaprolactam; alkyd resins; polycarbonates; polyoxymethylenes; polyimides; polyethers; epoxy resins; polyurethanes; rayon; rayon-triacetate; cellophane; cellulose and its derivatives such as cellulose acetate, cellulose acetate butyrate, cellulose nitrate, cellulose propionate and cellulose ethers (e.g., carboxymethyl cellulose and hydoxyalkyl celluloses); or a mixture thereof. For the purpose of this invention, polyamides include polyamides of the general forms:

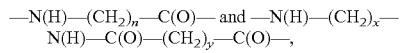

where n is an integer from about 4 to about 13; x is an integer from about 4 to about 12; and y is an integer from about 4 to about 16. It is to be understood that the listings of materials above are illustrative but not limiting.

A device made from reticulated elastomeric matrix 10 generally is coated by simple dip or spray coating with a polymer, optionally comprising a pharmaceutically-active agent, such as a therapeutic agent or drug. In one embodiment, the coating is a solution and the polymer content in the coating solution is from about 1% to about 40% by weight. In another embodiment, the polymer content in the coating solution is from about 1% to about 20% by weight. In another embodiment, the polymer content in the coating solution is from about 1% to about 10% by weight.

The solvent or solvent blend for the coating solution is chosen with consideration given to, inter alia, the proper balancing of viscosity, deposition level of the polymer, wetting rate and evaporation rate of the solvent to properly coat solid phase 12, as known to those in the art. In one embodiment, the solvent is chosen such the polymer is soluble in the solvent. In another embodiment, the solvent is substantially completely removed from the coating. In another embodiment, the solvent is non-toxic, non-carcinogenic and environmentally benign. Mixed solvent systems can be advantageous for controlling the viscosity and evaporation rates. In all cases, the solvent should not react with the coating polymer. Solvents include by are not limited to: acetone, N-methylpyrrolidone ("NMP"), DMSO, toluene, methylene chloride, chloroform, 1,1,2-trichloroethane ("TCE"), various freons, dioxane, ethyl acetate, THF, DMF and DMAC.

In another embodiment, the film-forming coating polymer is a thermoplastic polymer that is melted, enters the pores 20 of the elastomeric matrix 10 and, upon cooling or solidifying, forms a coating on at least a portion of the solid material 12 of the elastomeric matrix 10. In another embodiment, the processing temperature of the thermoplastic coating polymer in its melted form is above about 60° C. In another embodiment, the processing temperature of the thermoplastic coating polymer in its melted form is above about 90° C. In another embodiment, the processing temperature of the thermoplastic coating polymer in its melted form is above about 120° C.

In a further embodiment of the invention, described in more detail below, some or all of the pores 20 of elastomeric matrix 10 are coated or filled with a cellular ingrowth promoter. In another embodiment, the promoter can be foamed. In another embodiment, the promoter can be present as a film. The promoter can be a biodegradable material to promote cellular invasion of elastomeric matrix 10 in vivo. Promoters include naturally occurring materials that can be enzymatically degraded in the human body or are hydrolytically unstable in the human body, such as fibrin, fibrinogen, collagen, elastin, hyaluronic acid and absorbable biocompatible polysaccharides, such as chitosan, starch, fatty acids (and esters thereof), glucoso-glycans and hyaluronic acid. In some embodiments, the pore surface of elastomeric matrix 10 is coated or impregnated, as described in the previous section but substituting the promoter for the biocompatible polymer or adding the promoter to the biocompatible polymer, to encourage cellular ingrowth and proliferation.

In one embodiment, the coating or impregnating process is conducted so as to ensure that the product "composite elastomeric implantable device", i.e., a reticulated elastomeric matrix and a coating, as used herein, retains sufficient resiliency after compression such that it can be delivery-device delivered, e.g., catheter, syringe or endoscope delivered. Some embodiments of such a composite elastomeric implantable device will now be described with reference to collagen, by way of non-limiting example, with the understanding that other materials may be employed in place of collagen, as described above.

One embodiment of the invention is a process for preparing a composite elastomeric implantable device comprising:

a) infiltrating an aqueous collagen slurry into the pores of a reticulated, porous elastomer, such as elastomeric matrix 10, which is optionally a biodurable elastomer product; and b) removing the water, optionally by lyophilizing, to provide a collagen coating, where the collagen coating optionally comprises an interconnected network of pores, on at least a portion of a pore surface of the reticulated, porous elastomer.

Collagen may be infiltrated by forcing, e.g., with pressure, an aqueous collagen slurry, suspension or solution into the pores of an elastomeric matrix. The collagen may be Type I, II or III or a mixture thereof. In one embodiment, the collagen type comprises at least 90% collagen I. The concentration of collagen is from about 0.3% to about 2.0% by weight and the pH of the slurry, suspension or solution is adjusted to be from about 2.6 to about 5.0 at the time of lyophilization. Alternatively, collagen may be infiltrated by dipping an elastomeric matrix into a collagen slurry.

As compared with the uncoated reticulated elastomer, the composite elastomeric implantable device can have a void phase 14 that is slightly reduced in volume. In one embodiment, the composite elastomeric implantable device retains good fluid permeability and sufficient porosity for ingrowth and proliferation of fibroblasts or other cells.

Optionally, the lyophilized collagen can be crosslinked to control the rate of in vivo enzymatic degradation of the collagen coating and/or to control the ability of the collagen coating to bond to elastomeric matrix 10. The collagen can be crosslinked by methods known to those in the art, e.g., by heating in an evacuated chamber, by heating in a substantially moisture-free inert gas atmosphere, by bring the collagen into contact with formaldehyde vapor, or by the use of glutaraldehyde. Without being bound by any particular theory, it is thought that when the composite elastomeric implantable device is implanted, tissue-forming agents that have a high affinity to collagen, such as fibroblasts, will more readily invade the collagen-impregnated elastomeric matrix 10 than the uncoated matrix. It is further thought, again without being bound by any particular theory, that as the collagen enzymatically degrades, new tissue invades and fills voids left by the degrading collagen while also infiltrating and filling other available spaces in the elastomeric matrix 10. Such a collagen coated or impregnated elastomeric matrix 10 is thought, without being bound by any particular theory, to be additionally advantageous for the structural integrity provided by the reinforcing effect of the collagen within the pores 20 of the elastomeric matrix 10, which can impart greater rigidity and structural stability to various configurations of elastomeric matrix 10.

Processes of preparing a collagen-coated composite elastomeric implantable device is exemplified in Examples 5 and 11. Other processes will be apparent to those skilled in the art.

Coated Implantable Devices

In some applications, a device made from elastomeric matrix 10 can have at least a portion of the outermost or macro surface coated or fused in order to present a smaller macro surface area, because the internal surface area of pores below the surface is no longer accessible. Without being bound by any particular theory, it is thought that this decreased surface area provides more predictable and easier delivery and transport through long tortuous channels inside delivery-devices. Surface coating or fusion alters the "porosity of the surface", i.e., at least partially reduces the percentage of pores open to the surface, or, in the limit, completely closes-off the pores of a coated or fused surface, i.e., that surface is nonporous because it has substantially no pores remaining on the coated or fused surface. However, surface coating or fusion still allows the internal interconnected porous structure of elastomeric matrix 10 to remain open internally and on other non-coated or non-fused surfaces; e.g., the portion of a coated or fused pore not at the surface remains interconnected to other pores, and those remaining open surfaces can foster cellular ingrowth and proliferation. In one embodiment, a coated and uncoated surface are orthogonal to each other. In another embodiment, a coated and uncoated surface are at an oblique angle to each other. In another embodiment, a coated and uncoated surface are adjacent. In another embodiment, a coated and uncoated surface are nonadjacent. In another embodiment, a coated and uncoated surface are in contact with each other. In another embodiment, a coated and uncoated surface are not in contact with each other.

In other applications, one or more planes of the macro surface of an implantable device made from reticulated elastomeric matrix 10 may be coated, fused or melted to improve its attachment efficiency to attaching means, e.g., anchors or sutures, so that the attaching means does not tear-through or pull-out from the implantable device. Without being bound by any particular theory, creation of additional contact anchoring macro surface(s) on the implantable device, as described above, is thought to inhibit tear-through or pull-out by providing fewer voids and greater resistance.

The fusion and/or selective melting of the macro surface layer of elastomeric matrix 10 can be brought about in several different ways. In one embodiment, a knife or a blade used to cut a block of elastomeric matrix 10 into sizes and shapes for making final implantable devices can be heated to an elevated temperature, for example, as exemplified in Example 8. In another embodiment, a device of desired shape and size is cut from a larger block of elastomeric matrix 10 by using a laser cutting device and, in the process, the surfaces that come into contact with the laser beam are fused. In another embodiment, a cold laser cutting device is used to cut a device of desired shape and size. In yet another embodiment, a heated mold can be used to impart the desired size and shape to the device by the process of heat compression. A slightly oversized elastomeric matrix 10, cut from a larger block, can be placed into a heated mold. The mold is closed over the cut piece to reduce its overall dimensions to the desired size and shape and fuse those surfaces in contact with the heated mold, for example, as exemplified in Example 9. In each of the aforementioned embodiments, the processing temperature for shaping and sizing is greater than about 15° C. in one embodiment. In another embodiment, the processing temperature for shaping and sizing is in excess of about 100° C. In another embodiment, the processing temperature for shaping and sizing is in excess of about 130° C. In another embodiment, the layer(s) and/or portions of the macro surface not being fused are protected from exposure by covering them during the fusing of the macro surface.

The coating on the macro surface can be made from a biocompatible polymer, which can include be both biodegradable and non-biodegradable polymers. Suitable biocompatible polymers include those biocompatible polymers disclosed in the previous section. It is to be understood that that listing of materials is illustrative but not limiting. In one embodiment, surface pores are closed by applying an absorbable polymer melt coating onto a shaped elastomeric matrix. Together, the elastomeric matrix and the coating form the device. In another embodiment, surface pores are closed by applying an absorbable polymer solution coating onto a shaped elastomeric matrix to form a device. In another embodiment, the coating and the elastomeric matrix, taken together, occupy a larger volume than the uncoated elastomeric matrix alone.

The coating on elastomeric matrix 10 can be applied by, e.g., dipping or spraying a coating solution comprising a polymer or a polymer that is admixed with a pharmaceutically-active agent. In one embodiment, the polymer content in the coating solution is from about 1% to about 40% by weight. In another embodiment, the polymer content in the coating solution is from about 1% to about 20% by weight. In another embodiment, the polymer content in the coating solution is from about 1% to about 10% by weight. In another embodiment, the layer(s) and/or portions of the macro surface not being solution-coated are protected from exposure by covering them during the solution-coating of the macro surface. The solvent or solvent blend for the coating solution is chosen, e.g., based on the considerations discussed in the previous section (i.e., in the "Imparting Endopore Features" section).

In one embodiment, the coating on elastomeric matrix 10 may be applied by melting a film-forming coating polymer and applying the melted polymer onto the elastomeric matrix 10 by dip coating, for example, as exemplified in Example 10. In another embodiment, the coating on elastomeric matrix 10 may be applied by melting the film-forming coating polymer and applying the melted polymer through a die, in a process such as extrusion or coextrusion, as a thin layer of melted polymer onto a mandrel formed by elastomeric matrix 10. In either of these embodiments, the melted polymer coats the macro surface and bridges or plugs pores of that surface but does not penetrate into the interior to any significant depth. Without being bound by any particular theory, this is thought to be due to the high viscosity of the melted polymer. Thus, the reticulated nature of portions of the elastomeric matrix removed from the macro surface, and portions of the elastomeric matrix's macro surface not in contact with the melted polymer, is maintained. Upon cooling and solidifying, the melted polymer forms a layer of solid coating on the elastomeric matrix 10. In one embodiment, the processing temperature of the melted thermoplastic coating polymer is at least about 60° C. In another embodiment, the processing temperature of the melted thermoplastic coating polymer is at least above about 90° C. In another embodiment, the processing temperature of the melted thermoplastic coating polymer is at least above about 120° C.

In another embodiment, the layer(s) and/or portions of the macro surface not being melt-coated are protected from exposure by covering them during the melt-coating of the macro surface.

Another embodiment of the invention employs a collagen-coated composite elastomeric implantable device, as described above, configured as a sleeve extending around the implantable device. The collagen matrix sleeve can be implanted at a tissue repair and regeneration site, either adjacent to and in contact with that site. So located, the collagen matrix sleeve can be useful to help retain the elastomeric matrix 10, facilitate the formation of a tissue seal and help prevent leakage. The presence of the collagen in elastomeric matrix 10 can enhance cellular ingrowth and proliferation and improve mechanical stability, in one embodiment, by enhancing the attachment of fibroblasts to the collagen. The presence of collagen can stimulate earlier and/or more complete infiltration of the interconnected pores of elastomeric matrix 10.

Tissue Culture

The biodurable reticulated elastomeric matrix of this invention can support cell types including cells secreting structural proteins and cells that produce proteins characterizing organ function. The ability of the elastomeric matrix to facilitate the co-existence of multiple cell types together and its ability to support protein secreting cells demonstrates the applicability of the elastomeric matrix in organ growth in vitro or in vivo and in organ reconstruction. In addition, the biodurable reticulated elastomeric matrix may also be used in the scale up of human cell lines for implantation to the body for many applications including implantation of fibroblasts, chondrocytes, osteoblasts, osteoclasts, osteocytes, synovial cells, bone marrow stromal cells, stem cells, fibrocartilage cells, endothelial cells, smooth muscle cells, adipocytes, cardiomyocytes, myocytes, keratinocytes, hepatocytes, leukocytes, macrophages, endocrine cells, genitourinary cells, lymphatic vessel cells, pancreatic islet cells, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, epithelial cells, nerve cells, stem cells, progenitor cells, myoblasts and intestinal cells.

The approach to engineer new tissue can be obtained through implantation of cells seeded in elastomeric matrices (either prior to or concurrent to or subsequent to implantation). In this case, the elastomeric matrices may be configured either in a closed manner to protect the implanted cells from the body's immune system, or in an open manner so that the new cells can be incorporated into the body. Thus in another embodiment, the cells may be incorporated, i.e. cultured and proliferated, onto the elastomeric matrix prior, concurrent or subsequent to implantation of the elastomeric matrix in the patient.

In one embodiment, the implantable device made from biodurable reticulated elastomeric matrix can be seeded with a type of cell and cultured before being inserted into the patient, optionally using a delivery-device, for the explicit purpose of tissue repair or tissue regeneration. It is necessary to perform the tissue or cell culture in a suitable culture medium with or without stimulus such as stress or orientation. The cells include fibroblasts, chondrocytes, osteoblasts, osteoclasts, osteocytes, synovial cells, bone marrow stromal cells, stem cells, fibrocartilage cells, endothelial cells and smooth muscle cells.

Surfaces on the biodurable reticulated elastomeric matrix possessing different pore morphology, size, shape and orientation may be cultured with different type of cells to develop cellular tissue engineering implantable devices that are specifically targeted towards orthopedic applications, especially in soft tissue attachment, repair, regeneration, augmentation and/or support encompassing the spine, shoulder, knee, hand or joints, and in the growth of a prosthetic organ. In another embodiment, all the surfaces on the biodurable reticulated elastomeric matrix possessing similar pore morphology, size, shape and orientation may be so cultured.

In other embodiments, the biodurable reticulated elastomeric matrix of this invention may have applications in the areas of mammary prostheses, pacemaker housings, LVAD bladders or as a tissue bridging matrix.

Pharmaceutically-Active Agent Delivery

In another embodiment, the film-forming polymer used to coat reticulated elastomeric matrix 10 can provide a vehicle for the delivery of and/or the controlled release of a pharmaceutically-active agent, for example, a drug, such as is described in the applications to which priority is claimed. In another embodiment, the pharmaceutically-active agent is admixed with, covalently bonded to and/or adsorbed in or on the coating of elastomeric matrix 10 to provide a pharmaceutical composition. In another embodiment, the components, polymers and/or blends used to form the foam comprise a pharmaceutically-active agent. To form these foams, the previously described components, polymers and/or blends are admixed with the pharmaceutically-active agent prior to forming the foam or the pharmaceutically-active agent is loaded into the foam after it is formed.

In one embodiment, the coating polymer and pharmaceutically-active agent have a common solvent. This can provide a coating that is a solution. In another embodiment, the pharmaceutically-active agent can be present as a solid dispersion in a solution of the coating polymer in a solvent.

A reticulated elastomeric matrix 10 comprising a pharmaceutically-active agent may be formulated by mixing one or more pharmaceutically-active agent with the polymer used to make the foam, with the solvent or with the polymer-solvent mixture and foamed. Alternatively, a pharmaceutically-active agent can be coated onto the foam, in one embodiment, using a pharmaceutically-acceptable carrier. If melt-coating is employed, then, in another embodiment, the pharmaceutically-active agent withstands melt processing temperatures without substantial diminution of its efficacy.

Formulations comprising a pharmaceutically-active agent can be prepared by admixing, covalently bonding and/or adsorbing one or more pharmaceutically-active agents with the coating of the reticulated elastomeric matrix 10 or by incorporating the pharmaceutically-active agent into additional hydrophobic or hydrophilic coatings. The pharmaceutically-active agent may be present as a liquid, a finely divided solid or another appropriate physical form. Typically, but optionally, the matrix can include one or more conventional additives, such as diluents, carriers, excipients, stabilizers and the like.

In another embodiment, a top coating can be applied to delay release of the pharmaceutically-active agent. In another embodiment, a top coating can be used as the matrix for the delivery of a second pharmaceutically-active agent. A layered coating, comprising respective layers of fast- and slow-hydrolyzing polymer, can be used to stage release of the pharmaceutically-active agent or to control release of different pharmaceutically-active agents placed in the different layers. Polymer blends may also be used to control the release rate of different pharmaceutically-active agents or to provide a desirable balance of coating characteristics (e.g., elasticity, toughness) and drug delivery characteristics (e.g., release profile). Polymers with differing solvent solubilities can be used to build-up different polymer layers that may be used to deliver different pharmaceutically-active agents or to control the release profile of a pharmaceutically-active agents.

The amount of pharmaceutically-active agent present depends upon the particular pharmaceutically-active agent employed and medical condition being treated. In one embodiment, the pharmaceutically-active agent is present in an effective amount. In another embodiment, the amount of pharmaceutically-active agent represents from about 0.01% to about 60% of the coating by weight. In another embodiment, the amount of pharmaceutically-active agent represents from about 0.01% to about 40% of the coating by weight. In another embodiment, the amount of pharmaceutically-active agent represents from about 0.1% to about 20% of the coating by weight.

Many different pharmaceutically-active agents can be used in conjunction with the reticulated elastomeric matrix. In general, pharmaceutically-active agents that may be administered via pharmaceutical compositions of this invention include, without limitation, any therapeutic or pharmaceutically-active agent (including but not limited to nucleic acids, proteins, lipids, and carbohydrates) that possesses desirable physiologic characteristics for application to the implant site or administration via a pharmaceutical compositions of the invention. Therapeutics include, without limitation, antiinfectives such as antibiotics and antiviral agents; chemotherapeutic agents (e.g., anticancer agents); anti-rejection agents; analgesics and analgesic combinations; anti-inflammatory agents; hormones such as steroids; growth factors (including but not limited to cytokines, chemokines, and interleukins) and other naturally derived or genetically engineered proteins, polysaccharides, glycoproteins and lipoproteins. These growth factors are described in The Cellular and Molecular Basis of Bone Formation and Repair by Vicki Rosen and R. Scott Thies, published by R. G. Landes Company, hereby incorporated herein by reference. Additional therapeutics include thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroids, non-steroidal anti-inflammatory agents, immunosuppressive agents, growth hormone antagonists, growth factors, dopamine agonists, radiotherapeutic agents, peptides, proteins, enzymes, extracellular matrix components, angiotensin-converting enzyme (ACE) inhibitors, free radical scavengers, chelators, antioxidants, anti polymerases, antiviral agents, photodynamic therapy agents and gene therapy agents.

Additionally, various proteins (including short chain peptides), growth agents, chemotatic agents, growth factor receptors or ceramic particles can be added to the foams during processing, adsorbed onto the surface or back-filled into the foams after the foams are made. For example, in one embodiment, the pores of the foam may be partially or completely filled with biocompatible resorbable synthetic polymers or biopolymers (such as collagen or elastin), biocompatible ceramic materials (such as hydroxyapatite), and combinations thereof, and may optionally contain materials that promote tissue growth through the device. Such tissue-growth materials include but are not limited to autograft, allograft or xenograft bone, bone marrow and morphogenic proteins. Biopolymers can also be used as conductive or chemotactic materials, or as delivery vehicles for growth factors. Examples include recombinant collagen, animal-derived collagen, elastin and hyaluronic acid. Pharmaceutically-active coatings or surface treatments could also be present on the surface of the materials. For example, bioactive peptide sequences (RGD's) could be attached to the surface to facilitate protein adsorption and subsequent cell tissue attachment.

Bioactive molecules include, without limitation, proteins, collagens (including types IV and XVIII), fibrillar collagens (including types I, II, III, V, XI), FACIT collagens (types IX, XII, XIV), other collagens (types VI, VII, XIII), short chain collagens (types VIII, X), elastin, entactin-1, fibrillin, fibronectin, fibrin, fibrinogen, fibroglycan, fibromodulin, fibulin, glypican, vitronectin, laminin, nidogen, matrilin, perlecan, heparin, heparan sulfate proteoglycans, decorin, filaggrin, keratin, syndecan, agrin, integrins, aggrecan, biglycan, bone sialoprotein, cartilage matrix protein, Cat-301 proteoglycan, CD44, cholinesterase, HB-GAM, hyaluronan, hyaluronan binding proteins, mucins, osteopontin, plasminogen, plasminogen activator inhibitors, restrictin, serglycin, tenascin, thrombospondin, tissue-type plasminogen activator, urokinase type plasminogen activator, versican, von Willebrand factor, dextran, arabinogalactan, chitosan, polyactideglycolide, alginates, pullulan, gelatin and albumin.

Additional bioactive molecules include, without limitation, cell adhesion molecules and matricellular proteins, including those of the immunoglobulin (Ig; including monoclonal and polyclonal antibodies), cadherin, integrin, selectin, and H-CAM superfamilies. Examples include, without limitation, AMOG, CD2, CD4, CD8, C-CAM (CELL-CAM 105), cell surface galactosyltransferase, connexins, desmocollins, desmoglein, fasciclins, F11, GP Ib-IX complex, intercellular adhesion molecules, leukocyte common antigen protein tyrosine phosphate (LCA, CD45), LFA-1, LFA-3, mannose binding proteins (MBP), MTJC18, myelin associated glycoprotein (MAG), neural cell adhesion molecule (NCAM), neurofascin, neruoglian, neurotactin, netrin, PECAM-1, PH-20, semaphorin, TAG-1, VCAM-1, SPARC/osteonectin, CCN1 (CYR61), CCN2 (CTGF; Connective Tissue Growth Factor), CCN3 (NOV), CCN4 (WISP-1), CCN5 (WISP-2), CCN6 (WISP-3), occludin and claudin. Growth factors include, without limitation, BMP's (1-7), BMP-like Proteins (GFD-5, -7, -8), epidermal growth factor (EGF), erythropoietin (EPO), fibroblast growth factor (FGF), growth hormone (GH), growth hormone releasing factor (GHRF), granulocyte colony-stimulating factor (G-CSF), granulocyte-macrophage colony-stimulating factor (GM-CSF), insulin, insulin-like growth factors (IGF-I, IGF-II), insulin-like growth factor binding proteins (IGFBP), macrophage colony-stimulating factor (M-CSF), Multi-CSF (Il-3), platelet-derived growth factor (PDGF), tumor growth factors (TGF-alpha, TGF-beta), tumor necrosis factor (TNF-alpha), vascular endothelial growth factors (VEGF's), angiopoietins, placenta growth factor (PlGF), interleukins, and receptor proteins or other molecules that are known to bind with the aforementioned factors. Short-chain peptides include, without limitation (designated by single letter amino acid code), RGD, EILDV, RGDS, RGES, RFDS, GRDGS, GRGS, GRGDTP and QPPRARI.

Other Post-Processing of the Reticulated Elastomeric Matrix

Elastomeric matrix 10 can undergo a further processing step or steps, in addition to reticulation and imparting endpore features, already discussed above. For example, elastomeric matrix 10 may be endoporously hydrophilized, as described above, by post treatments or by placing the elastomeric matrix in a hydrophilic environment, to render its microstructural surfaces chemically more reactive. In another embodiment, biologically useful compounds, or controlled release formulations containing them, may be attached to the endoporous surfaces for local delivery and release, embodiments which are described in the applications to which priority is claimed.

In another embodiment, the products made from elastomeric matrix 10 of the invention can be annealed to stabilize the structure. Annealing at elevated temperatures can promote crystallinity in semi-crystalline polyurethanes. The structural stabilization and/or additional crystallinity can provide enhanced shelf-life stability to implantable-devices made from elastomeric matrix 10. In one embodiment, annealing is carried out at temperatures in excess of about 50° C. In another embodiment, annealing is carried out at temperatures in excess of about 100° C. In another embodiment, annealing is carried out at temperatures in excess of about 125° C. In another embodiment, annealing is carried out for at least about 2 hours. In another embodiment, annealing is carried out for from about 4 to about 8 hours. In crosslinked polyurethanes, curing at elevated temperatures can also promote structural stabilization and long-term shelf-life stability.

Elastomeric matrix 10 may be molded into any of a wide variety of shapes and sizes during its formation or production. The shape may be a working configuration, such as any of the shapes and configurations described in the applications to which priority is claimed, or the shape may be for bulk stock. Stock items may subsequently be cut, trimmed, punched or otherwise shaped for end use. The sizing and shaping can be carried out by using a blade, punch, drill or laser, for example. In each of these embodiments, the processing temperature or temperatures of the cutting tools for shaping and sizing can be greater than about 100° C. In another embodiment, the processing temperature(s) of the cutting tools for shaping and sizing can be greater than about 130° C. Finishing steps can include, in one embodiment, trimming of macrostructural surface protrusions, such as struts or the like, which can irritate biological tissues. In another embodiment, finishing steps can include heat annealing. Annealing can be carried out before or after final cutting and shaping.

Shaping and sizing can include custom shaping and sizing to match an implantable device to a specific treatment site in a specific patient, as determined by imaging or other techniques known to those in the art. In particular, one or a small number, e.g. less than about 6 in one embodiment and less than about 2 in another embodiment, of elastomeric matrices 10 can comprise an implantable device system for treating damaged tissue requiring repair and/or regeneration.

The dimensions of the shaped and sized devices made from elastomeric matrix 10 can vary depending on the particular tissue repair and regeneration site treated. In one embodiment, the major dimension of a device prior to being compressed and delivered is from about 0.5 mm to about 500 mm. In another embodiment, the major dimension of a device prior to being compressed and delivered is from about 10 mm to about 500 mm. In another embodiment, the major dimension of a device prior to being compressed and delivered is from about 50 mm to about 200 mm. In another embodiment, the major dimension of a device prior to being compressed and delivered is from about 30 mm to about 100 mm. Elastomeric matrix 10 can exhibit compression set upon being compressed and transported through a delivery-device, e.g., a catheter, syringe or endoscope. In another embodiment, compression set and its standard deviation are taken into consideration when designing the pre-compression dimensions of the device.

In one embodiment, a patient is treated using an implantable device or a device system that does not, in and of itself, entirely fill the target cavity or other site in which the device system resides, in reference to the volume defined within the entrance to the site. In one embodiment, the implantable device or device system does not entirely fill the target cavity or other site in which the implant system resides even after the elastomeric matrix pores are occupied by biological fluids or tissue. In another embodiment, the fully expanded in situ volume of the implantable device or device system is at least 1% less than the volume of the site. In another embodiment, the fully expanded in situ volume of the implantable device or device system is at least 15% less than the volume of the site. In another embodiment, the fully expanded in situ volume of the implantable device or device system is at least 30% less than the volume of the site.

In another embodiment, the fully-expanded in situ volume of the implantable device or device system is from about 1% to about 40% larger than the volume of the cavity. In another embodiment, the fully-expanded in situ volume of the implantable device or device system is from about 5% to about 25% larger than the volume of the cavity. In another embodiment, the ratio of implantable device volume to the volume occupied by the orthopedic application site is from about 70% to about 90%. In another embodiment, the ratio of implantable device volume to the volume occupied by the orthopedic application site is from about 90% to about 100%. In another embodiment, the ratio of implantable device volume to the volume occupied by the orthopedic application site is from about 90% to less than about 100%. In another embodiment, the ratio of implantable device volume to the volume occupied by the orthopedic application site is from about 100% to about 140%. In another embodiment, the ratio of implantable device volume to the volume occupied by the orthopedic application site is from about 100% to about 200%. In another embodiment, the ratio of implantable device volume to the volume occupied by the orthopedic application site is from about 100% to about 300%.

The implantable device or device system may comprise one or more elastomeric matrices 10 that occupy a central location in the treatment site. In one embodiment, the implantable device or device system may comprise one or more elastomeric matrices 10 that are located at an entrance or portal to the site. In another embodiment, the implantable device or device system may comprise one or more elastomeric matrices 10 that span and cover the damaged tissue. In another embodiment, the implantable device or device system includes one or more flexible, possibly sheet-like, elastomeric matrices 10. In another embodiment, such elastomeric matrices, aided by suitable hydrodynamics at the site of implantation, migrate to lie adjacent to the cavity wall.

Biodurable reticulated elastomeric matrices 10, or an implantable device system comprising such matrices, can be sterilized by any method known to the art including gamma irradiation, autoclaving, ethylene oxide sterilization, infrared irradiation and electron beam irradiation. In one embodiment, biodurable elastomers used to fabricate elastomeric matrix 10 tolerate such sterilization without loss of useful physical and mechanical properties. The use of gamma irradiation can potentially provide additional crosslinking to enhance the performance of the device.

In one embodiment, the sterilized products may be packaged in sterile packages of paper, polymer or other suitable material. In another embodiment, within such packages, elastomeric matrix 10 is compressed within a retaining member to facilitate its loading into a delivery-device, such as a catheter or endoscope, in a compressed configuration. In another embodiment, elastomeric matrix 10 comprises an elastomer with a compression set enabling it to expand to a substantial proportion of its pre-compressed volume, e.g., at 25° C., to at least 50% of its pre-compressed volume. In another embodiment, expansion occurs after elastomeric matrix 10 remains compressed in such a package for typical commercial storage and distribution times, which will commonly exceed 3 months and may be up to 1 or 5 years from manufacture to use.

Radio-Opacity

In one embodiment, implantable device can be rendered radio-opaque to facilitate in vivo imaging, for example, by adhering to, covalently bonding to and/or incorporating into the elastomeric matrix itself particles of a radio-opaque material. Radio-opaque materials include titanium, tantalum, tungsten, barium sulfate or other suitable material known to those skilled in the art.

Implantable Device Uses

Reticulated elastomeric matrix 10, and implantable device systems incorporating the same, can be used as described in the applications to which priority is claimed. In one non-limiting example, one or more reticulated elastomeric matrix 10 is selected for a given site. Each, in turn, is compressed and loaded into a delivery-device, such as a catheter, endoscope, syringe or the like. The delivery-device is snaked through the vasculature or other vessel system of the intended patient host and the reticulated elastomeric matrix 10 is released from the delivery-device and anchored, e.g., sutured, onto the target repair or regeneration site. Once released at the site, reticulated elastomeric matrix 10 expands resiliently to about its original, relaxed size and shape subject, of course, to its compression set limitation and any desired flexing, draping or other conformation to the site anatomy that the implantable device may adopt. In another embodiment, the implantable device is inserted by an open surgical procedure.

In one embodiment, cellular entities such as fibroblasts and tissues can invade and grow into reticulated elastomeric matrix 10. In due course, such ingrowth can extend into the interior pores 20 and interstices of the inserted reticulated elastomeric matrix 10. Eventually, elastomeric matrix 10 can become substantially filled with proliferating cellular ingrowth that provides a mass that can occupy the site or the void spaces in it. The types of tissue ingrowth possible include, but are not limited to, fibrous tissues and endothelial tissues.

In another embodiment, the implantable device or device system causes cellular ingrowth and proliferation throughout the site, throughout the site boundary, or through some of the exposed surfaces, thereby sealing the site. Over time, this induced fibrovascular entity resulting from tissue ingrowth can cause the implantable device to be incorporated into the conduit. Tissue ingrowth can lead to very effective resistance to migration of the implantable device over time. It may also prevent recanalization of the conduit. In another embodiment, the tissue ingrowth is scar tissue which can be long-lasting, innocuous and/or mechanically stable. In another embodiment, over the course of time, for example for 2 weeks to 3 months to 1 year, implanted reticulated elastomeric matrix 10 becomes completely filled and/or encapsulated by tissue, fibrous tissue, scar tissue or the like.

Other uses of reticulated elastomeric matrix 10 include biological implantation, especially into humans, for tissue augmentation, support, regeneration and/or repair; for therapeutic purposes; or for cosmetic, reconstructive, maxillofacial, cranial, urologic, gastroesophageal or other purposes. Implantable devices fabricated from reticulated elastomeric matrix 10 may be used as tissue engineering scaffolds or other comparable substrates to support in vitro cell propagation applications in, for example, orthopedic applications such as soft tissue attachment, regeneration, augmentation or support and in the growth of prosthetic organ tissues. Reticulated elastomeric matrix 10 can be used for longer-term implantations for many applications. Demonstrated lack of carcinogenicity, mutagenicity, teratogenicity, cytotoxicity or other adverse biological effects can also be advantageous for such tissue engineering and other applications.

In another embodiment, the properties of reticulated elastomeric matrix 10 are engineered to match the tissue that is being targeted, which provides flexibility and potential for use in a number of applications. The properties of elastomeric matrices can be engineered by, e.g., controlling the amount of crosslinking, amount of crystallinity, chemical composition, chemical type of the solvent or solvent blend (when a solvent is used in processing), annealing conditions, curing conditions, and degree of reticulation. Unlike biodegradable polymers, when used as a scaffold, reticulated elastomeric matrix 10 maintains its physical characteristics and performance in vivo over long periods of time. Thus, it does not initiate undesirable tissue response as is observed for biodegradable implants when they break down and degrade. The high void content and degree of reticulation of reticulated elastomeric matrix 10 allows tissue ingrowth and proliferation of cells within the matrix. In one embodiment, the ingrown tissue and/or proliferated cells occupy from about 51% to about 99% of the volume of interconnected void phase 14 of the original implantable device, thereby providing functionality, such as load bearing capability, of the original tissue that is being repaired or replaced.

In another embodiment, the features of the implantable device and its functionality, as explained above, make it suitable for tissue engineering scaffolds for treating a number of orthopedic applications, including soft tissue attachment, regeneration, augmentation or support; and ingrowth of prosthetic organ tissues and the like, including but not limited to repair and regeneration devices encompassing the spine, shoulder, knee, hand or joints, as discussed in detail in applications to which priority is claimed.

In one embodiment, reticulated elastomeric matrix 10 can be appropriately shaped to form a closure device to seal the access opening in the annulus resulting from a discotomy in order to reinforce and stabilize the disc annulus in case of herniated disc, also known as disc prolapse or a slipped or bulging disc. The closure device can be compressed and delivered into the annulus opening by a cannula used during the discectomy procedure. The device can be secured into the opening by at least the following two mechanisms: first, the outwardly resilient nature of the reticulated solid phase 12 can provide a mechanical means for preventing migration; second, the reticulated solid phase 12 can serve as a scaffold to support fibrocartilage growth into the interconnected void phase 14 of the elastomeric matrix. Additional securing may be obtained by the use of anchors, sutures or biological glues and adhesives, as known to those in the art. The closure device can support fibrocartilage ingrowth into the elastomeric matrix of the implantable device.

In another embodiment, the implantable device made from biodurable reticulated elastomeric matrix provides a method for treating so-called hard-tissue disorders, e.g., maxillofacial or cranial tissue disorders. In another embodiment, the implantable device made from biodurable reticulated elastomeric matrix provides a method for treating so-called soft-tissue disorders, e.g., tendon augmentation, repair of articular cartilage, meniscal repair and reconstruction, anterior cruciate ligament reconstruction, stabilization of herniated disc and scaffolds for both nucleus replacement and annulus repair.

In another embodiment, reticulated elastomeric matrix 10 can be fabricated into a synthetic patch which can be anchored, e.g., by suturing into place, to provide support to tendons while they heal, allowing for in-situ tendon augmentation and reinforcement. This is particularly useful for rotator cuff or bankart repair where the tendon tissue has deteriorated and the remaining tendon is not strong enough to hold the necessary sutures for successful anchoring of tendons, where the tendons and muscles have contracted and cannot be stretched enough for reattachment (retracted tendons), or for tendons, muscles or tissues that have ruptured from an injury. The synthetic patch can serve as a scaffold for tissue ingrowth to augment the tendon and provide support during the healing process. Such an implantable device can also enable repair of otherwise inoperable tendons that cannot be reconnected without some kind of scaffold.

In another embodiment, reticulated elastomeric matrix 10 can be fabricated into a biodurable scaffold or substrate that, when implanted in an acellular mode, would serve to support tissue repair and regeneration of articular cartilage, with potential utility in knee injury treatment, e.g., for meniscal repair and anterior cruciate ligament ("ACL") reconstruction. Alternately, the implantable device can provide a basis for cell therapy applications to support tissue repair and regeneration of articular cartilage, with potential utility in meniscal repair and ACL reconstruction, for example. The biodurable implantable device can serve as a template for autologous cells harvested from a patient, which can be cultured in an ex-vivo laboratory setting and then implanted into the patient's articular cartilage defect. The ability of the implantable device to incorporate osteoinductive agents, such as growth factors, e.g., autologous growth factors derived from platelets and white blood cells, enables it to be functionalized in order to modulate cellular function and proactively induce tissue ingrowth. The resulting implantable device would fill cartilage defects, support autologous tissue repair and regeneration, and enable subsequent integration into a damaged knee.

In another embodiment, reticulated elastomeric matrix 10 can be mechanically fixed to a lesion. The reticulated elastomeric matrix can be located within, adjacent to and/or covering the target lesion. The reticulated elastomeric matrix can serve as a defect filler, replacement tissue, tissue reinforcement and/or augmentation patch. In another embodiment, the reticulated elastomeric matrix can span defects and serve as to bridge a gap in the native tissue, e.g., maxillofacial or cranial tissue.

In a further embodiment, the implantable devices disclosed herein can be used as a drug delivery vehicle. For example, the biodurable solid phase 12 can be mixed, covalently bonded to and/or adsorbed in a therapeutic agent. Any of a variety of therapeutic agents can be delivered by the implantable device, for example, those therapeutic agents previously disclosed herein.

EXAMPLES

The following examples further illustrate certain embodiments of the present invention. These examples are provided solely for illustrative purposes and in no way limit the scope of the present invention.

Example 1

Fabrication of a Crosslinked Polyurethane Matrix

The aromatic isocyanate RUBINATE 9258 (from Huntsman) was used as the isocyanate component. RUBINATE 9258 is a liquid at 25° C. RUBINATE 9258 contains 4,4'-MDI and 2,4'-MDI and has an isocyanate functionality of about 2.33. A diol, poly(1,6-hexanecarbonate)diol (POLY-CD CD220 from Arch Chemicals) with a molecular weight of about 2,000 Daltons was used as the polyol component and was a solid at 25° C. Distilled water was used as the blowing agent. The blowing catalyst used was the tertiary amine triethylenediamine (33% in dipropylene glycol; DABCO 33LV from Air Products). A silicone-based surfactant was used (TEGOSTAB® BF 2370 from Goldschmidt). A cell-opener was used (ORTEGOL® 501 from Goldschmidt). The viscosity modifier propylene carbonate (from Sigma-Aldrich) was present to reduce the viscosity. The proportions of the components that were used is given in Table 2.

TABLE 2

| Ingredient | Parts by Weight |
|---|---|
| Polyol Component | 100 |
| Viscosity Modifier | 5.80 |
| Surfactant | 0.66 |
| Cell Opener | 1.00 |
| Isocyanate Component | 47.25 |
| Isocyanate Index | 1.00 |
| Distilled Water | 2.38 |
| Blowing Catalyst | 0.53 |

The polyol component was liquefied at 70° C. in a circulating-air oven, and 100 g thereof was weighed out into a polyethylene cup. 5.8 g of viscosity modifier was added to the polyol component to reduce the viscosity and the ingredients were mixed at 3100 rpm for 15 seconds with the mixing shaft of a drill mixer to form "Mix-1". 0.66 g of surfactant was added to Mix-1 and the ingredients were mixed as described above for 15 seconds to form "Mix-2". Thereafter, 1.00 g of cell opener was added to Mix-2 and the ingredients were mixed as described above for 15 seconds to form "Mix-3". 47.25 g of isocyanate component was added to Mix-3 and the ingredients were mixed for 60±10 seconds to form "System A".

2.38 g of distilled water was mixed with 0.53 g of blowing catalyst in a small plastic cup for 60 seconds with a glass rod to form "System B".

System B was poured into System A as quickly as possible while avoiding spillage. The ingredients were mixed vigorously with the drill mixer as described above for 10 seconds then poured into a 22.9 cm×20.3 cm×12.7 cm (9 in.×8 in.×5 in.) cardboard box with its inside surfaces covered by aluminum foil. The foaming profile was as follows: 10 seconds mixing time, 17 seconds cream time, and 85 seconds rise time.

2 minutes after the beginning of foaming, i.e., the time when Systems A and B were combined, the foam was place into a circulating-air oven maintained at 100-105° C. for curing for from about 55 to about 60 minutes. Thereafter, the foam was removed from the oven and cooled for 15 minutes at about 25° C. The skin was removed from each side using a band saw. Thereafter, hand pressure was applied to each side of the foam to open the cell windows. The foam was replaced into the circulating-air oven and postcured at 100-105° C. for additional 4 hours.

The average pore diameter of the foam, as determined from optical microscopy observations, was greater than about 275 μm.

The following foam testing was carried out according to ASTM D3574. Bulk density was measured using specimens of dimensions 50 mm×50 mm×25 mm. The density was calculated by dividing the weight of the sample by the volume of the specimen. A density value of 2.81 lbs/ft$^3$ (0.0450 g/cc) was obtained.

Tensile tests were conducted on samples that were cut either parallel to or perpendicular to the direction of foam rise. The dog-bone shaped tensile specimens were cut from blocks of foam. Each test specimen measured about 12.5 mm thick, about 25.4 mm wide and about 140 mm long; the gage length of each specimen was 35 mm and the gage width of each specimen was 6.5 mm. Tensile properties (tensile strength and elongation at break) were measured using an INSTRON Universal Testing Instrument Model 1122 with a cross-head speed of 500 mm/min (19.6 inches/minute). The average tensile strength perpendicular to the direction of foam rise was determined as 29.3 psi (20,630 kg/m$^2$). The elongation to break perpendicular to the direction of foam rise was determined to be 266%.

Example 2

Reticulation of a Crosslinked Polyurethane Foam

Reticulation of the foam described in Example 1 was carried out by the following procedure. A block of foam measuring approximately 15.25 cm×15.25 cm×7.6 cm (6 in.×6 in.×3 in.) was placed into a pressure chamber, the doors of the chamber were closed, and an airtight seal to the surrounding atmosphere was maintained. The pressure within the chamber was reduced to below about 100 millitorr by evacuation for at least about 2 minutes to remove substantially all of the air in the foam. A mixture of hydrogen and oxygen gas, present at a ratio sufficient to support combustion, was charged into the chamber over a period of at least about 3 minutes. The gas in the chamber was then ignited by a spark plug. The ignition exploded the gas mixture within the foam. The explosion was believed to have at least partially removed many of the cell walls between adjoining pores, thereby forming a reticulated elastomeric matrix structure.

Figure 3:
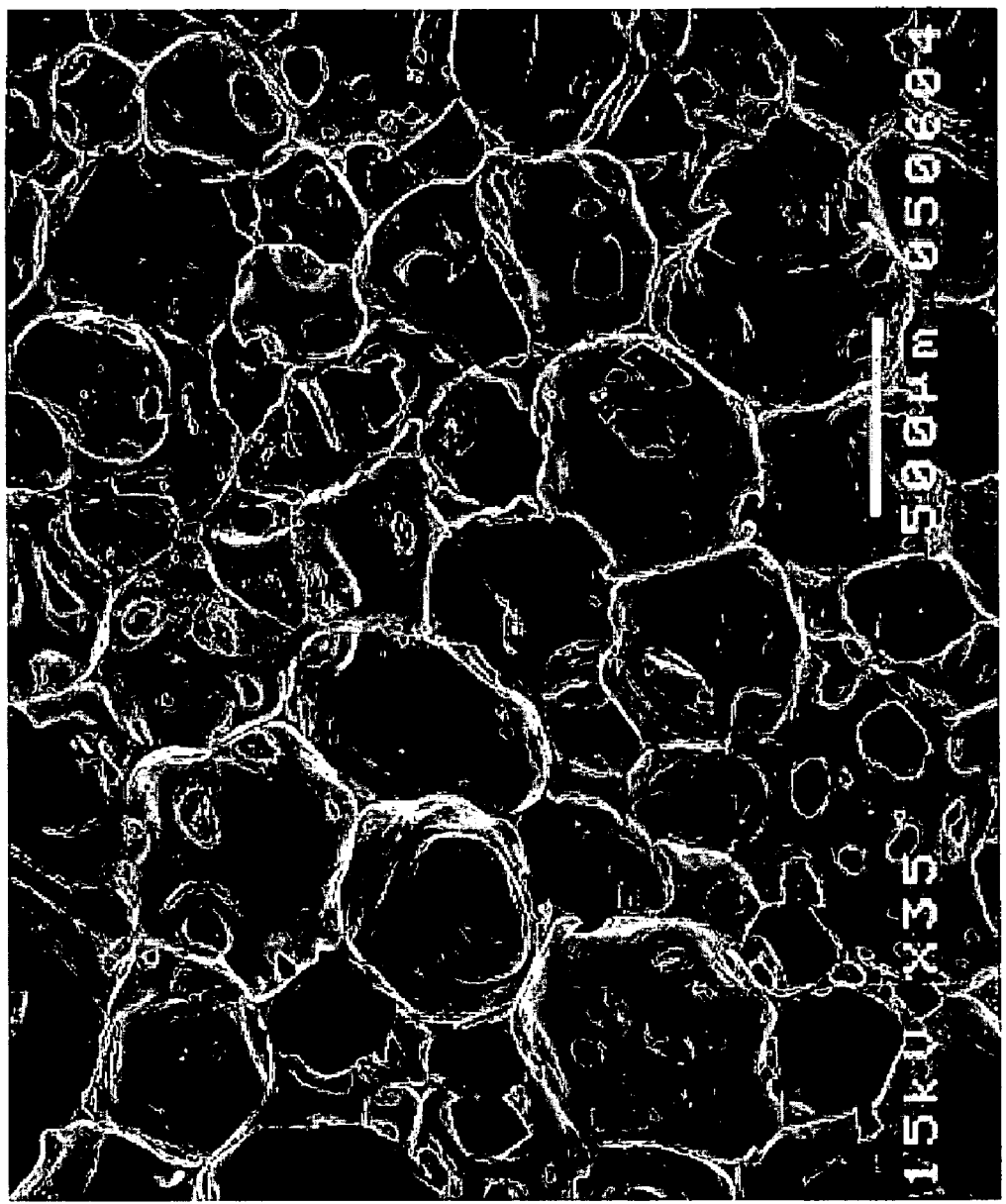
FIG. 3 is a scanning electron micrograph image of the reticulated elastomeric matrix of Example 2.

The average pore diameter of the reticulated elastomeric matrix, as determined from optical microscopy observations, was greater than about 275 μm. FIG. 3 is a scanning electron micrograph image of the reticulated elastomeric matrix of this example demonstrating, e.g., the communication and interconnectivity of pores therein.

The density of the reticulated foam was determined as described in Example 1. A post-reticulation density value of 2.83 lbs/ft$^3$ (0.0453 g/cc) was obtained.

Tensile tests were conducted on reticulated foam samples as described in Example 1. The average post-reticulation tensile strength perpendicular to the direction of foam rise was determined as about 26.4 psi (18,560 kg/m$^2$). The post-reticulation elongation to break perpendicular to the direction of foam rise was determined to be about 250%. The average post-reticulation tensile strength parallel to the direction of foam rise was determined as about 43.3 psi (30,470 kg/m$^2$). The post-reticulation elongation to break parallel to the direction of foam rise was determined to be about 270%.

Compressive tests were conducted using specimens measuring 50 mm×50 mm×25 mm. The tests were conducted using an INSTRON Universal Testing Instrument Model 1122 with a cross-head speed of 10 mm/min (0.4 inches/minute). The post-reticulation compressive strengths at 50% compression, parallel to and perpendicular to the direction of foam rise, were determined to be 1.53 psi (1,080 kg/m$^2$) and 0.95 psi (669 kg/m$^2$), respectively. The post-reticulation compressive strengths at 75% compression, parallel to and perpendicular to the direction of foam rise, were determined to be 3.53 psi (2,485 kg/m$^2$) and 2.02 psi (1,420 kg/m$^2$), respectively. The post-reticulation compression set, determined after subjecting the reticulated sample to 50% compression for 22 hours at 25° C. then releasing the compressive stress, parallel to the direction of foam rise, was determined to be about 4.5%.

The resilient recovery of the reticulated foam was measured by subjecting 1 inch (25.4 mm) diameter and 0.75 inch (19 mm) long foam cylinders to 75% uniaxial compression in their length direction for 10 or 30 minutes and measuring the time required for recovery to 90% ("t-90%") and 95% ("t-95%") of their initial length. The percentage recovery of the initial length after 10 minutes ("r-10") was also determined. Separate samples were cut and tested with their length direction parallel to and perpendicular to the foam rise direction. Table 3 shows the results obtained from an average of two tests.

TABLE 3

| Time Compressed (min) | Test Sample Orientation | t-90% (sec) | t-95% (sec) | r-10 (%) |
| --- | --- | --- | --- | --- |
| 10 | Parallel | 6 | 11 | 100 |
| 10 | Perpendicular | 6 | 23 | 100 |
| 30 | Parallel | 9 | 36 | 99 |
| 30 | Perpendicular | 11 | 52 | 99 |

In contrast, a comparable foam with little to no reticulation typically has t-90 values of greater than about 60-90 seconds after 10 minutes of compression.

Example 3

Fabrication of a Crosslinked Polyurethane Matrix

The components used were the same as described in Example 1. The proportions of the components that were used is given in Table 4.

TABLE 4

| Ingredient | Parts by Weight |
| --- | --- |
| Polyol Component | 100 |
| Viscosity Modifier | 5.80 |
| Surfactant | 1.10 |
| Cell Opener | 1.00 |
| Isocyanate Component | 62.42 |
| Isocyanate Index | 1.00 |
| Distilled Water | 3.39 |
| Blowing Catalyst | 0.53 |

The polyol component was liquefied at 70° C. in a circulating-air oven, and 100 g thereof was weighed out into a polyethylene cup. 5.8 g of viscosity modifier was added to the polyol component to reduce the viscosity and the ingredients were mixed at 3100 rpm for 15 seconds with the mixing shaft of a drill mixer to form "Mix-1". 1.10 g of surfactant was added to Mix-1 and the ingredients were mixed as described above for 15 seconds to form "Mix-2". Thereafter, 1.00 g of cell opener was added to Mix-2 and the ingredients were mixed as described above for 15 seconds to form "Mix-3". 62.42 g of isocyanate component was added to Mix-3 and the ingredients were mixed for 60±10 seconds to form "System A".

3.39 g of distilled water was mixed with 0.53 g of blowing catalyst in a small plastic cup for 60 seconds with a glass rod to form "System B".

System B was poured into System A as quickly as possible while avoiding spillage. The ingredients were mixed vigorously with the drill mixer as described above for 10 seconds then poured into a 22.9 cm×20.3 cm×12.7 cm (9 in.×8 in.×5 in.) cardboard box with its inside surfaces covered by aluminum foil. The foaming profile was as follows: 11 seconds mixing time, 27 seconds cream time, and 100 seconds rise time.

2 minutes after the beginning of foaming, i.e., the time when Systems A and B were combined, the foam was place into a circulating-air oven maintained at 100-105° C. for curing for from about 55 to about 60 minutes. Thereafter, the foam was removed from the oven and cooled for 10 minutes at about 25° C. The skin was removed from each side using a band saw. Thereafter, hand pressure was applied to each side of the foam to open the cell windows. The foam was replaced into the circulating-air oven and postcured at 100-105° C. for additional 4.5 hours.

The average pore diameter of the foam, as determined from optical microscopy observations, was greater than about 325 µm.

The density of the foam was determined as described in Example 1. A density value of 2.29 lbs/ft$^3$ (0.037 g/cc) was obtained.

Tensile tests were conducted on the foam samples as described in Example 1. The average tensile strength parallel to the direction of foam rise was determined as about 33.8 psi (23,770 kg/m$^2$). The elongation to break parallel to the direction of foam rise was determined to be about 123%. The average tensile strength perpendicular to the direction of foam rise was determined as about 27.2 psi (19,150 kg/m$^2$). The elongation to break perpendicular to the direction of foam rise was determined to be about 134%.

Example 4

Reticulation of a Crosslinked Polyurethane Foam and Fabrication of Implantable Devices Reticulation of the foam described in Example 3 was carried out by the procedure described in Example 2.

The density of the reticulated foam was determined as described in Example 1. A post-reticulation density value of 2.13 lbs/ft$^3$ (0.034 g/cc) was obtained.

Tensile tests were conducted on reticulated foam samples as described in Example 1. The average post-reticulation tensile strength parallel to the direction of foam rise was determined as about 31.1 psi (21,870 kg/m$^2$). The post-reticulation elongation to break parallel to the direction of foam rise was determined to be about 92%. The average post-reticulation tensile strength perpendicular to the direction of foam rise was determined as about 22.0 psi (15,480 kg/m$^2$). The post-reticulation elongation to break perpendicular to the direction of foam rise was determined to be about 110%.

Compressive tests were conducted on reticulated foam samples as described in Example 2. The post-reticulation compressive strengths, at 50% and 75% compression, each parallel to the direction of foam rise were determined to be 1.49 psi (1,050 kg/m$^2$) and 3.49 psi (2,460 kg/m$^2$), respectively. The post-reticulation compressive sets, parallel to the direction of foam rise, at 50% and 75% compression, each determined after subjecting the reticulated sample to the stated amount of compression for 22 hours at 25° C. then releasing the compressive stress, were determined to be about 4.7% and 7.5%, respectively.

Mushroom-shaped implantable devices, with a flat cylindrical head or cap of about 16 mm in diameter and about 8 mm in length, and a narrow cylindrical stem of about 10 mm diameter and about 8 mm in length, were machined from the reticulated foam. Thereafter, the samples were sterilized by exposing them to a gamma radiation dose of about 2.3 Mrad.

Example 5

Fabrication of Collagen-Coated Implantable Devices

Type I collagen, obtained by extraction from a bovine source, was washed and chopped into fibrils. A 1% by weight collagen aqueous slurry was made by vigorously stirring the collagen and water and adding inorganic acid to a pH of about 3.5. The viscosity of the slurry was about 500 centipoise.

The mushroom-shaped implantable devices prepared according to Example 4 were completely immersed in the collagen slurry, thereby impregnating each implantable device with the slurry. Thereafter, the collagen-slurry impregnated devices were placed on metal trays which were placed onto a lyophilizer shelf pre-cooled to −45° C. After the slurry in the devices froze, the pressure within the lyophilization chamber was reduced to about 100 millitorr, thereby subliming the water out of the frozen collagen slurry leaving a porous collagen matrix deposited within the pores of the reticulated implantable devices. Thereafter, the temperature was slowly raised to about 25° C., then the pressure was returned to 1 atmosphere. The total treatment time in the lyophilizer was about 21-22 hours.

After the implantable devices were removed from the lyophilizer, the collagen was cross-linked by placing the dry collagen impregnated implants in contact with formaldehyde vapor for about 21 hours. Thereafter, the samples were sterilized by exposing them to a gamma radiation dose of about 2.3 Mrad.

Example 6

Discectomy: Implantation of Implants into Pig L1 Through L4 Lumbar Spaces

Yucatan mini pigs weighing about 55-65 kg each underwent L1 through L4 (lumbar spaces) discectomy. The discectomy consisted of a posteriorlateral annulotomy and nuclectomy paralleling the accepted human clinical surgical procedure. The mushroom-shaped implantable devices made by the procedures described in Examples 5 and 4 were implanted in a 3 mm anterior lateral annulotomy to repair the annular defect. Standard closure procedure was followed. Each of the implantable devices of the invention functioned well, e.g., it conformally expanded, obliterated the annular defect, and maintained its position. There were no adverse acute events associated with the procedure and all subject animals recovered uneventfully.

Example 7

Determination of Tissue Ingrowth

In order to determine the extent of cellular ingrowth and proliferation using a reticulated elastomeric matrix implantable device of the invention, surgery is performed in which such reticulated implantable devices are placed in the subcutaneous tissue of Sprague-Dawley rats.

Eight Sprague-Dawley rats weighing from about 375 g to about 425 g each are given access to food and water ad libitum before anesthesia is induced with an intraperitoneal injection of 60 mg/kg sodium pentobarbital.

After anesthesia, the animals are placed on a heating pad and maintained at a temperature of 37° C. for the entire procedure and immediate recovery period. With the animals in the supine position, a small midline abdominal wall incision is made with a number 15 scalpel. The skin and subcutaneous tissue are incised, and superficial fascia and muscle layers are separated from subcutaneous tissue with blunt dissection. One cylindrical polyurethane reticulated elastomeric matrix implantable device, made according to any of the Examples herein and measuring about 5 mm in diameter and 8 mm in length, is then inserted into the subcutaneous pocket near the spine of each animal. The skin is closed with permanent sutures. The animals are returned to their cages and allowed to recover.

The animals are given access to food and water ad libitum for the next 14 days, then each implantable device and the surrounding tissue is collected from the abdomen. At the end of 14 days, each animal is euthanized as follows. Anesthesia is induced with an intraperitoneal injection of 60 mg/kg sodium pentobarbital and the animals are euthanized by carbon dioxide. The previous incision is exposed. The abdomen segment containing the implantable device is removed. For each animal, the implantable device and the full thickness abdominal wall is placed into formalin for preservation.

Histopathology evaluation of the implantable device within the abdomen is performed by conventional H&E staining. The resulting histology slides are examined for evidence of tissue ingrowth and/or proliferation.

Example 8

Implantable Device with Selectively Non-Porous Surface

A piece of reticulated material made according to Example 2 is used. A heated blade with a knife-edge is used to cut a cylinder 10 mm in diameter and 15 mm in length from the piece. The blade temperature is above 130° C. The surfaces of the piece in contact with the heated blade appear to be fused and non-porous from contact with the heated blade. Those surfaces of the piece that are intended to remain porous, i.e., not to fuse, are not exposed to the heated blade.

Example 9

Implantable Device with Selectively Non-Porous Surface

A slightly oversized piece of reticulated material made according to Example 2 is used. The slightly oversized piece is placed into a mold heated to a temperature of above 130° C. The mold is then closed over the piece to reduce the overall dimensions to the desired size. Upon removing the piece from the mold, the surfaces of the piece in contact with the mold appear to be fused and non-porous from contact with the mold. Those surfaces of the piece that are intended to remain porous, i.e., not to fuse, are protected from exposure to the heated mold. A heated blade with a knife-edge is used to cut from the piece a cylinder 10 mm in diameter and 15 mm length.

Example 10

Dip-Coated Implantable Device with Selectively Non-Porous Surface

A piece of reticulated material made according to Example 2 is used. A coating of copolymer containing 90 mole % PGA and 10 mole % PLA is applied to the macro surface as follows. The PGA/PLA copolymer is melted in an extruder at 205° C. and the piece is dipped into the melt to coat it. Those surfaces of the piece that are to remain porous, i.e., not to be coated by the melt, are covered to protect them and not exposed to the melt. Upon removal, the melt solidifies and forms a thin non-porous coating layer on the surfaces of the piece with which it comes in contact.

EXAMPLE 11

Fabrication of a Collagen-Coated Elastomeric Matrix

Type I collagen, obtained by extraction from bovine hide, is washed and chopped into fibrils. A 1% by weight collagen aqueous slurry is made by vigorously stirring the collagen and water and adding inorganic acid to a pH of about 3.5.

A reticulated polyurethane matrix prepared according to Example 2 is cut into a piece measuring 60 mm by 60 mm by 2 mm. The piece is placed in a shallow tray and the collagen slurry is poured over it so that the piece is completely immersed in the slurry for about 15 minutes, and the tray is optionally shaken. If necessary, excess slurry is decanted from the piece and the slurry-impregnated piece is placed on a plastic tray, which is placed on a lyophilizer tray held at 10° C. The lyophilizer tray temperature is dropped from 10° C. to −35° C. at a cooling rate of about 1° C./minute and the pressure within the lyophilizer is reduced to about 75 millitorr. After holding at −35° C. for 8 hours, the temperature of the tray is raised at a rate of about 1° C./hour to 10° C. and then at a rate of about 2.5° C./hour until a temperature of 25° C. is reached. During lyophilization, the water sublimes out of the frozen collagen slurry leaving a porous collagen matrix deposited within the pores of the reticulated polyurethane matrix piece. The pressure is returned to 1 atmosphere.

Optionally, the porous collagen-coated polyurethane matrix piece is subjected to further heat treatment at about 110° C. for about 24 hours in a current of nitrogen gas to crosslink the collagen, thereby providing additional structural integrity.

Example 12

Fabrication of a Crosslinked Reticulated Polyurethane Matrix

Two aromatic isocyanates, RUBINATE® 9433 and RUBINATE 9258 (each from Huntsman; each comprising a mixture of 4,4'-MDI and 2,4'-MDI), were used as the isocyanate component. RUBINATE 9433 has an isocyanate functionality of about 2.01. RUBINATE 9258 has an isocyanate functionality of about 2.33. A modified 1,6-hexanediol carbonate (PESX-619, Hodogaya Chemical Co. Ltd., Kawasaki, Japan), i.e., a diol, with a molecular weight of about 2,000 Daltons was used as the polyol component. Each of these ingredients is a liquid at 25° C. The crosslinker used was glycerol, which is tri-functional. Water was used as the blowing agent. The gelling catalyst was dibutyltin dilaurate (DABCO T-12, from Air Products). The blowing catalyst was triethylenediamine (DABCO 33LV). A silicone-based surfactant was used (TEGOSTAB® BF 2370). A cell-opener was used (ORTEGOL® 501). The proportions of the components that were used is given in Table 5.

TABLE 5

| Ingredient | Parts by Weight |
| --- | --- |
| Polyol Component | 100 |
| Isocyanate Component | |
| RUBINATE 9433 | 60.0 |
| RUBINATE 9258 | 17.2 |
| Isocyanate Index | 1.03 |
| Crosslinker | 2.5 |
| Water | 3.4 |
| Gelling Catalyst | 0.12 |
| Blowing Catalyst | 0.4 |
| Surfactant | 1.0 |
| Cell Opener | 0.4 |

The one-shot approach was used to make the foam. In this technique, all ingredients, except for the isocyanate component, were admixed in a beaker at 25° C. The isocyanate component was then added with high-speed stirring. The foaming mix was then poured into a cardboard form, allowed to rise, and then post-cured for 4 hours at 100° C. The foaming profile was as follows: 10 second mixing time, 15 second cream time, 28 second rise time, and 100 second tack-free time.

The average pore diameter of the foam, as observed by optical microscopy, was about 435 μm.

The density of the foam was determined as described in Example 1. A density value of 2.5 lbs/ft$^3$ (0.040 g/cc) was obtained.

The tensile properties of the foam were determined as described in Example 1. The tensile strength, measured on samples that were cut perpendicular or parallel to the direction of foam rise, was about 41 psi (28,930 kg/m$^2$) and about 69 psi (48,580 kg/m$^2$), respectively. The elongation to break was approximately 76%.

Compressive tests were conducted as described in Example 2. The compressive strength, from measurements made on samples that were cut perpendicular to the direction of foam rise, at 50% and 75% compression, was about 6.1 psi (4,290 kg/m$^2$) and about 19.2 psi (13,510 kg/m$^2$), respectively.

Tear resistance strength of the foam was measured with specimens measuring approximately 152 mm×25 mm×12.7 mm. A 40 mm long cut in the long direction of each specimen was made through the 12.7 mm specimen thickness, beginning at the center of one 25 mm wide side. The tear strength was measured using an INSTRON Universal Testing Instrument Model 1122 with a cross-head speed of 500 mm/min (19.6 inches/minute). The tear strength was determined to be about 2.3 lbs/inch (0.41 kg/cm).

Reticulation of the foam is carried out by the procedure described in Example 2.

Example 13

Fabrication of a Crosslinked Reticulated Polyurethane Matrix

Chemical reticulation of the unreticulated foam of Example 12 is carried out by immersing the foam in a 30% by weight aqueous solution sodium hydroxide for 2 weeks at 25° C. Then, the sample is washed repeatedly with water and dried for 24 hours in an oven at 100° C. The resulting sample is reticulated.

Example 14

Fabrication of a Crosslinked Reticulated Polyurethane Matrix

The isocyanate component was RUBINATE 9258, as described in Example 1. The polyol component was 1,6-hexanediol carbonate (PCDN-980R, Hodogaya Chemical), with a molecular weight of about 2,000 Daltons. This polyol was a solid at 25° C. while the isocyanate was a liquid at this temperature. Water was used as the blowing agent. The gelling catalyst, blowing catalyst, surfactant and cell opener of Example 12 were used. The proportions of the components used are described in Table 6.

TABLE 6

| Ingredient | Parts by Weight |
| --- | --- |
| Polyol Component | 100 |
| Isocyanate Component | 53.8 |
| Isocyanate Index | 1.00 |
| Water | 2.82 |
| Gelling Catalyst | 0.04 |
| Blowing Catalyst | 0.3 |
| Surfactant | 2.04 |
| Cell Opener | 0.48 |
| Viscosity Modifier | 5.70 |

The polyol component was preheated to 80° C. then mixed with the isocyanate component, a propylene carbonate viscosity modifier (which serves as a viscosity depressant for this formulation), surfactant and cell opener to form a viscous liquid. Then, a mixture of water, gelling catalyst and blowing catalyst was added under vigorous mixing. The foaming mix was then poured into a cardboard form, allowed to rise, and then post-cured for 4 hours at 100° C. The foaming profile was as follows: 10 seconds mixing time, 15 seconds cream time, 60 seconds rise time, and 120 seconds tack-free time.

The density, tensile properties, and compressive strength of the foam were determined as described in Examples 1 and 2. A density value of 2.5 lbs/ft$^3$ (0.0400 g/cc) was obtained. The tensile strength, measured on samples that were cut parallel or perpendicular to the direction of foam rise, was about 43 psi (30,280 kg/m$^2$) and 28 psi (19,710 kg/m$^2$), respectively. The elongation to break was approximately 230% irrespective of direction. The compressive strength measured on samples that were cut perpendicular to the direction of foam rise, at 50% and 75% compression, was about 2.41 psi (1,700 kg/m$^2$) and about 4.96 psi (3,490 kg/m$^2$), respectively.

The foam is reticulated by the procedure described in Example 2.

Example 15

Fabrication of a Crosslinked Polyurethane Matrix

The isocyanate component was RUBINATE 9258, as described in Example 1. A polyol comprising 1,6-hexamethylene polycarbonate (Desmophen LS 2391, Bayer Polymers), i.e., a diol, with a molecular weight of about 2,000 Daltons was used as the polyol component and was a solid at 25° C. Distilled water was used as the blowing agent. The blowing catalyst, surfactant, cell-opener and viscosity modifier of Example 1 were used. The proportions of the components that were used is given in Table 7.

TABLE 7

| Ingredient | Parts by Weight |
|---|---|
| Polyol Component | 100 |
| Viscosity Modifier | 5.76 |
| Surfactant | 2.16 |
| Cell Opener | 0.48 |
| Isocyanate Component | 53.8 |
| Isocyanate Index | 1.00 |
| Distilled Water | 2.82 |
| Blowing Catalyst | 0.44 |

The polyol component was liquefied at 70° C. in a circulating-air oven, and 150 g thereof was weighed out into a polyethylene cup. 8.7 g of viscosity modifier was added to the polyol component to reduce the viscosity and the ingredients were mixed at 3100 rpm for 15 seconds with the mixing shaft of a drill mixer to form "Mix-1". 3.3 g of surfactant was added to Mix-1 and the ingredients were mixed as described above for 15 seconds to form "Mix-2". Thereafter, 0.75 g of cell opener was added to Mix-2 and the ingredients were mixed as described above for 15 seconds to form "Mix-3". 80.9 g of isocyanate component was added to Mix-3 and the ingredients were mixed for 60±10 seconds to form "System A".

4.2 g of distilled water was mixed with 0.66 g of blowing catalyst in a small plastic cup for 60 seconds with a glass rod to form "System B".

System B was poured into System A as quickly as possible while avoiding spillage. The ingredients were mixed vigorously with the drill mixer as described above for 10 seconds then poured into a 22.9 cm×20.3 cm×12.7 cm (9 in.×8 in.×5 in.) cardboard box with its inside surfaces covered by aluminum foil. The foaming profile was as follows: 10 seconds mixing time, 18 seconds cream time, and 85 seconds rise time.

2 minutes after the beginning of foaming, i.e., the time when Systems A and B were combined, the foam was place into a circulating-air oven maintained at 100-105° C. for curing for 1 hour. Thereafter, the foam was removed from the oven and cooled for 15 minutes at about 25° C. The skin was removed from each side using a band saw and hand pressure was applied to each side of the foam to open the cell windows. The foam was replaced into the circulating-air oven and post-cured at 100-105° C. for additional 5 hours.

The average pore diameter of the foam, as determined from optical microscopy observations, was about 340 μm.

The density of the foam was determined as described in Example 1. A density value of 2.5 lbs/ft$^3$ (0.040 g/cc) was obtained.

The tensile properties of the foam were determined as described in Example 1. The tensile strength, determined from samples that were cut perpendicular to the direction of foam rise, was 24.64±2.35 psi (17,250±1,650 kg/m$^2$). The elongation to break, determined from samples that were cut perpendicular to the direction of foam rise, was 215±12%.

Compressive tests were conducted as described in Example 2. The compressive strength, determined from samples that were cut parallel to the direction of foam rise at 50% compression, was 1.74±0.4 psi (1,225±300 kg/m$^2$). The compression set, determined from samples that were cut parallel to the direction of foam rise after subjecting the samples to 50% compression for 22 hours at 40° C. then releasing the compressive stress, was about 2%.

The tear resistance strength of the foam was conducted as described in Example 12. The tear strength was determined to be 2.9±0.1 lbs/inch (1.32±0.05 kg/cm).

The pore structure and its inter-connectivity was characterized using a Liquid Extrusion Porosimeter (Porous Materials, Inc., Ithaca, N.Y.). In this test, the pores of a 25.4 mm diameter cylindrical sample 4 mm thick were filled with a wetting fluid having a surface tension of about 19 dynes/cm then that sample was loaded into a sample chamber with a microporous membrane, having pores about 27 μm in diameter, placed under the sample. Thereafter, the air pressure above the sample was increased slowly to extrude the liquid from the sample. For a low surface tension wetting fluid, such as the one used, the wetting liquid that spontaneously filled the pores of the sample also spontaneously filled the pores of the microporous membrane beneath the sample when the pressure above the sample began to increase. As the pressure continued to increase, the largest pores of the sample emptied earliest. Further increases in the pressure above the sample led to the emptying of increasingly smaller sample pores as the pressure continued to increase. The displaced liquid passed through the membrane and its volume was measured. Thus, the volume of the displaced liquid allowed the internal volume accessible to the liquid, i.e., the liquid intrusion volume, to be obtained. Moreover, measurement of the liquid flow under increasing pressure but in the absence of the microporous membrane beneath the sample, this time using water as the fluid, allowed the liquid permeability to be determined. The liquid intrusion volume of the foam was determined to be 4 cc/g and the permeability of water through the foam was determined to be 1 Darcy.

Example 16

Reticulation of a Crosslinked Polyurethane Foam

Reticulation of the foam described in Example 15 was carried out by the procedure described in Example 2.

Tensile tests were conducted on reticulated foam samples as described in Example 15. The post-reticulation tensile strength, measured on samples that were cut perpendicular to the direction of foam rise, was about 23.5 psi (16,450 kg/m$^2$). The post-reticulation elongation to break, measured on samples that were cut perpendicular to the direction of foam rise, was about 194%.

Compressive tests of the reticulated foam were conducted as described in Example 2. The post-reticulation compressive strength, measured on samples that were cut parallel to the direction of foam rise, at 50% and 75% compression, was about 0.9 psi (625 kg/m$^2$) and about 2.5 psi (1,770 kg/m$^2$), respectively.

The pore structure and its inter-connectivity is characterized using a Liquid Extrusion Porosimeter as described in Example 15. The liquid intrusion volume of the reticulated foam was determined to be 28 cc/g and the permeability of water through the reticulated foam was determined to be 184 Darcys. These results demonstrate, e.g., the interconnectivity and continuous pore structure of the reticulated foam.

Example 17

Fabrication of a Reticulated Polycarbonate Polyurethane Matrix by Lyophilization A homogeneous solution of 10% by weight of BIONATE® 80A grade polycarbonate polyurethane in DMSO is prepared by tumbling and agitating the BIONATE pellets in the DMSO using a rotary spider turning at 5 rpm over a 3 day period. The solution is made in a sealed container to minimize solvent loss.

The solution is placed in a shallow plastic tray and held at 27° C. for 30 minutes. The lyophilizer tray temperature is dropped to −10° C. at a cooling rate of 1.0° C./minute and the pressure within the lyophilizer is reduced to 50 millitorr. After 24 hours, the temperature of the tray is raised at a rate of about 0.5° C./hour to 8° C. and held there for 24 hours. Then, the temperature of the tray is raised at a rate of about 1° C./hour until a temperature of 25° C. is reached. Then, the temperature of the tray is further raised at a rate of about 2.5° C./hour until a temperature of 35° C. is reached. During lyophilization, DMSO sublimes leaving a reticulated polycarbonate polyurethane matrix piece. The pressure is returned to 1 atmosphere and the piece is removed from the lyophilizer.

Any remaining DMSO is washed off of the piece by repeatedly rinsing it with water. The washed piece is allowed to air-dry.

Disclosures Incorporated

The entire disclosure of each and every U.S. patent and patent application, each foreign and international patent publication and each other publication, and each unpublished patent application that is referenced in this specification, or elsewhere in this patent application, is hereby specifically incorporated herein, in its entirety, by the respective specific reference that has been made thereto.

While illustrative embodiments of the invention have been described above, it is understood that many and various modifications will be apparent to those in the relevant art, or may become apparent as the art develops. Such modifications are contemplated as being within the spirit and scope of the invention or inventions disclosed in this specification.

What is claimed is:

1. An implantable device for promoting tissue ingrowth therein comprising:
a reticulated, resiliently-compressible, elastomeric matrix comprising a continuous network of solid structures defining a void space therein, wherein said void space comprises a plurality of interconnected pores forming a continuous network of intercommunicating passageways extending from an interior portion to an exterior surface of said matrix,
wherein said matrix comprises a biocompatible, crosslinked polycarbonate polyurethane-urea formed by a reaction of a mixture comprising:
(i) a polycarbonate polyol, and
(ii) an isocyanate component comprising at least about 5% by weight of said isocyanate component of 2,4'-diphenylmethane diisocyanate, and
wherein said matrix is substantially free of isocyanurate linkages.

2. The device according to claim 1, wherein said mixture further comprises glycerol.

3. The device according to claim 2, wherein said polycarbonate polyurethane-urea comprises crosslinks by said glycerol.

4. The implantable device of claim 1, wherein an average number of isocyanate groups per molecule in said isocyanate component is greater than 2.

5. The implantable device of claim 4, wherein said average number of isocyanate groups per molecule in said isocyanate component is about 2.33 or greater.

6. The device according to claim 1, wherein said plurality of pores have an average diameter or other largest transverse dimension of at least about 20 μm.

7. The device according to claim 6, wherein said plurality of pores have an average diameter or other largest transverse dimension of at least about 50 μm.

8. The device according to claim 7, wherein said plurality of pores have an average diameter or other largest transverse dimension of at least about 150 μm.

9. The device according to claim 8, wherein said plurality of pores have an average diameter or other largest transverse dimension of at least about 250 μm.

10. The device according to claim 1, wherein said isocyanate component comprises from about 5% to about 50% by weight of said isocyanate component of 2,4'-diphenylmethane diisocyanate.

11. The device according to claim 10, wherein said isocyanate component comprises from about 5% to about 40% by weight of said isocyanate component of 2,4'-diphenylmethane diisocyanate.

12. The device according to claim 11, wherein said isocyanate component comprises from about 5% to about 35% by weight of said isocyanate component of 2,4'-diphenylmethane diisocyanate.

13. The device according to claim 1, wherein said isocyanate component further comprises 4,4'-diphenylmethane diisocyanate.

14. The device according to claim 1, wherein said isocyanate component consists of: (a) at least about 5% by weight of said isocyanate component of 2,4'-diphenylmethane diisocyanate, and (b) 4,4'-diphenylmethane diisocyanate.

15. The device according to claim 1, wherein said matrix is free of isocyanurate linkages.

16. The device according to claim 1, wherein said matrix is substantially free of allophanate and biuret linkages.

17. The device according to claim 16, wherein said matrix is free of allophanate and biuret linkages.

18. The device according to claim 1, wherein said polycarbonate polyol comprises a polycarbonate diol.

19. The device according to claim 1, wherein said void space comprises from about 70% to about 99% of the volume of said matrix.

20. The device according to claim 19 wherein said void space comprises from about 80% to about 98% of the volume of said matrix.

21. The device according to claim 20, wherein said void space comprises from about 90% to about 98% of the volume of said matrix.

22. The device according to claim 1, wherein said isocyanate component has an isocyanate index from about 0.9 to about 1.02.

23. The device according to claim 22, wherein said isocyanate component has an isocyanate index from about 0.9 to about 1.0.

24. The device according to claim 1, wherein said matrix is stable for at least 29 days in a biological environment.

25. The device according to claim 1, wherein said matrix is stable for at least six months in a biological environment.

26. The device according to claim 1, wherein said mixture comprises from about 10 to about 90 parts by weight of said isocyanate component per 100 parts by weight of said polycarbonate polyol.

* * * * *